United States Patent
Brines et al.

(10) Patent No.: US 7,767,643 B2
(45) Date of Patent: Aug. 3, 2010

(54) PROTECTION, RESTORATION, AND ENHANCEMENT OF ERYTHROPOIETIN-RESPONSIVE CELLS, TISSUES AND ORGANS

(75) Inventors: Michael Brines, Woodbridge, CT (US); Anthony Cerami, Croton-On-Hudson, NY (US); Carla Cerami, Sleepy Hollow, NY (US)

(73) Assignee: The Kenneth S. Warren Institute, Inc., Ossining, NY (US)

( * ) Notice: Subject to any disclaimer, the term of this patent is extended or adjusted under 35 U.S.C. 154(b) by 736 days.

(21) Appl. No.: 10/185,841

(22) Filed: Jun. 26, 2002

(65) Prior Publication Data

US 2003/0104988 A1    Jun. 5, 2003

Related U.S. Application Data

(63) Continuation of application No. PCT/US01/49479, filed on Dec. 28, 2001.

(60) Provisional application No. 60/259,245, filed on Dec. 29, 2000.

(51) Int. Cl.
*A61K 38/18* (2006.01)
*C07K 14/505* (2006.01)

(52) U.S. Cl. .............................. 514/8; 530/397; 530/402

(58) Field of Classification Search ....................... None
See application file for complete search history.

(56) References Cited

U.S. PATENT DOCUMENTS

| | | | |
|---|---|---|---|
| 4,343,782 A * | 8/1982 | Shapiro | 435/7.2 |
| 4,377,513 A | 3/1983 | Sugimoto et al. | |
| 4,658,019 A | 4/1987 | Kung et al. | |
| 4,703,008 A | 10/1987 | Lin | |
| 4,806,524 A | 2/1989 | Kawaguchi et al. | |
| 4,835,260 A | 5/1989 | Shoemaker | |
| 4,992,419 A | 2/1991 | Woog et al. | |
| 5,194,596 A | 3/1993 | Tischer et al. | |
| 5,278,065 A | 1/1994 | D'Andrea | |
| 5,292,654 A | 3/1994 | Yoshimura | |
| 5,350,836 A | 9/1994 | Kopchick et al. | |
| 5,354,934 A | 10/1994 | Pitt et al. | |
| 5,457,089 A | 10/1995 | Fibi et al. | |
| 5,547,933 A | 8/1996 | Lin | |
| 5,571,787 A | 11/1996 | O'Brien et al. | |
| 5,591,713 A | 1/1997 | Igari et al. | |
| 5,604,198 A | 2/1997 | Poduslo et al. | |
| 5,614,184 A | 3/1997 | Sytkowski et al. | |
| 5,618,698 A | 4/1997 | Lin | |
| 5,621,080 A | 4/1997 | Lin | |
| 5,625,035 A | 4/1997 | Clemons | |
| 5,661,125 A | 8/1997 | Strickland | |
| 5,696,080 A | 12/1997 | O'Brien | |
| 5,700,909 A | 12/1997 | O'Brien | |
| 5,714,459 A | 2/1998 | O'Brien | |
| 5,750,376 A | 5/1998 | Weiss et al. | |
| 5,756,349 A | 5/1998 | Lin | |
| 5,763,198 A | 6/1998 | Hirth et al. | |
| 5,767,078 A | 6/1998 | Johnson et al. | |
| 5,773,569 A | 6/1998 | Wrighton et al. | |
| 5,824,672 A | 10/1998 | Simpkins et al. | |
| 5,830,851 A | 11/1998 | Wrighton et al. | |
| 5,835,382 A | 11/1998 | Wilson et al. | |
| 5,856,298 A | 1/1999 | Strickland | |
| 5,888,772 A | 3/1999 | Okasinski et al. | |
| 5,955,422 A | 9/1999 | Lin | |
| 5,997,865 A | 12/1999 | Bennett et al. | |
| 6,048,971 A | 4/2000 | Sytkowski et al. | |
| 6,071,970 A | 6/2000 | Mueller et al. | |
| 6,103,526 A | 8/2000 | Smith et al. | |
| 6,121,246 A | 9/2000 | Isner | |
| 6,153,407 A | 11/2000 | Sytkowski et al. | |
| 6,165,783 A | 12/2000 | Weiss et al. | |
| 6,200,567 B1 | 3/2001 | Lopez et al. | |
| 6,242,570 B1 | 6/2001 | Sytkowski | |
| 6,291,661 B1 | 9/2001 | Graddis et al. | |
| 6,340,742 B1 | 1/2002 | Burg et al. | |
| 6,399,336 B1 | 6/2002 | Paulson et al. | |
| 6,440,932 B1 | 8/2002 | Lehmann et al. | |
| 6,475,717 B1 | 11/2002 | Enssle et al. | |
| 6,489,293 B1 | 12/2002 | Sytkowski et al. | |
| 6,521,245 B1 | 2/2003 | Zaharia | |
| 6,531,121 B2 | 3/2003 | Brines et al. | |
| 6,583,272 B1 | 6/2003 | Bailon | |
| 6,645,522 B2 | 11/2003 | Naeff et al. | |
| 6,673,575 B1 | 1/2004 | Franze et al. | |
| 6,747,002 B2 | 6/2004 | Cheung et al. | |
| 6,784,154 B2 | 8/2004 | Westenfelder | |
| 6,855,544 B1 | 2/2005 | Hateboer et al. | |
| 6,930,086 B2 | 8/2005 | Tischer | |
| 7,053,184 B2 | 5/2006 | Lee | |
| 7,087,224 B2 | 8/2006 | Kay et al. | |
| 7,091,326 B2 | 8/2006 | Lee et al. | |
| 7,098,318 B2 | 8/2006 | Lee et al. | |
| 7,214,532 B2 | 5/2007 | Stern et al. | |
| 7,220,555 B2 | 5/2007 | Paulson et al. | |

(Continued)

FOREIGN PATENT DOCUMENTS

CA    2294448    12/1998

(Continued)

OTHER PUBLICATIONS

Bany-Mohammed et al. Recombinant human erythropoietin:possible role as an antioxidant in premature rabbits. Pediatric Research. vol. 40, No. 3, pp. 381-387 (1996).*

(Continued)

*Primary Examiner*—Marianne P Allen
*Assistant Examiner*—Regina M DeBerry
(74) *Attorney, Agent, or Firm*—Jones Day

(57) ABSTRACT

Methods and compositions are provided for protecting or enhancing an erythropoietin-responsive cell, tissue, organ or body part function or viability in vivo, in situ or ex vivo in mammals, including human beings, by systemic or local administration of an erythropoietin receptor activity modulator, such as an erythropoietin or a modified erythropoietin.

13 Claims, 15 Drawing Sheets

U.S. PATENT DOCUMENTS

| | | | |
|---|---|---|---|
| 7,262,166 | B2 | 8/2007 | Kinstler et al. |
| 7,297,680 | B2 | 11/2007 | Opstelten et al. |
| 7,300,915 | B2 | 11/2007 | Campana et al. |
| 7,300,916 | B2 | 11/2007 | Yasuda et al. |
| 7,304,031 | B2 | 12/2007 | Opstelten et al. |
| 7,309,687 | B1 | 12/2007 | Brines et al. |
| 7,345,019 | B1 | 3/2008 | Brines et al. |
| 7,410,941 | B1 | 8/2008 | Brines et al. |
| 7,504,248 | B2 | 3/2009 | Marzio et al. |
| 2002/0052309 | A1 | 5/2002 | Anagnostou et al. |
| 2002/0061849 | A1 | 5/2002 | Nielsen et al. |
| 2002/0081734 | A1 | 6/2002 | Choi et al. |
| 2002/0160460 | A1 | 10/2002 | Paulson et al. |
| 2003/0003529 | A1 | 1/2003 | Bayer |
| 2003/0040037 | A1 | 2/2003 | Bayer |
| 2003/0072737 | A1 | 4/2003 | Brines et al. |
| 2003/0118547 | A1 | 6/2003 | Vandenberg |
| 2003/0120045 | A1 | 6/2003 | Bailon |
| 2003/0134798 | A1 | 7/2003 | Brines et al. |
| 2004/0009902 | A1 | 1/2004 | Boime |
| 2004/0091961 | A1 | 5/2004 | Evans et al. |
| 2004/0122216 | A1 | 6/2004 | Nielsen et al. |
| 2004/0209812 | A1 | 10/2004 | Farrell et al. |
| 2004/0214236 | A1 | 10/2004 | Brines et al. |
| 2005/0106722 | A1 | 5/2005 | Jones et al. |
| 2005/0164386 | A1 | 7/2005 | Uytdehaag et al. |
| 2005/0170463 | A1 | 8/2005 | Bout et al. |
| 2005/0176627 | A1 | 8/2005 | Cerami et al. |
| 2006/0034799 | A1 | 2/2006 | Brines et al. |
| 2006/0099685 | A1 | 5/2006 | Yallop et al. |
| 2006/0216757 | A1 | 9/2006 | Brines et al. |
| 2007/0054394 | A1 | 3/2007 | Bout et al. |
| 2007/0117742 | A1 | 5/2007 | Opstelten et al. |
| 2007/0129293 | A1 | 6/2007 | Coleman et al. |
| 2007/0231860 | A1 | 10/2007 | Uytdehaag et al. |
| 2007/0275439 | A1 | 11/2007 | Opstelten |
| 2007/0298031 | A1 | 12/2007 | Brines et al. |
| 2007/0298464 | A1 | 12/2007 | Optelten et al. |
| 2008/0014193 | A1 | 1/2008 | Brines et al. |
| 2008/0032922 | A1 | 2/2008 | Opstelten et al. |
| 2008/0045412 | A1 | 2/2008 | Brines et al. |
| 2008/0050403 | A1 | 2/2008 | Marzio et al. |
| 2008/0305990 | A1 | 12/2008 | Brines et al. |
| 2009/0004202 | A1 | 1/2009 | Brines et al. |
| 2009/0136519 | A1 | 5/2009 | Brines et al. |
| 2009/0233844 | A1 | 9/2009 | Brines et al. |

FOREIGN PATENT DOCUMENTS

| | | |
|---|---|---|
| DE | 198 57 609 | 6/2000 |
| EP | 0555880 | 8/1993 |
| EP | 0640619 | 1/1995 |
| EP | 0668351 | 8/1995 |
| EP | 0883343 | 4/1997 |
| EP | 1064951 | 1/2001 |
| EP | 1440157 | 5/2003 |
| EP | 1625858 | 2/2006 |
| EP | 1633383 | 3/2006 |
| EP | 1831381 | 7/2006 |
| EP | 1889627 | 2/2008 |
| FR | 2 823 220 | 10/2002 |
| JP | 05092928 | 4/1993 |
| JP | 5-246885 | 9/1993 |
| WO | WO 85/02610 | 6/1985 |
| WO | WO 86/03520 | 6/1986 |
| WO | WO 90/11354 | 10/1990 |
| WO | WO 91/05867 | 5/1991 |
| WO | WO 91/06667 | 5/1991 |
| WO | WO 91/09955 | 7/1991 |
| WO | WO 92/08493 | 5/1992 |
| WO | WO 93/09222 | 5/1993 |
| WO | WO 93/25221 | 12/1993 |
| WO | WO 94/12650 | 6/1994 |
| WO | WO 94/24160 | 10/1994 |
| WO | WO 94/28024 | 12/1994 |
| WO | WO 95/05465 | 2/1995 |
| WO | WO 95/31560 | 11/1995 |
| WO | WO 96/14081 | 5/1996 |
| WO | WO 97/08307 | 3/1997 |
| WO | WO 97/14307 | 4/1997 |
| WO | WO 97/18318 | 5/1997 |
| WO | WO 97/32895 | 12/1997 |
| WO | WO 98/10650 | 3/1998 |
| WO | WO 98/18926 | 5/1998 |
| WO | WO 98/58660 | 12/1998 |
| WO | WO 99/21966 | 5/1999 |
| WO | WO 00/24893 | 5/2000 |
| WO | WO 00/32772 | 6/2000 |
| WO | WO 00/35475 | 6/2000 |
| WO | WO 00/61164 | 10/2000 |
| WO | WO 01/02017 | 1/2001 |
| WO | WO 01/81405 | 11/2001 |
| WO | WO 01/82952 | 11/2001 |
| WO | WO 01/82953 | 11/2001 |
| WO | WO 01/87329 | 11/2001 |
| WO | WO 02/00721 | 1/2002 |
| WO | WO 02/10743 | 2/2002 |
| WO | WO 02/14356 | 2/2002 |
| WO | WO 02/49673 | 6/2002 |
| WO | WO 02/053580 | 7/2002 |
| WO | WO 02/085940 | 10/2002 |
| WO | WO 03/029291 | 4/2003 |
| WO | WO 03/038100 | 5/2003 |
| WO | WO 03/089468 | 10/2003 |
| WO | WO 04/003176 | 1/2004 |
| WO | WO 04/004656 | 1/2004 |
| WO | WO 04/022577 | 3/2004 |
| WO | WO 2004/022577 | 3/2004 |
| WO | WO 2004/087063 | 10/2004 |
| WO | WO 04/096148 | 11/2004 |
| WO | WO 04/112693 | 12/2004 |
| WO | WO 2004/112693 | 12/2004 |
| WO | WO 05/025606 | 3/2005 |
| WO | WO 05/032467 | 4/2005 |
| WO | WO 05/084364 | 9/2005 |
| WO | WO 05/117927 | 12/2005 |
| WO | WO 06/002646 | 1/2006 |
| WO | WO 06/014349 | 2/2006 |
| WO | WO 06/014466 | 2/2006 |
| WO | WO 2006/070011 | 7/2006 |
| WO | WO 2006/129755 | 12/2006 |

OTHER PUBLICATIONS

Bemaudin et al., 1999, "A potential role for erythropoictin in focal permanent cerebral ischemia in mice", J. Cereb. Blood Flow Metab. 19:643-651.

Bondy, 1995, "The relaxation of oxidative stress and hyperexcitation to neurological disease", Proc. Soc. Exp. Biol. Med. 208:337-345.

Brines et al., 2000, "Erythropoietin crosses the blood-brain barrier to -protect against experimental brain injury", Proc. Natl. Acad. Sci. USA 97:10526-10531.

Campana et al., 1998, "Identification of a neurotrophic sequence in erythropoietin", Int. J. Mol. Med. 1:235-241.

Digicaylioglu et al. 1995, "Localization of specific erythropoietin binding sites in defined areas of the mouse brain.", Proc. Natl. Acad. Sci. USA 92:3717-3720.

Dipaolo et al., 1992, "Effects of uremia and dialysis on brain electrophysiology after recombinant erythropoietin treatment", ASAIO J. 38:M477-M480.

Grimm et al., 1990, "Improvement of brain function in hemodialysis patients treated with erythropoietin", Kidney Intl. 38:480-486.

Hefti, 1997, "Pharmacology of neurotrophic factors", Annu. Rev. Pharmacol. Toxicol. 37:239-267.

Hengemihle et al., 1996, "Chronic treatment with human recombinant erythropoietin increases hematocrit and improves water maze performance in mice", Physiol. Behav. 59:153-156.

Hirakata et al., 1992, "CBF and oxygen metabolism in hemodialysis patients: effects of anemia correction with recombinant human EPO", Am. J. Physiol. 262:F737-F743.

Juul et al., 1998, "Erythropoietin and erythropoietin receptor in the developing human central nervous system", Pediatr. Res. 43:40-49.

Konishi et al., 1993, "Trophic effect of erythropoietin and other hematopoietic factors on central cholinergic neurons in vitro and in vivo", Brain Res. 609:29-35.

Kopf et al., 1994, "Memory-improving actions of glucose: involvement of a central cholinergic muscarinic mechanism.", Behav. Neural Biol. 62:237-243.

Latini et al., 1998, "Comparative efficacy of a DA2/α2 agonist and a β-blocker in reducing adrenergic drive and cardiac fibrosis in an experimental model of left ventricular dysfunction after coronary artery occlusion", J. Cardiovasc. Pharmacol. 31:601-608.

Li et al., 1998, "A single pre-training glucose injection induces memory facilitation in rodents performing various tasks: contribution of acidic fibroblast growth factor", Neurosci. 85:785-794.

Lipinski et al., 1995, "Nerve growth factor facilitates conditioned taste aversion learning in normal rats", Brain Res. 692:143-153.

Liu et al., 1997, "Regulated human erythropoietin receptor expression in mouse brain", J. Biol. Chem. 272:32395-32400.

Liu et al., 1994, "Tissue specific expression of human erythropoietin receptor in transgenic mice", Devel. Biol. 166:159-169.

Marrero et al., 1998, "Erythropoietin receptor-operated $Ca^{2+}$ channels: activation by phospholipase C-γ1", Kidney Intl. 53:1259-1268.

Marsh et al., 1991, "rHuEPO treatment improves brain and cognitive function of anemic dialysis patients", Kidney Intl. 39:155-163.

Marti et al., 1997, "Detection of erythropoietin in human liquor: intrinsic erythropoietin production in the brain", Kidney Intl. 51:416-418.

Marti et al., 1996, "Erythropoietin gene expression in human, monkey and murine brain", Eur. J. Neurosci. 8:666-676.

Masuda et al., 1997, "Insulin-like growth factors and insulin stimulate erythropoietin production in primary cultured astrocytes", Brain Res. 746:63-70.

Masuda et al., 1994, "A novel site of erythropoietin production. Oxygen-dependent production in cultured rat astrocytes", J. Biol. Chem. 269:19488-19493.

Masuda et al., 1993, "Functional erythropoietin receptor of the cells with neural characteristics. Comparison with receptor properties of erythroid cells", J. Biol. Chem. 268:11208-11216.

Morishita et al., 1997, "Erythropoietin receptor is expressed in rat hippocampal and cerebral cortical neurons, and erythropoietin prevents in vitro glutamate-induced neuronal death", Neurosci. 76:105-116.

Moss and Scholey, 1996, "Oxygen administration enhances memory formation in healthy young adults", Psychopharmacol. 124:255-260.

Nakamura et al., 1998, "Elevated levels of erythropoietin in cerebrospinal fluid of depressed patients", Am. J. Med. Sci. 315:199-201.

Nissenson et al., 1991, "Recombinant human erythropoietin and renal anemia: molecular biology, clinical efficacy and nervous system effects", Ann. Int. Med. 114:402-416.

Nissenson, 1989, "Recombinant human erythropoietin: impact on brain and cognitive function, exercise tolerance, sexual potency and quality of life", Sem. Nephrol. 9(suppl. 2):25-31.

Ogden, 1989, "Monitoring considerations in recombinant human erythropoietin therapy", Sem. Nephrol. 9(suppl. 2):12-15.

Pardridge, 1997, "Drug delivery to the brain", J. Cerebral Blood Flow Metab. 17:713-731.

Pardridge et al., 1991, "Selective transport of an anti-transferrin receptor antibody through the blood-brain barrier in vivo", J. Pharmacol. Exp. Ther. 27:66-70.

Poduslo et al., 1994, "Macromolecular premeability across the blood-nerve and blood-brain barriers", Proc. Natl. Acad. Sci. USA 91:5705-5709.

Prendergast et al., 1997, "Nitric oxide synthase inhibition impairs spatial navigation learning and induces conditioned taste aversion", Pharmacol. Biochem. Behav. 57:347-352.

Rose and Audus, 1998, "Receptor-mediated angiotensin II transcytosis by brain microvessel endothelial cells", Peptides 19:1023-1030.

Sadamoto et al., 1998, "Erythropoietin prevents place navigation disability and cortical infarction in rats with permanent occlusion of the middle cerebral artery", Biochem. Biophys. Res. Comm. 253:26-32.

Sakanaka et al., 1998, "In vivo evidence that erythropoietin protects neurons from ischemic damage", Proc. Natl. Acad. Sci. USA 95:4635-4640.

Tabira et al., 1995, "Neurotrophic effect of hematopoietic cytokines on cholinergic and other neurons in vitro", Int. J. Devl. Neurosci. 13:241-252.

Wolcott et al., 1989, "Recombinant human erythropoietin treatment may improve quality of life and cognitive function in chronic hemodialysis patients", Am. J. Kidney Dis. 14:478-485.

Wu and Pardridge, 1999, "Neuroprotection with noninvasive neurotrophin delivery to the brain", Neurobiol. 96:254-259.

Yamaji et al., 1996, "Brain capillary endothelial cells express two forms of erythropoietin receptor mRNA", Eur. J. Biochem. 239:494-500.

Alafaci et al., 2000, "Effect of Recombinant Human Erythropoietin on Cerebral Ischemia Following Experimental Subarachnoid Hemorrhage," Eur. J. Phar., 406:219-225.

Annable et al., 1972, "The Second International Reference Preparation of Erythropoietin, Human, Urinary, for Bioassay," Bull. Org. mond. Sante, 47:99-112.

Ashwell et al., 1978, "A Protein from Mammalian Liver that Specifically Binds Galactose-Terminated Glycoproteins," Meth. Enzymol., 50:287-291.

Bauer, 1995, "The Oxygen Sensor That Controls EPO Production: Facts and Fancies," J. Perinat. Med., 23:7-12.

Briggs et al., 1974, "Hepatic Clearance of Intact and Desialylated Erythropoietin," Am. J. Physiol., 227:1385-1388.

Bruneval et al., 1993, "Erythropoietin Synthesis by Tumor Cells in a Case of Meningioma Associated With Erythrocytosis," Blood, 81:1593-1597.

Camiscoli et al., 1968, "Comparative Assay of Erythropoietin Standards," Annals New York Acad. Sci., 149:40-45.

Claus-Walker and Dunn, 1984, "Spinal Cord Injury and Serum Erythropoietin," Arch. Phys. Med. Rehabil., 65:370-374.

Cotes, 1968, "Quantitative Estimation of Erythropoietin," Part I. Assay and Standardization of Erythropoietin, Annals New York Acad. Sci., 149:12-17.

Cotes and Bangham, 1961, "Bio-Assay of Erythropoietin in Mice Made Polycythaemic By Exposure to Air at a Reduced Pressure," Nature, 191:1065-1067.

Cotes and Bangham, 1966, "The International Reference Preparation of Erythropoietin," Bull. Org. mond. Sante, 35:751-760.

Dordal et al., 1985, "The Role of Carbohydrate in Erythropoietin Action," Endocrinol., 116:2293-2299.

Dube et al, 1988, "Glycosylation at Specific Sites of Erythropoietin is Essential for Biosynthesis, Secretion, and Biological Function," J. Biol. Chem., 263:17516-17521.

Eur. Pharmacopoeia, 1997, p. 5.

Eur. Pharmacopoeia, Suppl. 2001, pp. 777-782.

Fukuda et al., 1989, "Survival of Recombinant Erythropoietin in the Circulation: The Role of Carbohydrates," Blood, 73:84-89.

Garthoff, 1995, "Safety and Efficacy Testing of Hormones and Related Products," The Report and Recommendations of ECVAM Workshop 9, A.T.L.A., 23:699-711.

Goldwasser et al., 1974, "On the Mechanism of Erythropoietin-Induced Differentiation," XIII. The Role of Sialic Acid in Erythropoietin Action, J. Biol. Chem., 249:4202-4206.

Goldwasser et al., 1975, "An Assay for Erythropoietin in Vitro at the Milliunit Level," Endo., 97:315-323.

Goldwasser and Gross, "Erythropoietin: Assay and Study of Its Mode of Action," Hormone Assays, pp. 109-121.

Hammond et al., 1968, "Production, Utilization and Excretion of Erythropoietin: I. Chronic Anemias. II. Aplastic Crisis. III. Erythropoietic Effects of Normal Plasma," Erythropoietin, 149:516-527.

Horton et al., 1991, "Von Hippel-Lindau Disease and Erythrocytosis: Radioimmunoassay of Erythropoietin in Cyst Fluid From a Brainstem Hemangioblastoma," *Neurology*, 41:753-754.

Imai et al., 1990, "Physicochemical and Biological Characterization of Asialoerythropoietin," *Eur. J. Biochem.*, 194:457-462.

Keighley, 1968, "Further Experiences with Assays, Units, and Standards of Erythropoietin," *Annals New York Acad. Sci.*, 149:18-24.

Kohama et al., 2000, "Large Uterine Myoma with Erythropoietin Messenger RNA and Erythrocytosis," *Obstetrics and Gynecology*, 96:826-828.

Lowy et al., 1960, "Inactivation of Erythropoietin by Neuraminidase and by Mild Substitution Reactions," *Nature*, 185:102-103.

Matsuyama et al., 2000, "Erythrocytosis Caused by an Erythropoietin-Producing Hepatocellular Carcinoma," *J. Surg. Oncology*, 75:197-202.

Miyake et al., 1977, "Purification of Human Erythropoietin," *J. Biol. Chem.*, 252:5558-5564.

Morrell et al., 1968, "Physical and Chemical Studies on Ceruloplasmin," Metabolic Studies on Sialic Acid-Free Ceruloplasmin In Vivo, *J. Biol. Chem.*, 243:155-159.

Nakamura et al., 1998, "Elevated Levels of Erythropoietin in Cerebrospinal Fluid of Depressed Patients," *Am. J. Med. Sci.*, 315:199-201.

Shiramizu et al., 1994, "Constitutive Secretion of Erythropoietin by Human Renal Adenocarcinoma Cells in Vivo and in Vitro," *Exp. Cell Res.*, 215:249-256.

Shore et al., 1968, "Quantitative Estimation of Erythropoietin," *Annals New York Acad. Sci.*, 149:46-48.

Spivak and Hogans, 1989, "The In Vivo Metabolism of Recombinant Human Erythropoietin in the Rat," *Blood*, 73:90-99.

Storring et al., 1998, "Epoietin Alfa and Beta Differ In Erythropoietin Isoform Compositions and Biological Properties," *British J. Haematology*, 100:79-89.

Storring and Gaines Das, 1992, "The International Standard for Recombinant DNA-Derived Erythropoietin: Collaborative Study of Four Recombinant DNA-derived Erythropoietins and Two Highly Purified Human Urinary Erythropoietins," *J. Endocrinol.*, 134:459-484.

Suzuki et al., 2001, "Erythropoietin Synthesis by Tumour Tissues in a Patient With Uterine Myoma and ERythrocytosis," *British J. Haematology*, 113:49-51.

Weiland et al., "In vivo Activity of Asialo-Erythropoietin in Combination with Asialo-Glycoproteins," 1982, *Blut*, 44:173-175.

Anagnostou et al., 1994, "Erythropoietin receptor mRNA expression in human endothelial cells", Proc. Natl. Acad. Sci. USA 91:3974-3978.

Benyo and Conrad, 1999, "Expression of erythropoietin receptor by trophoblast cells in the human placenta", Biol. Reproduct. 60:861-870.

Bernaudin et al., 2000, Neurons and astrocytes express EPO mRNA: oxygen-sensing mechanisms that involve the redox-state of the brain, Glia 30:271-278.

Ehrenreich et al., 2002, "Erythropoietin therapy for acute stroke is both safe and beneficial", Molec. Med. 8(8):495-505.

Farrell et al., 2001, "Erythropoietin crosses the blood brain barrier", Blood 98:148b (abstr. # 4265; 43$^{rd}$ Annual Meeting of the American Society of Hematology, Orlando FL, Dec. 7-11, 2001).

Gorio et al., 2002, "Recombinant human erythropoietin counteracts secondary injury and markedly enhances neurological recovery from experimental spinal cord trauma", Proc. Natl. Acad. Sci. USA 99:9450-9455 (PNAS Early Edition www.pnas.org/cgi/doi/10.1073/pnas.142287899).

Grasso et al., 2002, "Beneficial effects of systemic administration of recombinant human erythrpoietin in rabbits subjected to subarachnoid hemorrhage", Proc. Natl. Acad. Sci. USA 99:5627-5631.

Gregory et al., 1999, "GATA-1 and erythropoietin cooperate to promote erythroid cell survival by regulating bcl-$x_L$ expression", Blood 94:87-96.

Junk et al., 2002, "Erythropoietin administration protects retinal neurons from acute ischemia-reperfusion injury", Proc. Natl. Acad. Sci. USA 99:10659-10664 (PNAS Early Edition www.pnas.org/cgi/doi/10.1073/pnas.152321399).

Juul et al., 2001, "Recombinant erythropoietin (EPO) crosses the blood brain barrier (BBB) in preterm fetal sheep", Soc. for Neuroscience Abstracts 27:929 (31$^{st}$ Annual Meeting of the Society for Neuroscience, San Diego, CA Nov. 10-15, 2001).

Juul et al., 1998, "Tissue distribution of erythropoietin and erythropoietin receptor in the developing human fetus", Early Human Devel. 52:235-249.

Li et al., 1996, "Erythropoietin receptors are expressed in the central nervous system of mid-trimester human fetuses", Pediatr. Res. 40:376-380.

Liu et al., 1996, "Transgenic mice containing the human erythropoictin receptor gene exhibit correct hematopoietic and neural expression", Proc. Assoc. Am. Physicians 108:449-454.

Mioni et al., 1992, "Evidence for specific binding and stimulatory effects of recombinant human erythropoietin on isolated adult rat Leydig cells", Acta Endocrinologica 127:459-465.

Okada et al., 1996, "Erythropoietin stimulates proliferation of rat-cultured gastric mucosal cells", Digestion 57:328-332.

Sawyer et al., 1989, "Receptors for erythropoietin in mouse and human erythroid cells and placenta", Blood 74:103-109.

Silva et al., 1999, "Erythropoietin can induce the expression of bcl-$x_L$ through Stat5 in erythropoietin-dependent progenitor cell lines", J. Biol. Chem. 274:22165-22169.

Sirén et al., 2001, "Erythropoietin prevents neuronal apoptosis after cerebral ischemia and metabolic stress", Proc. Natl. Acad. Sci. USA 98:4044-4049.

Westenfelder et al., 1999, "Human, rat and mouse kidney cells express functional erythropoietin receptors", Kidney Intl. 55:808-820.

Williams et al., 1994, "Human erythropoietin receptor", Ann. NY Acad. Sci. 718:232-244.

Satake et al. Chemical modification of erythropoietin: an increase in in vitro activity by guanidination. Biochim Biophys Acta. Mar. 29, 1990;1038(1):125-9.

Leist et. al., Derivatives of Erythropoietin that are Tissue Protective but not Erythropoietic, Science, 2004, 239-242, 305.

Bickel et al., 1994, In vivo demonstration of subcellular localization of anti-transferrin receptor monoclonal antibody-colloidal gold conjugate in brain capillary endothelium. J Histochem Cytochem. vol. 42(11):1493-7.

Boado et al., 1998, Drug delivery of antisense molecules to the brain for treatment of Alzheimer's disease and cerebral AIDS. J Pharm Sci. vol. 87(11):1308-15.

Boger and Goldberg, 2001, "Cytokine receptor dimerization and activation: prospects for small molecule agonists," Bioorg. & Med. Chem., 9:557-562.

Boissel et al., 1993 "Erythropoietin structure-function relationships," J. Biol. Chem. vol. 268(21):15983-15993.

Bonsi et al., 1997, "An erythroid and megakaryocytic common precursor cell line (B1647) expressing both c-mpl and erythropoietin receptor (Epo-R) proliferates and modifies globin chain synthesis in response to megakaryocyte growth and development factor (MGDF) but not to erythropoietin (Epo)," Br. J. Haematol. 98:549-559.

Pazur et al., 2000, "Oligosaccharides as immuno-determinants of erythropoietin for two sets of anti-carbohydrates antibodies," J. Protein Chem. vol. 19(8):631-635.

Takahashi, 1977, "The reactions of phenylglyoxal and related reagents with amino acids," J. Biochem., vol. 81:395-402.

Temple et al., 1995, "Recombinant erythropoietin improves cognitive function in patients maintained on chronic ambulatory peritoneal dialysis," Nephrology Dialysis Transplantation, vol. 10:1733-1738.

Wojchowski and Caslake, 1989, "Biotinylated recombinant human erythropoietins: bioactivity and utility as receptor ligands," Blood, vol. 74(3):952-958.

Agnello et al., 2002, "Erythropoietin exerts an anti-inflammatory effect on the CNS in a model of experimental autoimmune encephalomyelitis," Brain Research 952:128-134.

Akiitar et al., 1999, "Conformational study of N(epsilon)-(carboxymethyl)lysine adducts of recombinant alpha-crystallins," Current Eye Research 18:270-276.

Ando et al., 1996, "Autonomic dysfunction and anemia in neurologic disorders", J. Autonomic Nervous Syst. 61:145-148.

Ay et al., 1999, "Potential usefulness of basic fibroblast growth factor as a treatment for stroke," Cerebrovascular Disease 9:131-135.

Bany-Mohammed et al., 1996, "Recombinant human erythropoietin: possible role as an antioxidant in premature rabbits," Pediatric Res. 40(3):381-387.

Barber et al., 2001, "De novo design of cytokine-based alpha helical binding domains display cytotoxic activity," Blood 98(11, part 2):132b-133b Abstract 4193.

Barber et al., 1994, "Erythropoietin and interleukin-2 activate distinct JAK kinase family members," Mol. Cell. Biol. 14(10):6506-6514.

Barbone et al., 1997, "Mutagenesis studies of the human erythropoietin receptor. Establishment of structure-function relationships," J. Biol. Chem. 272(8):4985-4992.

Barron et al., 1994, "Alternatively spiced mRNAs encoding soluble isoforms of the erythropoietin receptor in murine cell lines and bone marrow," Gene 147:263-8.

Baskaya et al., 1997, "The biphasic opening of the blood—brain barrier in the cortex and hippocampus after traumatic brain injury in rats," Neuroscience Lett. 226:33-36.

Bazan, 1989, "A novel family of growth factor receptors: a common binding domain in the growth hormone, prolactin, erythropoietin and IL-6 receptors, and the p75 IL-2 receptor beta-chain," Biochem. Biophys. Res. Commun. 164(2):788-795.

Belayev et al., 1996, "Quantitative evaluation of blood-brain barrier permeability following middle cerebral artery occlusion in rats," Brain Research 739:88-96.

Benit et al., 1993, "The 'WS motif common to v-mpl and members of the cytokine receptor superfamily is dispensable for myeloproliferative leukemia virus pathogenicity," Oncogene 8:787-790.

Benjamin et al., 1998, "A plasticity window for blood vessel remodelling is defined by pericyte coverage of the preformed endothelial network and is regulated by PDGF-B and VEGF," Development 125:1591-1598.

Besarab et al., 1998, "The effects of normal as compared with low hematocrit values in patients with cardiac disease who are receiving hemodialysis and epoietin," New England Journal of Medicine 339(9):584-590.

Bickel et al., 1993, "Pharmacologic effects in vivo in brain by vector-mediated peptide drug delivery," Proc Natl Acad Sci USA 90:2618-22.

Boudot et al., 1999, "Erythropoietin induces glycosylphosphatidylinositol hydrolysis. Possible involvement of phospholipase c-gamma(2)," J. Biol. Chem. 274(48):33966-33972.

Brizzi et al., 1991, "Hematopoietic growth factor receptors," Int. J. Cell. Cloning 9:274-300.

Buemi et al., 2002, "Recombinant human erythropoietin influences revascularization and healing in a rat model of random ischaemic flaps," Acta Derm. Venerol. 82:411-417.

Bundgaard and Moller, 1981, "Horseradish peroxidase and microperoxidase. Their purity and binding to serum proteins," J. Histochem. Cytochem. 29(3):331-336.

Caravella et al., 1996, "A partial model of the erythropoietin receptor complex," Proteins 24:394-401.

Cerneus and Van Der Ende, 1991, "Apical and basolateral transferrin receptors in polarized BeWo cells recycle through separate endosomes," J Cell Biol. 114(6):1149-1158.

Chin et al., 2000, "Production and processing of erythropoietin receptor transcripts in brain," Mol. Brain Res. 81: 29-42.

Cunningham and Wells, 1989, "High-resolution epitope mapping of hGH-receptor interactions by alanine-scanning mutagenesis," Science 244:1081-1085.

D'Andrea and Gonda, 2000, "A model for assembly and activation of the GM-CSF, IL-3 and IL-5 receptors: insights from activated mutants of the common beta subunit," Exp. Hematol. 28(3):231-243.

D'Andrea et al., 1998, "Dysregulated hematopoiesis and a progressive neurological disorder induced by expression of an activated form of the human common beta chain in transgenic mice," J. Clin. Invest. 102(11):1951-1960.

D'Andrea and Zon, 1990, "Erythropoietin receptor. Subunit structure and activation," J. Clin. Invest. 86(3):681-687.

Dale et al., 2002, "Stimulated platelets use serotonin to enhance their retention of procoagulant proteins on the cell surface," Nature 415:175-179.

Dame et al., 2001, "The biology of erythropoietin in the central nervous system and its neurotrophic and neuroprotective potential," Biol. Neonate 79(3041:228-235.

Deguchi et al., 1999, "Retention of biologic activity of human epidermal growth factor following conjugation to a blood-brain barrier drug delivery vector via an extended poly(ethylene glycol) linker," Bioconjug Chem. 10(11:32-37.

Del Mastro and Venturi, 1998, "Strategies for the use of epoetin alfa in breast cancer patients," The Oncologist 3:314-318.

Denizot and Lang. 1986, "Rapid colorimetric assay for cell growth and survival - Modifications to the tetrazolium dye procedure giving improved sensitivity and reliability," J. Immunol, Meth. 89:271-277.

Diaz-Brinton and Yamazaki, 1998, "Advances and challenges in the prevention and treatment of Alzheimer's disease," Pharm. Res. 15(3):386-98.

Dietrich et al., 1993, "Microvascular and neuronal consequences of common carotid artery thrombosis and platelet embolization in rats," J. Neuropathol. Experimental Neurol. 52(4):351-360.

Dispersyn et al. 1999, Cardiomyocyte remodelling during myocardial hibernation and atrial fibrillation: prelude to apoptosis. Cardiovasc. Res. 43(4): 947-957.

Dobbin et al., 1989, "Transient blood-brain barrier permeability following profound temporary global ischaemia: An experimental study using $^{14}$C-AIB," J. of Cerebral Blood Flow Metabolism 9:71-78.

Dong et al., 1992, "Receptor binding of asialoerythropoietin," J. Cell. Biochem. 48(3):269-276.

Eckart, 2002, "Anaemia of critical illness—implications for understanding and treating rHuEPO resistance," Nephrol Dial Transplant 17, Suppl 5, pp. 48-55.

Egrie and Browne, 2001, "Development and characterization of novel erythropoiesis stimulating protein (NESP)," Nephrol. Dial. Transplant 16 (suppl. 3):3-13.

Elliott et al., 1997, "Mapping of the active site of recombinant human erythropoietin," Blood 89(2):493-502.

Feigin et al., 2002, "Recent advances in Huntington's disease: implications for experimental therapeutics," Curr. Opin. Neurol. 15(4):483-489.

Fishbein et al. 1981, "Early phase acute myocardial infarct size quantification: validation of the triphenyl tetrazolium chloride tissue enzyme staining technique," Am. Heart Journal 101(5): 593-600.

Foresta et al., 1994, "Erythropoietin stimulates testosterone production in man," J. Clin. Endocrinol. Metabol. 78(3):753-756.

Frank, 2002, "Minireview: Receptor dimerization in GH and erythropoietin action—it takes two to tango, but how?" Endocrinology 143(1):2-10.

Freshney, 1983, "Culture of animal cells," A Manual of Basic Technique, A R. Liss, Inc. NY 1983, pp. 3-4.

Friden, 1996, "Utilization of an endogenous cellular transport system for the delivery of therapeutics across the blood-brain barrier," J. Controlled Release 46:117-28.

Friedman et al., 1995, "Erythropoietin in diabetic macular edema and renal insufficiency," Am. J. Kidney Disease 26(1), pp. 202-208.

Fujita et al., 1997, "Role of alternative splicing of the rat erythropoietin receptor gene in normal and erythroleukemia cells," Leukemia, 11 (Suppl. 3): 444-445.

Fung and Greene, 1990, "The human interleukin-2 receptor: insights into subunit structure and growth signal transduction," Semin. Immunol. 2:119-128.

Gabriel et al., 1998, "High-dose recombinant human erythropoietin stimulates reticulocyte production in patients with multiple organ dysfunction syndrome," J. Trauma 44(2):361-367.

Gaertner et al., 1994, "Chemo-enzymic backbone engineering of proteins," J. Biol. Chem. 269(10):7224-7230.

Garcia et al., 1996, "Ischemic stroke and incomplete infarction," Stroke, vol. 27(4):761-765.

Goldberg et al., 2002, "Erythropoietin mimetics derived from solution phase combinatorial libraries." J. Amer. Chem Soc. 124(4):544-555.

Grasso ct al., 2006, "Amelioration of spinal cord compressive injury by pharmacological preconditioning with erythropoietin and a nonerythropoietic erythropoietin derivative," J. Neurosurg. Spine 4(4):310-318.

Green, 1998. "Clomethiazole (Zendra®) in acute ischemic stroke: Basic pharmacology and biochemistry and clinical efficacy," Pharmacol Then. 80(2):123-147.

Greenberg et al. 1995, "Congestive heart failure and sleep apnoea-possible mechanisms and effect of CPAP therapy," J. Sleep Res. 4(S1): 130-134.

Grimm et al., 2002. "HIF-1-induced erythropoietin in the hypoxic retina protects against light-induced retinal degeneration," Nature Medicine 8(7):718-724.

Grotzinger, 2002, "Molecular mechanisms of cytokine receptor activation," Biochim. Biophys. Acta. 1592:215-223.

Gruber et al., 2002, "The thrombin mutant W215A/E217A shows safe and potent anticoagulant and antithrombotic effects in vivo," J. Biol. Chem. 277(31):2758 I -27584.

Gunasekar et al., 2001, "Mechanisms of the apoptotic and necrotic actions of trimethyltin in cerebellar granule cells," Toxicological Sciences 64:83-89.

Hanazono et al., 1995, "Erythropoietin induces tyrosine phosphorylation of the beta chain of the GM-CSF receptor," Biochem. Biophys. Res. Comm. 208(3):1060-1066.

Hancher et al., 1974, "Recovery of Erythropoietin from Anemic Sheep Plasma," Biotechnology and Bioengineering 16:1069-1079.

Hansen, et al., 2000, "A randomized, blinded placebo controlled, phase II, dose-finding study of ARANESP in patients with lymphoproliferative malignances," Blood, vol. 96(11), pp. 155b, Abstr. 4371.

Harris et al. 1992, "Ligand binding properties of the human erythropoietin receptor extracellular domain expressed in *Escherichia coil*," J. Biol. Chem. 267(21):15205-15209.

Harris et al., 2000, "Purification and characterization of yeast-expressed erythropoietin (R103A), an erythropoietin antagonist," Blood 96(11, part 2):154b Abstract 4366.

Harris et al., 2001, "Characterization of the yeast-expressed erythropoietin mutant, EPO (R103A), a specific inhibitor of human primary heinatopoietic cell erythropoiesis," Blood, 98(11, part 1):77a Abstract 319.

Hassan and Freund, 1995, "Review of megakaryoblastic cell lines -Characteristic biological features of human megakaryoblastic leukaemia cell lines," Leuk. Res. 19(9):589-594.

Horkko et al., 1992, "Carbamylation-induced alterations in low-density lipoprotein metabolism," Kidney Int. 41(5):1175-1181.

Huwyler and Pardridge, 1998, "Examination of blood-brain barrier transferrin receptor by confocal fluorescent microscopy of unfixed isolated rat brain capillaries," J. Neurochem. 70(2):883-886.

Huwyler et al., 1997, "Receptor mediated delivery of daunomycin using immunoliposomes: pharmacokinetics and tissue distribution in the rat," J Pharmacol Exp Ther. 282(3):1541-1546.

Imada et al., 1992, "Interleukin-2 (IL-2) induces erythroid differentiation and tyrosine phosphorylation in ELM-I-1 cells transfected with a human IL-2 receptor beta chain cDNA," Biochem. Biophys. Res. Commun. 188(1):352-357.

Iseki et al., 1996, "Increased risk of cardiovascular disease with erythropoietin in chronic dialysis patients, " Nephron 72:30-36.

Itoh et al., 1990, "Cloning of an interleukin-3 receptor gene: a member of a distinct receptor gene family," Science 247:324-327.

Jacobs et al., 1985, "Isolation and characterization of genomic and cDNA clones of human erythropoietin," Nature 313(28):806-810.

Jenkins et al., 1999, "A cell type-specific constitutive point mutant of the common β-subunit of the human granulocyte-macrophage colony-stimulating factor (GM-CSF), interleukin (IL)-3, and IL-5 receptors requires the GM-CSF receptor α-subunit for activation," J. Biol. Chem. 274(13):8669-8677.

Jiang et al., 1996, "Delayed intravenous administration of basic fibroblast growth factor (bFGF) reduces infarct volume in a model of focal cerebral ischemia/reperfusion in the rat," J.Neurological Sciences 139.173-179.

Jones et al., 1990, "Human erythropoietin receptor: cloning, expression. And biologic characterization." Blood 76(1):31-35.

Jooss et al., 1996, "Cyclophosphamide diminishes inflammation and prolongs transgene expression following delivery of adenoviral vectors to mouse liver and lung," Hum. Gene Ther. 7(13):1555-1566.

Josse et al., 1999, "Human serum paraoxonase (PON1): Identification of essential amino acid residues by group-selective labelling and site-directed mutagenesis," Chem. Biol. Interact. 119-120:71-78.

Josse et al., 1999, "Tryptophan residue(s) as major components of the human serum paraoxonase active site," Chem. Biol. Interact. 119-120:79-84.

Jijbinsky et al., 1996, "The β c component of the granulocyte-macrophage colony-stimulating factor (GM-CSF)/interleukin 3 (IL-3)/IL-5 receptor interacts with a hybrid GM-CSF/erythropoietin receptor to influence proliferation and β-globin mRNA expression," Mol. Med. 2(6):766-773.

Jubinsky et al., 1997, "The β chain of the interleukin-3 receptor functionally associates with the erythropoietin receptor," Blood 90(5):1867-1873.

Juul, S. 2002, "Erythropoietin in the central nervous system, and its use to prevent hypoxic-ischemic brain damage," Acta Paediatr. Supp. 438:36-42.

Kang et al., 1994, "Pharmacokinetics and saturable blood-brain harrier transport of biotin bound to a conjugate of avidin and a monoclonal antibody to the transferrin receptor," Drug Metab. Dispos. 22(1):99-105.

Kawasaki et al., 2001, "Structural analysis of sulfated N-linked oligosaccharides in erythropoietin," Glycobiology 11(12):1043-1049.

Kirito et al., 2002, "Identification of the human erythropoietin receptor region required for Stat1 and Stat3 activation," Blood 99(I):102-110.

Kishimoto and Tavassoli, 1987, "Transendothelial transport (transcytosis) of iron-transferrin complex in the rat liver," Am. J. Anat. 178:241-249.

Kitajima et al., 1994, "Effective combination therapy by recombinant erythropoietin and cepharanthin in a girl with refractory anemia," Japanese J. Clin. Hematology, vol. 35(7):694-698 (w/English abstract).

Kitamura et al., 1989, "Identification and analysis of human erythropoietin receptors on a factor-dependent cell line, TF-1," Blood 73(2):375-80.

Krafte-Jacobs et al., 1996. "Circulating erythropoietin and interleukin-6 concentrations increase in critically ill children with sepsis and septic shock," Crit. Care Med. 24(9):1455-1459.

Kuroiwa et al., 1985, "The biphasic opening of the blood-brain barrier to proteins following temporary middle cerebral artery occlusion," Acta Neurophotalogica 68:122-129.

Lai et al., 1996, "The molecular role of the common gamma, subunit in signal transduction reveals functional asymmetry within multimeric cytokine receptor complexes." Proc. Natl. Acad. Sci. USA 93:231-235.

Lee et al. 1998, "Conditional lineage ablation to model human diseases," Proc. Natl. Acad. Sci. USA 95:11371-11376.

Leitgeb et al., 1994, "Quality of life in chronic anemia of cancer during treatment with recombinant human erythropoietin", Cancer; 73(10):2535-2542.

Lewis et al., 1996, "Molecular characterization of the 7q deletion in myeloid disorders." Br. J. Haematol. 93:75-80.

Linsley et al., 1994, "Applications of electrospray mass spectrometry to erythropoietin N- and O-linked glycans," Anal. Biochem. 219:207-217.

Liu et al., 1994, "Multiple cytokines stimulate the binding of a common 145-kilodalton protein to Shc at the Grb2 recognition site of Shc." Mol. Cell. Biol. 14(10):6926-6935.

Livnah et al., 1999, "Crystallographic evidence for preformed dimers of erythropoietin receptor before ligand activation," Science 283:987-990.

Loberg et al., 1993, "Neuronal uptake of plasma proteins after transient cerebral ischemia/hypoxia," APMIS 101:777-783.

Lundblad 1991, "The Modification of cystine—cleavage of disulfide bonds," Chemical Reagents for Protein Modification. $2^{nd}$ Edition CRC Press, Boca Raton Fl, pp. 95-98.

Magnanti et al., 2001, "Erythropoietin expression in primary rat Sertoli and peritubular myoid cells," Blood 98(9):2872-2874.

Maitani et al., 1996, "Oral administration of recombinant human erythropoietin in liposomes in rats: influence of lipid composition and size of liposomes on bioavailability". J. Phami. Sci.: 85(4):440-45 (Abstract only).

Massague, 1987, "The TGF-beta family of growth and differentiation factors," Cell 49:437-438.

Matthews et al., 1996, "A sequential dimerization mechanism for erythropoietin receptor activation," Proc. Natl. Acad. Sci. USA 93:9471-9476.

McClure et al., 2001, "GM-CSF binding to its receptor induces oligomerisation of the common beta-subunit," Cytokine 13(4):240-243.

Means and Krantz, 1996, "Inhibition of human erythroid colony-forming units by interferons $\alpha$ and $\beta$: differing mechanisms despite shared receptor," Exp. Hematol. 24:204-208.

Menzies and Ellis, 1990, Intestinal obstruction from adhesions—how big is the problem?, Ann. R. Coll. Surg. Engl. 72:60-63.

Menzies et al., 1990, "Extravasation of albumin in ischaemia brain oedema," Acta Neurochirurgica, Suppl. 51:220-222.

Mun and Golper, 2000, "Impaired biological activity of erythropoietin by cyanate carbamylation," Blood Purif. 18:13-17.

Murakami et al., 1991, "Critical cytoplasmic region of the interleukin 6 signal transducer gp130 is conserved in the cytokine receptor family," Proc. Natl. Acad. Sci. USA 88(24):11349-11353.

Murray, 1996, Harpers Illustrated Biochemistry $26^{th}$ ed. pp. 524-526, McGraw-Hill Co.

Nagao et al., 1992, "Production and ligand-binding characteristics of the soluble form of murine erythropoietin receptor," Biochem. Biophys. Res. Comm. 188(2):888-897.

Naranda et al., 2002, "Activation of erythropoietin receptor through a novel extracellular binding site," Endocrinology 143(6):2293-2302.

Nathan, 1994, "Studies of hybrid hematopoietic growth factor receptors," Stem Cells 12 (Suppl 1):27-35.

Nestler et al., 1985, "Stimulation of rat ovarian cell steroidogenesis by high density lipoproteins modified with tetranitromethane," J. Biol Chem. 260(12):7316-21.

Nimtz and Conradt, 1993, "Characterization of a phosphorylated oligosaccharide from erythropoeitin expressed in recombinant BHK cells," Glycoconj. J. 10(4):259, Abstr. S6.7.

Noguchi et al., 1991, "Cloning of the human erythropoietin receptor gene," Blood 78(10):2548-2556.

Ohta et al., 2001, "Selective glycopeptide mapping of erythropoietin by on-line high-performance liquid chromatography-electrospray ionization mass spectrometry," J. Chromatography A, 910:1-11.

Opitz et al. 1995, "Arrhythmias and Death After Coronary Artery Occlusion in the Rat," Circulation. 92(2):253-261.

Opitz et al. 1998, "Effects of reperfusion on arrhythmias and death after coronary artery occlusion in the rat: increased electrical stability independent of myocardial salvage," J. Am. Coll. Cardiol. 32(1): 261-267.

Page et al., 1996, "A sensitive human cell line based bioassay for megakaryocyte growth and development factor or thrombopoietin," Cytokine 8(1):66-69.

Pantoliano et al., 1987, "Protein engineering of subtilisin BPN': Enhanced stabilization through the introduction of two cysteines to form a disulfide bond," Biochemistry 26:2077-2082.

Pardridge, 1998, "CNS drug design based on principles of blood-brain barrier transport." J Neurochem. 70:1781-92.

Park and Hong, 1997, "Development of an in vitro bioassay system for human thrombopoietin by constructing a recombinant murine cell line expressing human thrombopoietin receptor," Mol. Cells. 7(6):699-704.

Pedersen et al., 1995, "The interaction of beta 2-microglobulin ($\beta$ 2m) with mouse class 1 major histocompatibility antigens and its ability to support peptide binding. A comparison of human and mouse beta 2m," Eur. J. Immunol. 25:1609-16.

Peng et al., 2000, "HPLC/ESI MS and MALDI/TOF MS analysis of microheterogeneity of the N-linked oligosaccharides of recombinant human erythropoietin," Yao Xue Bao (Acta Pharmaceutica Sinica) 35(10):770773 (w/ English abstract).

Penny and Forget, 1991, "Genomic organization of the human erythropoietin receptor gene," Genomics 11(4):974-980.

Petito, 1979, "Early and late mechanisms of increased vascular permeability following experimental cerebral infarction," J. Neuropatholo Exp. Neurol. 38(3):222-34.

Pfeffer et al., 1991, Progressive ventricular remodeling in rat with myocardial infarction. Am. J. Physiol. 260(5 Pt 2): H1406-1414.

Physicians' Desk Reference, 1995, $49^{th}$ Edition (Medical Economics Data Production Company, Montvale, NJ), pp. 1765-1769.

Physicians' Desk Reference, 2000 (Medical Economics Company, Inc. Montvale, NJ), pp. 519-525 and 2125-2131.

Pilbeam et al., 1993, "Comparison of the effects of various lengths of synthetic human parathyroid hormone-related peptide (hPTHrP) of malignancy on bone resorption and formation in organ culture," Bone 14:717-720.

Plapp et al., 1971, "Activity of bovine pancreatic deoxyribonuclease a with modified amino groups," J. Biol. Chem. 246(4):939-45.

Ponger et al., 1983, "Preparation of high-potency, non-aggregating insulins using a novel sulfation procedure," Diabetes 32:1087-1091.

Qui et al., 1998, "Homodimerization restores biological activity to an inactive erythropoietin mutant," J. Biol. Chem. 273(18):11173-11176.

Remy et al., 1999, "Erythropoietin receptor activation by a ligand-induced conformation change," Science 283:990-993.

Robinson et al., 1975, "Tetanus toxin. The effect of chemical modifications on toxicity, immunogenicity, and conformation," J. Biol. Chem. 250(18):7435-42.

Romanovsky et al., 1996, "First and second phases of biphasic fever: two sequential stages of the sickness syndrome?" Am. J. Physiol. 271(1 pt. 2):R244-R253.

Rosenbaum et al., 1997, "Retinal ischemia leads to apoptosis which is ameliorated by aurintricarboxylic acid," Vision Res., 37(24):3445-3451.

Rush et al., 1993, "Peptide mapping and evaluation of glycopeptide microheterogeneity derived from endoproteinase digestion of erythropoietin by affinity high-performance capillary electrophoresis," Anal. Chem. 65(14):1834-1842.

Rush et al., 1995, "Microheterogeneity of erythropoietin carbohydrate structure," Anal. Chemistry, 67(8):14421452.

Saito et al., 1990, "Role of neuroexcitation in development of blood-brain barrier and oedematous changes following cerebral ischaemia and traumatic brain injury," Acta Neurochirurgica, Suppl. 51:186-188.

Schiffl and Lang, 1997, "Hypertension induced by recombinant human erythropoietin (rHU-EPO) can be prevented by indomethacin. Pathogenetic role of cytosolic calcium," Eur J. Med. Res. 2:97-100.

Schussler et al., 1998, "Erythropoietin and obstetrical influences," Zeitschrift fur Geburtshilfe and Neonatologie 202(2):64-68 ( With English Abstract).

Scott et al., 2000. "Reassessment of interactions between hematopoietic receptors using common beta-chain and interleukin-3-specific receptor beta-chain-null cells: no evidence of functional interactions with receptors for erythropoietin, granulocyte colony-stimulating factor, or stem cell factor," Blood 96(4):1588-1590.

Shikama et al., 1996, "A constitutively activated chimeric cytokine receptor confers factor-independent growth in hematopoietic cell lines," Blood 88(2):455-464.

Shulman et al., 2002, "Current drug treatment of Sepsis," Hospital Pharmacist 9:97-107.

Soda et al., 1984, "Transendothelial transport (transcytosis) of iron-transferrin complex in the bone marrow," J Ultrastruct Res. 88(1):18-29.

Stark et al., 1960, "Reactions of the cyanate present in aqueous urea with amino acids and proteins," J. Biol. Chem. 235(11): 3177-3181.

Stark, 1967, "Modification of proteins with cyanate" Methods Enzymol. 11:590-594.

Steece-Collier et al., 2002, "Etiology of Parkinson's disease: Genetics and environment revisited," Proc. Natl. Acad. Sci. U. S. A. 99(22):13972-4.

Stenesh, J., 1989, Dictionary of Biochemistry and Molecular Biology, $2^{nd}$ Ed., New York, John Wiley & Sons, p. 122, p. 508.

Suzuki et al., 1983, "The effects of 5-minute ischemia in Mongolian gerbils: 1. Blood—brain barrier, cerebral blood flow, and local cerebral glucose utilization changes," Acta Neurophatologica (Berl) 60:207-216.

Sweeney et al., 1995, "Cellular mechanisms involved in brain ischemia," Can. J. Physiol. Pharmacol. vol. 73:1525-1535.

Syed et al., 1998, "Efficiency of signaling through cytokine receptors depends critically on receptor orientation," Nature 395:511-516.

Szabo et al., 1998, "Protection against peroxynitrite-induced fibroblast injury and arthritis development by inhibition of poly(ADP-ribose) synthase," Proc. Natl. Acad. Sci. USA 95:3867-3872.

Teien et al., 1995, Doppler evaluation of severity of mitral regurgitation: relation to pulmonary venous blood flow patterns in an animal study. J. Am. Coll. Cardiol. 25(1): 264-268.

Tojo et al., 1987, "Identification of erythropoietin receptors on fetal liver erythroid cells," Biochem. Biophys. Res. Commun. 148(1):443-448.

Urena, 2002, "Treatment of anemia in chronic renal failure by a long-active activator of erythropoiesis," Press Medicale 31(11):505-514 (w/ English abstract).

Vezzani et al., 1999, "Interleukin-1- β immunoreactivity and microglia are enhanced in the rat hippocampus by focal kainate application: Functional evidence for enhancement of electrographic seizures," J. Neurosci. 19(12):5054-65.

Vezzani et al., 1986, "Anticonvulsant drugs effective against human temporal lobe epilepsy prevent seizures but not neurotoxicity induced in rats by quinolinic acid: Electroencephalographic, behavioral and histological assessments," J. Pharmacol. Exp. Ther. 239(1):256-263.

Vukicevic et al., 1996, "Induction of nephrogenic mesenchyme by osteogenic protein 1 (bone morphogenetic protein 7)," PNAS USA 93:9021-9026.

Wauben-Penris et al., 1988, "The release of iron by Sertoli cells in culture," Biol. Reprod. 38:1105-1113.

Wells, 1990, "Additivity of mutational effects in proteins," Biochemistry 29(37):8509-8517.

Wen et al., 1994, "Erythropoietin structure-function relationships," J. Biol. Chem. 269(36):22839-22846.

Widness et al., 1995, "Erythropoietin transplacental passage-Review of animal studies," J. Perinat. Med. 23: 61-70.

Williamson et al., 1993, "Protein and lipid kinase activation cascades in interleukin-2 receptor signalling," Semin. Immunol. 5(5):337-344.

Winkelmann et al., 1990, "The gene for the human erythropoietin receptor: analysis of the coding sequence and assignment to chromosome 19p." Blood 76(1):24-30.

Wit et al., 1992, "Experimental models of ventricular tachycardia and fibrillation caused by ischemia and infarction," Circulation 85 Suppl. 1:I-32-I-42.

Wolf et al., 1997, "Erythropoietin administration increases production and reactivity of platelets in dogs," Thromb. Haemost. 78:1505-1509.

Wu and Pardridge, 1996, "Central nervous system pharmacologic effect in conscious rats after intravenous injection of a biotinylated vasoactive intestinal peptide analog coupled to a blood-brain barrier drug delivery system," J Pharmacol Exp Ther. 279(1):77-83.

Xiao et al., 1998, "Fibrinogen deficiency is compatible with the development of atherosclerosis in mice," J. Clin Invest. 101(5):1184-1194.

Yamamura et al., 1992, "Distinct downstream signaling mechanism between erythropoietin receptor and interleukin-2 receptor," EMBO J. 11(13):4909-4915.

Yang et al., 1994, "Reperfusion-induced injury to the blood-brain barrier after middle-cerebral artery occlusion in rats," Stroke, vol. 25(8):1658-1665.

Yang and Butler, 2002, "Effects of ammonia and glucosamine on the heterogeneity of erythropoietin glycoforms," Biotechnol. Prog. 18:129-38.

Yet et al., 1993, "The extracytoplasmic domain of the erythropoietin receptor forms a monomeric complex with erythropoietin," Blood 82(6):1713-1719.

Yoshimura et al., 1995, "A novel cytokine-inducible gene CIS encodes an SH2-containing protein that binds to tyrosine-phosphorylated interleukin 3 and erythropoietin receptors," EMBO J. 14(12):2816-2826.

Yoshimura et al., 1996, "Mouse oncostatin M: an immediate early gene induced by multiple cytokines through the JAK-STAT5 pathway," EMBO J. 15(5):1055-I063.

Yoshimura et al., 1996, "Physician Education: The Erythropoietin Receptor and Signal Transduction," Oncologist 1(5):337-339.

Zeng, 1991, "Lysine modification of metallothionein by carbamylation and guanidination," Methods Enzymol. 205:433-437.

Zhang et al., 2006, "Erythropoietin protects CA1 neurons against global cerebral ischemia in rat: potential signaling mechanisms," J. Neurosci. Res. 83:1241-51.

Zhu et al., 2002, "Detecting and responding to hypoxia," Nephrot. Dial. Transplant. 17 Suppl 1:3-7.

Lindahl J., 1980, "The contributions of erythropoietic and nonerythropoietic haem turnover to the early labelle peak of endogenous CO formation in man," Scand. J. Haematol. Apr. 24 (4): 271-80.

Trist, 2000, "Excitatory amino acid agonists and antagonists: pharmacology and therapeutic applications." Pharmaceutica Acta Helvetiae, vol. 74:221-229.

* cited by examiner

ELECTRORETINOGRAMS FROM RATS SUBJECTED TO 60 MINUTES OF ISCHEMIA  
BASELINE

ELECTRORETINOGRAMS FROM RATS SUBJECTED TO 60 MINUTES OF ISCHEMIA  
45 MIN ISCHEMIA

ELECTRORETINOGRAMS FROM RATS SUBJECTED TO 60 MINUTES OF ISCHEMIA  
SALINE @ 7 DAYS

ELECTRORETINOGRAMS FROM RATS SUBJECTED TO 60 MINUTES OF ISCHEMIA  
+ EPO @ 7 DAYS

PROTECTION, RESTORATION, AND ENHANCEMENT OF ERYTHROPOIETIN-RESPONSIVE CELLS, TISSUES AND ORGANS

This application claims the benefit of priority of PCT application no. PCT/US01/49479 filed Dec. 28, 2001 and provisional application No. 60/259,245 filed Dec. 29, 2000 under 35 U.S.C. § 119(e)(1), both of which are incorporated herein by reference in their entirety.

The instant application contains a Sequence Listing which has been submitted on two CD-Rs, and is hereby incorporated by reference in its entirety. Said CD-Rs, created on Jul. 18, 2006, are labeled "Sequence Listing Copy 1" and "Sequence Listing Copy 2." Each CD-R contains an identical 1 KB file identified as KW00-2A02-US seq.txt.

BACKGROUND OF THE INVENTION

For many years, the only clear physiological role of erythropoietin had been its control of the production of red blood cells. Recently, several lines of evidence suggest that erythropoietin, as a member of the cytokine superfamily, performs other important physiologic functions which are mediated through interaction with the erythropoietin receptor (erythropoietin-R). These actions include mitogenesis, modulation of calcium influx into smooth muscle cells and neural cells, and effects on intermediary metabolism. It is believed that erythropoietin provides compensatory responses that serve to improve hypoxic cellular microenvironment as well as modulate programmed cell death caused by metabolic stress. Although studies have established that erythropoietin injected intracranially protects neurons against hypoxic neuronal injury, intracranial administration is an impractical and unacceptable route of administration for therapeutic use, particularly for normal individuals. Furthermore, previous studies of anemic patients given erythropoietin have concluded that peripherally-administered erythropoietin is not transported into the brain (Marti et al., 1997, Kidney Int. 51:416-8; Juul et al., 1999, Pediatr. Res. 46:543-547; Buemi et al., 2000, Nephrol. Dial. Transplant. 15:422-433.).

Various modified forms of erythropoietin have been described with activities directed towards improving the erythropoietic activity of the molecule, such as those with altered amino acids at the carboxy terminus described in U.S. Pat. No. 5,457,089 and in U.S. Pat. No. 4,835,260; erythropoietin isoforms with various numbers of sialic acid residues per molecule, such as described in U.S. Pat. No. 5,856,298; polypeptides described in U.S. Pat. No. 4,703,008; agonists described in U.S. Pat. No. 5,767,078; peptides which bind to the erythropoietin receptor as described in U.S. Pat. Nos. 5,773,569 and 5,830,851; and small-molecule mimetics as described in U.S. Pat. No. 5,835,382.

It is towards the use of an erythropoietin for protecting, maintaining, enhancing, or restoring erythropoietin-responsive cells and associated cells, tissues and organs in situ as well as ex vivo, and to delivery of an erythropoietin across an endothelial cell barrier for the purpose of protecting and enhancing erythropoietin-responsive cells and associated cells, tissues and organs distal to the vasculature, or to carry associated molecules, that the present invention is directed.

BRIEF SUMMARY OF THE INVENTION

In one aspect, the present invention is directed to the use of erythropoietins for the preparation of pharmaceutical compositions for protecting, maintaining, enhancing, or restoring the function or viability of erythropoietin-responsive mammalian cells and their associated cells, tissues and organs. In one particular aspect, the erythropoietin-responsive mammalian cells and their associated cells, tissue or organ are distal to the vasculature by virtue of a tight endothelial cell barrier. In another particular aspect, the cells, tissues, organs or other bodily parts are isolated from a mammalian body, such as those intended for transplant. By way of non-limiting examples, the erythropoietin-responsive cell or tissue may be neuronal, retinal, muscle, heart, lung, liver, kidney, small intestine, adrenal cortex, adrenal medulla, capillary endothelial, testes, ovary, pancreas or endometrial cells or tissue. These examples of erythropoietin-responsive cells are merely illustrative. In one aspect, the erythropoietin-responsive cell or its associated cells, tissues, or organs are not excitable cells, tissues, or organs, or do not predominantly comprise excitable cells or tissues. In a particular embodiment, the mammalian cell, tissue or organ for which an aforementioned erythropoietin derivative is used are those that have expended or will expend a period of time under at least one condition adverse to the viability of the cell, tissue or organ. Such conditions include traumatic in-situ hypoxia or metabolic dysfunction, surgically-induced in-situ hypoxia or metabolic dysfunction, or in-situ toxin exposure, the latter may be associated with chemotherapy or radiation therapy. In one embodiment, the adverse conditions are a result of cardiopulmonary bypass (heart-lung machine), as is used for certain surgical procedures.

The erythropoietins are useful for the therapeutic or prophylactic treatment of human diseases of the CNS or peripheral nervous system which have primarily neurological or psychiatric symptoms, as well as ophthalmic diseases, cardiovascular diseases, cardiopulmonary diseases, respiratory diseases, kidney, urinary and reproductive diseases, gastrointestinal diseases and endocrine and metabolic abnormalities.

The invention is also directed to pharmaceutical compositions comprising particular erythropoietin derivatives for administration to a mammalian animal, preferably a human. Such pharmaceutical compositions may be formulated for oral, intranasal, or parenteral administration, or in the form of a perfusate solution for maintaining the viability of cells, tissues or organs ex vivo.

Erythropoietin derivatives useful for the aforementioned purposes may be any native erythropoietin, or an erythropoietin analog, an erythropoietin mimetic, and erythropoietin fragment, a hybrid erythropoietin molecule, an erythropoietin-receptor-binding molecule, an erythropoietin agonist, a renal erythropoietin, a brain erythropoietin, an oligomer thereof, a multimer thereof, a mutein thereof, a congener thereof, a naturally-occurring form thereof, a synthetic form thereof, a recombinant form thereof, a glycosylation variant thereof, a deglycosylated variant thereof, or a combination thereof. Any form of erythropoietin capable of benefiting erythropoietin-responsive cells is embraced in this aspect of the invention.

Other erythropoietin derivatives useful for the aforementioned purposes and pharmaceutical compositions include both native erythropoietins as well as erythropoietins that have been altered by at least one modification as compared to native erythropoietin, and preferably as compared to native human erythropoietin. The at least one modification may be a modification of at least one amino acid of the erythropoietin molecule, or a modification of at least one carbohydrate of the erythropoietin molecule. Of course, erythropoietin molecules useful for the purposes herein may have a plurality of modifications compared to the native molecule, such as multiple modifications of the amino acid portion of the molecule, multiple modifications of the carbohydrate portion of the molecule, or at least one modification of the amino acid portion of the molecule and at least one modification of the carbohydrate portion of the molecule. The modified erythropoietin molecule retains its ability of protecting, maintaining, enhancing or restoring the function or viability of erythropoietin-responsive mammalian cells, yet other properties of the erythropoietin molecule unrelated to the aforementioned, desirable feature may be absent as compared to the native molecule. In a preferred embodiment, the erythropoietin derivative is non-erythropoietic.

In one embodiment, the erythropoietin of the invention has at least no sialic acid moieties. In a preferred embodiment, the modified erythropoietin is asialoerythropoietin, and most preferably, human asialoerythropoietin. In another embodiment, the modified erythropoietin has 1, 2, 3, 4, 5, 6, 7, 8, 9, 10, 11, 12, or 13 sialic acid moieties.

In a second embodiment, the modified erythropoietin has at least no N-linked or no O-linked carbohydrates.

In a third embodiment, the modified erythropoietin has at least a reduced carbohydrate content by virtue of treatment of erythropoietin with its native carbohydrates with at least one glycosidase.

In a fourth embodiment, the carbohydrate portion of the modified erythropoietin molecule has at least a non-mammalian glycosylation pattern by virtue of the expression of a recombinant erythropoietin in non-mammalian cells. In preferred embodiments, the modified erythropoietins are expressed in insect cells or plant cells.

In a fifth embodiment, the modified erythropoietin has at least one or more oxidized carbohydrates which also may be chemically reduced. In a preferred embodiment, the modified erythropoietin is periodate-oxidized erythropoietin; in another preferred embodiment, the periodate-oxidized erythropoietin is chemically reduced with a borohydride salt such as sodium borohydride or sodium cyanoborohydride.

In a sixth embodiment, the modified erythropoietin for the aforementioned uses has at least one or more modified arginine residues. In one embodiment, the modified erythropoietin comprises a glyoxal moiety on the one or more arginine residues, such as an arylglyoxal or alkylglyoxal moiety. In another embodiment, at least one arginine residue is modified by reaction with a vicinal diketone such as but not limited to 2,3-butanedione or cyclohexanedione.

In a seventh embodiment, the modified erythropoietin comprises at least one or more modified lysine residues or a modification of the N-terminal amino group of the erythropoietin molecule, such modifications as those resulting from reaction of the lysine residue or N-terminal amino group with an amino-group-modifying agent. The modified lysine residue further may be chemically reduced. In one preferred embodiment, an erythropoietin is biotinylated or carbamylated via one or more lysine groups. In another preferred embodiment, the lysine is reacted with an aldehyde or reducing sugar to form an imine, which may be stabilized by reduction as with sodium cyanoborohydride to form an N-alkylated lysine such as glucitolyl lysine, or which in the case of reducing sugars may be stabilized by Amadori or Heyns rearrangement to form an alpha-deoxy alpha-amino sugar such as alpha-deoxy-alpha-fructosyllysine. In another preferred embodiment, the lysine group is carbamylated (carbamoylated), such as by virtue of reaction with cyanate ion, alkyl-carbamylated, aryl-carbamylated, or aryl-thiocarbamylated with an alkyl-isocyanate, aryl-isocyanate, or aryl-isothiocyanate, respectively, or it may be acylated by a reactive alkylcarboxylic or arylcarboxylic acid derivative, such as by reaction with acetic anhydride, succinic anhydride or phthalic anhydride. At least one lysine group may also be trinitrophenyl modified by reaction with a trinitrobenzenesulfonic acid, or preferably its salts. In another embodiment, lysine residues may be modified by reaction with a glyoxal derivative, such as reaction with glyoxal; methylglyoxal or 3-deoxyglucosone to form the corresponding alpha-carboxyalkyl derivatives.

In an eighth embodiment, at least one tyrosine residue of erythropoietin may be modified in an aromatic ring position by an electrophilic reagent, such as by nitration or iodination.

In a ninth embodiment, at least an aspartic acid or a glutamic acid residue of an erythropoietin may be modified, such as by reaction with a carbodiimide followed by reaction with an amine such as but not limited to glycinamide.

In a tenth embodiment, at least a tryptophan residue of an erythropoietin is modified, such as by reaction with n-bromosuccinimide or n-chlorosuccinimide.

In an eleventh embodiment, a modified erythropoietin molecule is provided having at least one erythropoietin amino group removed, such as by reaction with ninhydrin followed by reduction of the resulting carbonyl group by reaction with borohydride.

In a twelfth embodiment, a modified erythropoietin is provided having at least an opening of at least one of the cystine linkages in the erythropoietin molecule by reaction with a reducing agent such as dithiothreitol, followed by reaction of the subsequent sulfhydryls with iodoacetamide, iodoacetic acid or another electrophile to prevent reformation of the disulfide linkages.

In a thirteenth embodiment, a modified erythropoietin is provided having at least one substitution of any one of a number of amino acids, such as a leucine, with at least one of lysine, arginine, tryptophan, tyrosine, or cysteine residues of erythropoietin, using molecular biological techniques.

In a fourteenth embodiment, a modified erythropoietin is subjected to a limited chemical proteolysis that targets specific residues, for example, to cleave after tryptophan residues. Such resulting erythropoietin fragments are embraced herein.

As noted above, an erythropoietin useful for the purposes herein may have at least one of the aforementioned modifications, but may have more than one of the above modifications. By way of example of a modified erythropoietin with one modification to the carbohydrate portion of the molecule and one modification to the amino acid portion, a modified erythropoietin is asialoerythropoietin and has its lysine residues biotinylated or carbamylated. The present invention also embraces compositions, including pharmaceutical compositions, comprising one or more of the aforementioned erythropoietins.

In another aspect of the invention, a method is provided for the protecting, maintaining, enhancing or restoring the function or viability of erythropoietin-responsive mammalian cells and their associated cells, tissues and organs, by administering an effective amount of any one or more of the aforementioned erythropoietins. In one particular aspect of the method, the erythropoietin-responsive mammalian cells and their associated cells, tissue or organ are distal to the vasculature by virtue of a tight endothelial cell barrier. In another particular aspect, the cells, tissues, organs or other bodily parts are isolated from a mammalian body, such as those intended for transplant. By way of non-limiting examples, the erythropoietin-responsive cell or tissue may be neuronal, retinal, muscle, heart, lung, liver, kidney, small intestine, adrenal cortex, adrenal medulla, capillary endothelial, testes, ovary, or endometrial cells or tissue. These examples of erythropoietin-responsive cells are merely illustrative. In a particular embodiment, the erythropoietin-responsive cell or its associated cells, tissues, or organs are not excitable cells, tissues, or organs, or do not predominantly comprise excitable cells or tissues. In another particular embodiment, the mammalian cell, tissue or organ for which an aforementioned erythropoietin derivative may be administered are those that have expended or will expend a period of time under at least one condition adverse to the viability of the cell, tissue or organ. Such conditions may include traumatic in-situ hypoxia or metabolic dysfunction, surgically-induced in-situ hypoxia or metabolic dysfunction, or in-situ toxin exposure, the latter may be associated with chemotherapy or radiation therapy. In one embodiment, the invention protects against the adverse conditions resulting from cardiopulmonary bypass.

In another aspect of the invention, any of the foregoing erythropoietins as well as any other erythropoietin molecules including native human erythropoietin can be used in the preparation of a pharmaceutical composition for ex-vivo treatment of cells, tissues and organs for the purpose of protecting, maintaining, enhancing, or restoring the function or viability of erythropoietin-responsive mammalian cells and their associated cells, tissues and organs. Such ex-vivo treatment is useful, for example, for the preservation of cells, tissues or organs for transplant, whether autotransplant or xenotransplant. The cells, tissue or organ may be bathed in a solution comprising erythropoietin, or the perfusate instilled into the organ through the vasculature or other means, to maintain cellular functioning during the period wherein the cells, tissue or organ is not integrated with the vasculature of the donor or recipient. Administration of the perfusate may be made to a donor prior to organ harvesting, as well as to the harvested organ and to the recipient. Moreover, the aforementioned use of any erythropoietin is useful whenever a cell, tissue or organ is isolated from the vasculature of the individual and thus essentially existing ex vivo for a period of time, the term isolated referring to restricting or clamping the vasculature of or to the cell, tissue, organ or bodily part, such as may be performed during surgery, including, in particular, cardiopulmonary bypass surgery; bypassing the vasculature of the cell, tissue, organ or bodily part; removing the cell, tissue, organ or bodily part from the mammalian body, such may be done in advance of xenotransplantation or prior to and during autotransplantation; or traumatic amputation of a cell, tissue, organ or bodily part. Thus, this aspect of the invention pertains both to the perfusion with an erythropoietin in situ and ex vivo. Ex vivo, the erythropoietin may be provided in a cell, tissue or organ preservation solution. For either aspect, the exposing may be by way of continuous perfusion, pulsatile perfusion, infusion, bathing, injection, or catheterization.

In yet a further aspect, the invention is directed to a method for protecting, maintaining, enhancing, or restoring the viability of a mammalian cell, tissue, organ or bodily part which includes an erythropoietin-responsive cell or tissue, in which the cell, tissue, organ or bodily part is isolated from the mammalian body. The method includes at least exposing the isolated mammalian cell, tissue, organ or bodily part to an amount of an erythropoietin for a duration which is effective to protect, maintain, enhance, or restore the aforesaid viability. In non-limiting examples, isolated refers to restricting or clamping the vasculature of or to the cell, tissue, organ or bodily part, such as may be performed during surgery, in particular, cardiopulmonary bypass surgery; bypassing the vasculature of the cell, tissue, organ or bodily part; removing the cell, tissue, organ or bodily part from the mammalian body, such may be done in advance of xenotransplantation or prior to and during autotransplantation; or traumatic amputation of a cell, tissue, organ or bodily part. Thus, this aspect of the invention pertains both to the perfusion with an erythropoietin in situ and ex vivo. Ex vivo, the erythropoietin may be provided in a cell, tissue or organ preservation solution. For either aspect, the exposing may be by way of continuous perfusion, pulsatile perfusion, infusion, bathing, injection, or catheterization.

In the aforementioned isolation or ex-vivo embodiment, a useful erythropoietin may be any of the aforementioned erythropoietins, including any native erythropoietin, or an erythropoietin analog, an erythropoietin mimetic, and erythropoietin fragment, a hybrid erythropoietin molecule, an erythropoietin-receptor-binding molecule, an erythropoietin agonist, a renal erythropoietin, a brain erythropoietin, an oligomer thereof, a multimer thereof, a mutein thereof, a congener thereof, a naturally-occurring form thereof, a synthetic form thereof, a recombinant form thereof, a glycosylation variant thereof, a deglycosylated variant thereof, or a combination thereof Any form of erythropoietin capable of benefitting erythropoietin-responsive cells is embraced in this aspect of the invention. Other erythropoietins include, but are not limited to asialoerythropoietin, N-deglycosylated erythropoietin, O-deglycosylated erythropoietin, erythropoietin with reduced carbohydrate content, erythropoietin with altered glycosylation patterns, erythropoietin with carbohydrates oxidized then reduced, arylglyoxal-modified erythropoietin, alkylglyoxal-modified erythropoietin, 2,3-butanedione-modified erythropoietin, cyclohexanedione-modified erythropoietin, biotinylated erythropoietin, N-alkylated-lysyl-erythropoietin, glucitolyl lysine erythropoietin, alpha-deoxy-alpha-fructosyllysine-erythropoietin, carbamylated erythropoietin, acetylated erythropoietin, succinylated erythropoietin, alpha-carboxyalkyl erythropoietin, nitrated erythropoietin, iodinated erythropoietin, to name some representative yet non-limiting examples based on the teachings herein. A human erythropoietin is preferred; native human erythropoietin is most preferred. In another embodiment human asialoerythropoietin is preferred. In another embodiment human phenylglyoxal erythropoietin is preferred.

By way of non-limiting examples, the aforementioned ex-vivo erythropoietin-responsive cell or tissue may be or comprise neuronal, retinal, muscle, heart, lung, liver, kidney, small intestine, adrenal cortex, adrenal medulla, capillary endothelial, testes, ovary, or endometrial cells or tissue. These examples of erythropoietin-responsive cells are merely illustrative.

All of the foregoing methods and uses are preferably applicable to human beings, but are useful as well for any mammal, such as but not limited to companion animals, domesticated animals, livestock and zoo animals. Routes of administration of the aforementioned pharmaceutical compositions include oral, intravenous, intranasal, topical, intraluminal, inhalation or parenteral administration, the latter including intravenous, intraarterial, subcutaneous, intramuscular, intraperitoneal, submucosal or intradermal. For ex-vivo use, a perfusate or bath solution is preferred. This includes pervusing an isolated portion of the vasculature in situ.

In yet another aspect of the invention, any of the aforementioned erythropoietins are useful in preparing a pharmaceutical composition for restoring a dysfunctional cell, tissue or organ when administered after the onset of the disease or condition responsible for the dysfunction. By way of non-limiting example, administration of a pharmaceutical composition comprising erythropoietin restores cognitive function in animals previously having brain trauma, even when administered long after (e.g., three days, five days, a week, a month, or longer) the trauma has subsided. Erythropoietins useful for such applications include any of the particular aforementioned erythropoietins or any native erythropoietin, or an erythropoietin analog, an erythropoietin mimetic, and erythropoietin fragment, a hybrid erythropoietin molecule, an erythropoietin-receptor-binding molecule, an erythropoietin agonist, a renal erythropoietin, a brain erythropoietin, an oligomer thereof, a multimer thereof, a mutein thereof, a congener thereof, a naturally-occurring form thereof, a synthetic form thereof, a recombinant form thereof, a glycosylation variant thereof, a deglycosylated variant thereof, or a combination thereof. Any form of erythropoietin capable of benefitting erythropoietin-responsive cells is embraced in this aspect of the invention. Other erythropoietin derivatives useful for the aforementioned purposes and pharmaceutical compositions include both native erythropoietins as well as erythropoietins that have been altered by at least one modification as compared to native erythropoietin, and preferably as compared to native human erythropoietin. The at least one modification may be a modification of at least one amino acid of the erythropoietin molecule, or a modification of at least one carbohydrate of the erythropoietin molecule. Of course, erythropoietin molecules useful for the purposes herein may have a plurality of modifications compared to the native molecule, such as multiple modifications of the amino acid portion of the molecule, multiple modifications of the carbohydrate portion of the molecule, or at least one modification of the amino acid portion of the molecule and at least one modification of the carbohydrate portion of the molecule. The modified erythropoietin molecule retains its ability of protecting, maintaining, enhancing or restoring the function or viability of erythropoietin-responsive mammalian cells, yet other properties of the erythropoietin molecule unrelated to the aforementioned, desirable feature may be absent as compared to the native molecule. A human erythropoietin is preferred; native human erythropoietin is most preferred. In another embodiment human asialoerythropoietin is preferred.

In yet another embodiment, the invention provides methods for the use of the aforementioned erythropoietin for restoring a dysfunctional cell, tissue or organ when administered after the onset of the disease or condition responsible for the dysfunction. By way of non-limiting example, methods for administration of a pharmaceutical composition comprising erythropoietin restores cognitive function in animals previously having brain trauma, even when administered long after (e.g., three days, five days, a week, a month, or longer) the trauma has subsided. Erythropoietins useful for such methods include any of the particular aforementioned erythropoietins or any native erythropoietin, or an erythropoietin analog, an erythropoietin mimetic, and erythropoietin fragment, a hybrid erythropoietin molecule, an erythropoietin-receptor-binding molecule, an erythropoietin agonist, a renal erythropoietin, a brain erythropoietin, an oligomer thereof, a multimer thereof, a mutein thereof, a congener thereof, a naturally-occurring form thereof, a synthetic form thereof, a recombinant form thereof, a glycosylation variant thereof, a deglycosylated variant thereof, or a combination thereof. Any form of erythropoietin capable of benefitting erythropoietin-responsive cells is embraced in this aspect of the invention. Other erythropoietin derivatives useful for the aforementioned purposes and pharmaceutical compositions include both native erythropoietins as well as erythropoietins that have been altered by at least one modification as compared to native erythropoietin, and preferably as compared to native human erythropoietin. The at least one modification may be a modification of at least one amino acid of the erythropoietin molecule, or a modification of at least one carbohydrate of the erythropoietin molecule. Of course, erythropoietin molecules useful for the purposes herein may have a plurality of modifications compared to the native molecule, such as multiple modifications of the amino acid portion of the molecule, multiple modifications of the carbohydrate portion of the molecule, or at least one modification of the amino acid portion of the molecule and at least one modification of the carbohydrate portion of the molecule. The modified erythropoietin molecule retains its ability of protecting, maintaining, enhancing or restoring the function or viability of erythropoietin-responsive mammalian cells, yet other properties of the erythropoietin molecule unrelated to the aforementioned, desirable feature may be absent as compared to the native molecule. A human erythropoietin is preferred; native human erythropoietin is most preferred. In another embodiment human asialoerythropoietin is preferred.

In still yet a further aspect of the present invention, methods are provided for facilitating the transcytosis of a molecule across an endothelial cell barrier in a mammal by administration a composition of a molecule in association with an erythropoietin such as: an erythropoietin having at least no sialic acid moieties; an erythropoietin having at least no N-linked or no O-linked carbohydrates; an erythropoietin having at least a reduced carbohydrate content by virtue of treatment of native erythropoietin with at least one glycosidase; an erythropoietin with a carbohydrate portion of the erythropoietin molecule having at least a non-mammalian glycosylation pattern by virtue of the expression of a recombinant erythropoietin in non-mammalian cells; an erythropoietin has at least one or more oxidized carbohydrates which also may be chemically reduced; an erythropoietin having at least one or more modified arginine residues; an erythropoietin having at least one or more modified lysine residues or a modification of the N-terminal amino group of the erythropoietin molecule; an erythropoietin having at least a modified tyrosine residue; an erythropoietin having at least a modified aspartic acid or a glutamic acid residue; an erythropoietin having at least a modified tryptophan residue; an erythropoietin having at least one amino group removed; an erythropoietin having at least an opening of at least one of the cystine linkages in the erythropoietin molecule; an erythropoietin is provided having at least one substitution of at least one amino acid; or a truncated erythropoietin.

The association between the molecule to be transported and the erythropoietin may be, for example, a labile covalent bond, a stable covalent bond, or a noncovalent association with a binding site for the molecule. Endothelial cell barriers may be the blood-brain barrier, the blood-eye barrier, the blood-testes barrier, the blood-ovary barrier and the blood-placenta barrier. Suitable molecule for transport by the method of the present invention include hormones, such as growth hormone, antibiotics and anti-cancer agents.

It is a further aspect of the present invention to provide a composition for facilitating the transcytosis of a molecule across an endothelial cell barrier in a mammal, said composition comprising said molecule in association with an erythropoietin such as an erythropoietin having at least no sialic acid moieties; an erythropoietin having at least no N-linked or no O-linked carbohydrates; an erythropoietin having at least a reduced carbohydrate content by virtue of treatment of native erythropoietin with at least one glycosidase; an erythropoietin with a carbohydrate portion of the modified erythropoietin molecule having at least a non-mammalian glycosylation pattern by virtue of the expression of a recombinant erythropoietin in non-mammalian cells; an erythropoietin has at least one or more oxidized carbohydrates which also may be chemically reduced; an erythropoietin having at least one or more modified arginine residues; an erythropoietin having at least one or more modified lysine residues or a modification of the N-terminal amino group of the erythropoietin molecule; an erythropoietin having at least a modified tyrosine residue; an erythropoietin having at least a modified aspartic acid or a glutamic acid residue; an erythropoietin having at least a modified tryptophan residue; an erythropoietin having at least one amino group removed; an erythropoietin having at least an opening of at least one of the cystine linkages in the erythropoietin molecule; an erythropoietin is provided having at least one substitution of at least one amino acid; or a truncated erythropoietin.

The association may be, for example, a labile covalent bond, a stable covalent bond, or a noncovalent association with a binding site for the molecule. Endothelial cell barriers may be the blood-brain barrier, the blood-eye barrier, the blood-testes barrier, the blood-ovary barrier and the blood-placenta barrier. Suitable molecule for transport by the method of the present invention include hormones, such as growth hormone, antibiotics and anti-cancer agents.

In a still further aspect of the present invention, any of the aforementioned erythropoietins are useful in preparing a pharmaceutical composition for facilitating the transcytosis of a molecule across an endothelial cell barrier in a mammal, said composition comprising said molecule in association with an erythropoietin such as an erythropoietin having at least no sialic acid moieties; an erythropoietin having at least no N-linked or no O-linked carbohydrates; an erythropoietin having at least a reduced carbohydrate content by virtue of treatment of native erythropoietin with at least one glycosidase; an erythropoietin with a carbohydrate portion of the modified erythropoietin molecule having at least a non-mammalian glycosylation pattern by virtue of the expression of a recombinant erythropoietin in non-mammalian cells; an erythropoietin has at least one or more oxidized carbohydrates which also may be chemically reduced; an erythropoietin having at least one or more modified arginine residues; an erythropoietin having at least one or more modified lysine residues or a modification of the N-terminal amino group of the erythropoietin molecule; an erythropoietin having at least a modified tyrosine residue; an erythropoietin having at least a modified aspartic acid or a glutamic acid residue; an erythropoietin having at least a modified tryptophan residue; an erythropoietin having at least one amino group removed; an erythropoietin having at least an opening of at least one of the cystine linkages in the erythropoietin molecule; an erythropoietin is provided having at least one substitution of at least one amino acid; or a truncated erythropoietin.

The association may be, for example, a labile covalent bond, a stable covalent bond, or a noncovalent association with a binding site for the molecule. Endothelial cell barriers may be the blood-brain barrier, the blood-eye barrier, the blood-testes barrier, the blood-ovary barrier and the blood-placenta barrier. Suitable molecule for transport by the method of the present invention include hormones, such as growth hormone, antibiotics and anti-cancer agents.

These and other aspects of the present invention will be better appreciated by reference to the following Figures and Detailed Description.

DETAILED DESCRIPTION OF THE INVENTION

Figure 1:
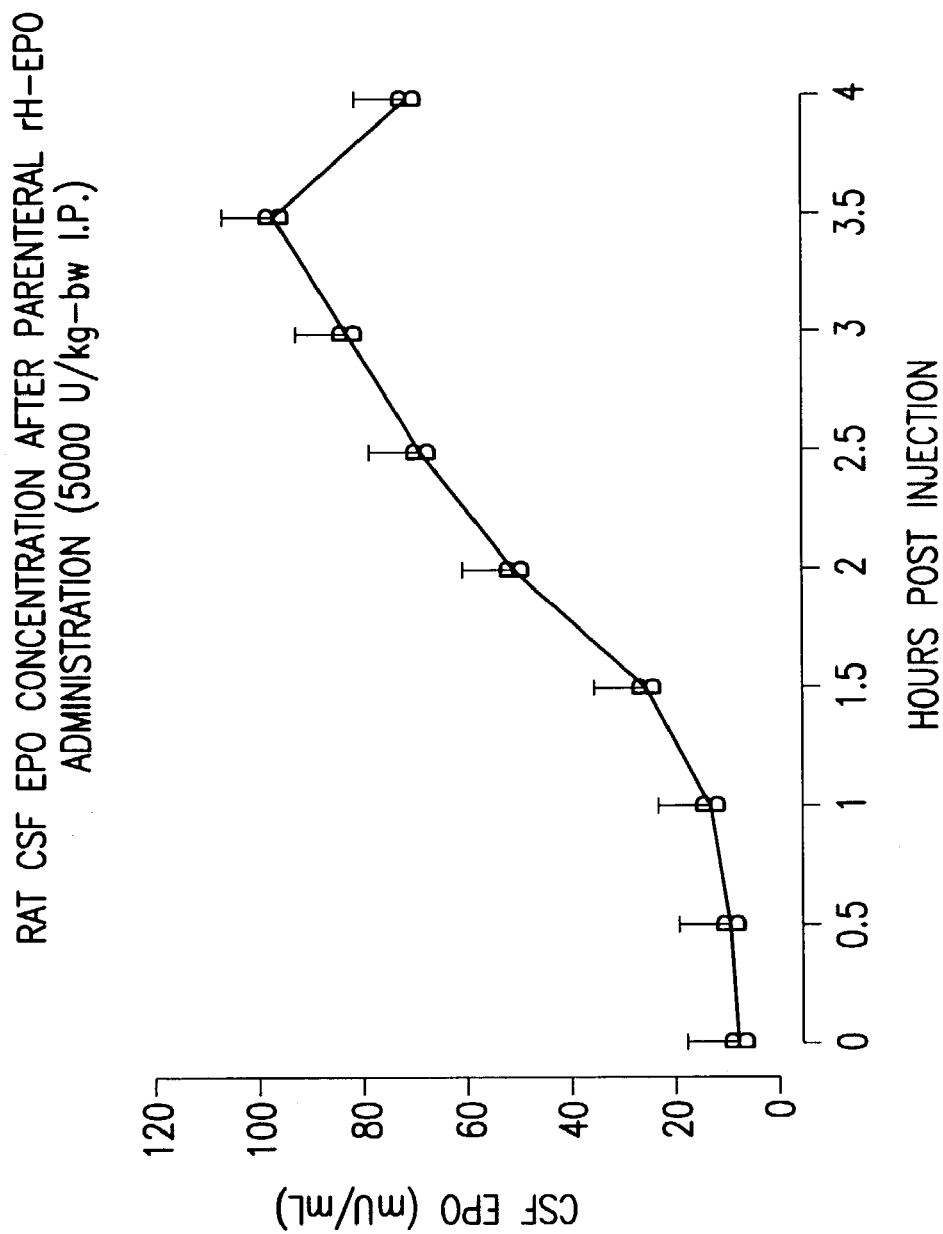
FIG. 1 depicts the translocation of parenterally-administered erythropoietin into the cerebrospinal fluid.

"Erythropoietin-responsive cell" refers to a mammalian cell whose function or viability may be maintained, promoted, enhanced, regenerated, or in any other way benefitted, by exposure to an erythropoietin. Non-limiting examples of such cells include neuronal, retinal, muscle, heart, lung, liver, kidney, small intestine, adrenal cortex, adrenal medulla, capillary endothelial, testes, ovary, and endometrial cells. Moreover, such erythropoietin-responsive cells and the benefits provided thereto by an erythropoietin may be extended to provide protection or enhancement indirectly to other cells that are not directly erythropoietin responsive, or of tissues or organs which contain such non-erythropoietin-responsive cells. These other cells, or tissues or organs which benefit indirectly from the enhancement of erythropoietin-responsive cells present as part of the cells, tissue or organ as "associated" cells, tissues and organs. Thus, benefits of an erythropoietin as described herein may be provided as a result of the presence of a small number or proportion of erythropoietin-responsive cells in a tissue or organ, for example, excitable or neuronal tissue present in such tissue, or the Leydig cells of the testis, which makes testosterone. In one aspect, the erythropoietin-responsive cell or its associated cells, tissues, or organs are not excitable cells, tissues, or organs, or do not predominantly comprise excitable cells or tissues.

The methods of the invention provide for the local or systemic protection or enhancement of cells, tissues and organs within a mammalian body, under a wide variety of normal and adverse conditions, or protection of those which are destined for relocation to another mammalian body. In addition, restoration or regeneration of dysfunction is also provided. As mentioned above, the ability of an erythropoietin to cross a tight endothelial cell barrier and exert its positive effects on erythropoietin-responsive cells (as well as other types of cells) distal to the vasculature offers the potential to prevent as well as treat a wide variety of conditions and diseases which otherwise cause significant cellular and tissue damage in an animal, including human, and moreover, permit success of heretofore unattemptable surgical procedures for which risk traditionally outweighed the benefits. The duration and degree of purposeful adverse conditions induced for ultimate benefit, such as high-dose chemotherapy, radiation therapy, prolonged ex-vivo transplant survival, and prolonged periods of surgically-induced ischemia, may be carried out by taking advantage of the invention herein. However, the invention is not so limited, but includes as one aspect, methods or compositions wherein the target erythropoietin-responsive cells are distal to the vasculature by virtue of an endothelial-cell barrier or endothelial tight junctions. In general, the invention is directed to any erythropoietin-responsive cells and associated cells, tissues and organs which may benefit from exposure to an erythropoietin. Furthermore, cellular, tissue or organ dysfunction may be restored or regenerated after an acute adverse event (such as trauma) by exposure to an erythropoietin.

The invention is therefore directed generally to the use of erythropoietins for the preparation of pharmaceutical compositions for the aforementioned purposes in which cellular function is maintained, promoted, enhanced, regenerated, or in any other way benefitted. The invention is also directed to methods for maintaining, enhancing, promoting, or regenerating cellular function by administering to a mammal an effective amount of an erythropoietin as described herein. The invention is further directed to methods for maintaining, promoting, enhancing, or regenerating cellular function ex vivo by exposing cells, a tissue or organ to an erythropoietin. The invention is also directed to a perfusate composition comprising an erythropoietin for use in organ or tissue preservation.

The various methods of the invention utilize a pharmaceutical composition which at least includes an erythropoietin at an effective amount for the particular route and duration of exposure to exert positive effects or benefits on erythropoietin-responsive cells within or removed from a mammalian body. Where the target cell, tissues or organs of the intended therapy require the erythropoietin to cross an endothelial cell barrier, the pharmaceutical composition includes the erythropoietin at a concentration which is capable, after crossing the endothelial cell barrier, of exerting its desirable effects upon the erythropoietin-responsive cells. Molecules capable of interacting with the erythropoietin receptor and modulating the activity of the receptor, herein referred to as erythropoietin or erythropoietin receptor activity modulators, are useful in the context of the present invention. These molecules may be, for example, naturally-occurring, synthetic, or recombinant forms of erythropoietin molecules, as described above, or other molecules which may not necessarily resemble erythropoietin in any manner, except to modulate erythropoietin responsive cell activity, as described herein.

Erythropoietin is a glycoprotein hormone which in humans has a molecular weight of about 34 kDa. The mature protein comprises 165 amino acids, and the glycosyl residues comprise about 40% of the weight of the molecule. The forms of erythropoietin useful in the practice of the present invention encompass naturally-occurring, synthetic and recombinant forms of the following human and other mammalian erythropoietin-related molecules: erythropoietin, asialoerythropoietin, deglycosylated erythropoietin, erythropoietin analogs, erythropoietin mimetics, erythropoietin fragments, hybrid erythropoietin molecules, erythropoietin receptor-binding molecules, erythropoietin agonists, renal erythropoietin, brain erythropoietin, oligomers and multimers thereof, muteins thereof, and congeners thereof. In addition, erythropoietin forms useful in the practice of the present invention include proteins that represent functionally equivalent gene products. Such an equivalent erythropoietin gene product include mutant erythropoietins, which may contain deletions, including internal deletions, additions, including additions yielding fusion proteins, or conservative substitutions of amino acid residues within and/or adjacent to the amino acid sequence, but that result in a "silent" change, in that the change produces a functionally equivalent erythropoietin. Such amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid. Alternatively, non-conservative amino acid changes, and larger insertions and deletions may be used to create functionally altered erythropoietin mutants. Such mutants can be used to alter erythropoietin properties in desirable ways.

For example, in one embodiment an erythropoietin useful for the practice of the invention can be a mutant erythropoietin altered in one or more amino acids within the four functional domains of erythropoietin which affect receptor binding: VLQRY (SEQ ID NO: 1) and/or TKVNFYAW (SEQ ID NO: 2) and/or SGLRSLTTL (SEQ ID NO: 3) and/or SNFLRG SEQ ID NO: 4).

In another embodiment, erythropoietins containing mutations in the surrounding areas of the molecule which affect the kinetics or receptor-binding properties of the molecule can be used.

The term "erythropoietin" as well as "an erythropoietin" may be used interchangeably or conjunctively, and the various analogs, fragments, hybrid molecules, agonists, muteins, and other forms as described above embrace the variants in the extents of and sites of glycosylation of erythropoietin, including native, deglycosylated, asialylated, and other partially glycosylated forms of erythropoietin. Non-limiting examples of such variants are described in Tsuda et al., 1990, *Eur. J. Biochem.* 188:405-411, incorporated herein by reference. Bacteria, yeast, insect, plant, mammalian, including human. In addition, a variety of host systems may be used for expression and production of recombinant erythropoietin, including, but not limited to, bacteria, yeast, insect, plant, and mammalian, including human, cell systems. For example, recombinant erythropoietin produced in bacteria, which do not glycosylate or sialate the product, could be used to produce non-glycosylated forms of erythropoietin. Alternatively, recombinant erythropoietin can produced in other systems that do glycosylate, e.g., plants, including human cells.

As noted above, the invention herein embraces any and all erythropoietin receptor activity modulator molecules capable of exerting positive activity on erythropoietin-responsive cells, regardless of any structural relationship of the molecule with erythropoietin.

In addition, erythropoietin itself may be modified to tailor its activities for a specific tissue or tissues. Several non-limiting strategies which may be carried out to achieve this desired tissue specificity include modifications that shorten circulating half-life and thus reducing the time erythropoietin can interact with erythroid precursors, or modification of the primary structure of the erythropoietin molecule. One approach to reducing circulating half life is to remove or modify the glycosylation moieties, of which erythropoietin has three N-linked and one O-linked. Such variants of glycosylated erythropoietin can be produced in a number of ways. For example, the sialic acids which terminate the end of the sugar chains can be removed by specific sialidases depending on the chemical linkage connecting the sialic acid to the sugar chain. Alternatively, the glycosylated structure can be dismantled in different ways by using other enzymes that cleave at specific linkages. Techniques to modify the primary structure are myriad and include substitution of specific amino acids, chemical modification of amino acids, or addition of other structures which interfere with the interaction of erythropoietin with any of its receptors. Use of such forms of erythropoietin are filly embraced herein. In a preferred embodiment, the half-life of the non-erythropoietic erythropoietin of the invention is reduced by about 90% from that of native erythropoietin.

Some of these molecules will nevertheless mimic the actions of erythropoietin itself in other tissues or organs. For example, a 17-mer containing the amino-acid sequence of 31-47 of native erythropoietin is inactive for erythropoiesis but fully active for neural cells in vitro (Campana & O'Brien, 1998: Int. J. Mol. Med. 1:235-41).

Furthermore, derivative erythropoietin molecules desirable for the uses described herein may be generated by guanidination, amidination, carbamylation (carbamoylation), trinitrophenylation, acetylation, succinylation, nitration, or modification of arginine, lysine, tyrosine, tryptophan, or cysteine residues or carboxyl groups, among other procedures, such as limited proteolysis, removal of amino groups, and/or mutational substitution of arginine, lysine, tyrosine, tryptophan, or cysteine residues by molecular biological techniques to produce erythropoietins which maintain an adequate level of activities for specific organs and tissues but not for others, such as erythrocytes (e.g., Satake et al; 1990, Biochim. Biophys. Acta 1038:125-9; incorporated herein by reference in its entirety), in which in vivo biological activity was determined by the polycythemic mouse bioassay (Cotes, P. M. and Bangham, D. R. (1961) Nature 191, 1065-1067. One non-limiting example as described hereinbelow is the modification of erythropoietin arginine residues by reaction with a glyoxal such as phenylglyoxal (according to the protocol of Takahashi, 1977, J. Biochem. 81:395-402). As will be seen below, such an erythropoietin molecule fully retains its neurotrophic effect. Such erythropoietin molecules are fully embraced for the various uses and compositions described herein.

Synthetic and recombinant molecules, such as brain erythropoietin and renal erythropoietin, recombinant mammalian forms of erythropoietin, as well as its naturally-occurring, tumor-derived, and recombinant isoforms, such as recombinantly-expressed molecules and those prepared by homologous recombination are provided herein. Furthermore, the present invention includes molecules including peptides which bind the erythropoietin receptor, as well as recombinant constructs or other molecules which possess part or all of the structural and/or biological properties of erythropoietin, including fragments and multimers of erythropoietin or its fragments. Erythropoietin herein embraces molecules with altered erythropoietin receptor binding activities, preferably with increased receptor affinity, in particular as pertains to enhancing transport across endothelial cell barriers. Muteins comprising molecules which have additional or reduced numbers of glycosylation sites are included herein. As noted above, the terms "erythropoietin" and "mimetics" as well as the other terms are used interchangeably herein to refer to the erythropoietin-responsive cell protective and enhancing molecules related to erythropoietin as well as the molecules which are capable of crossing endothelial cell barriers.

Furthermore, molecules produced by transgenic animals are also encompassed here. It should be noted that erythropoietin molecules as embraced herein do not necessarily resemble erythropoietin structurally or in any other manner, except for ability to interact with the erythropoietin receptor or modulate erythropoietin receptor activity or activate erythropoietin-activated signaling cascades, as described herein.

By way of non-limiting examples, forms of erythropoietin useful for the practice of the present invention include erythropoietin muteins, such as those with altered amino acids at the carboxy terminus described in U.S. Pat. No. 5,457,089 and in U.S. Pat. No. 4,835,260; asialoerythropoietin and erythropoietin isoforms with various numbers of sialic acid residues per molecule, such as described in U.S. Pat. No. 5,856,298; polypeptides described in U.S. Pat. No. 4,703,008; agonists described in U.S. Pat. No. 5,767,078; peptides which bind to the erythropoietin receptor as described in U.S. Pat. Nos. 5,773,569 and 5,830,851; small-molecule mimetics which activate the erythropoietin receptor, as described in U.S. Pat. No. 5,835,382; and erythropoietin analogs described in WO 9505465, WO 9718318, and WO 9818926. All of the aforementioned citations are incorporated herein to the extent that such disclosures refer to the various alternate forms or processes for preparing such forms of the erythropoietins of the present invention.

Erythropoietin can be obtained commercially, for example, under the trademarks of PROCRIT, available from Ortho Biotech Inc., Raritan, N.J., and EPOGEN, available from Amgen, Inc., Thousand Oaks, Calif.

The activity (in units) of erythropoietin (erythropoietin) and erythropoietin-like molecules is traditionally defined based on its effectiveness in stimulating red cell production in rodent models (and as derived by international standards of erythropoietin). One unit (U) of regular erythropoietin (MW of ~34,000) is ~8 ng of protein (1 mg protein is approximately 125,000 U). However, as the effect on erythropoiesis is incidental to the desired activities herein and may not necessarily be a detectable property of certain of the erythropoietins of the invention, the definition of activity based on erythropoietic activity is inappropriate. Thus, as used herein, the activity unit of erythropoietin or erythropoietin-related molecules is defined as the amount of protein required to elicit the same activity in neural or other erythropoietin-responsive cellular systems as is elicited by WHO international standard erythropoietin in the same system. The skilled artisan will readily determine the units of a non-erythropoietic erythropoietin or related molecule following the guidance herein.

Further to the above-mentioned erythropoietin modifications useful herein, the following discussion expands on the various erythropoietins of the invention.

An erythropoietin of the invention may have at least no sialic acid moieties, referred to as asialoerythropoietin. Preferably, an erythropoietin of the invention is human asialoerythropoietin. In alternative embodiments, the erythropoietin of the invention may have at least 1, 2, 3, 4, 5, 6, 7, 8, 9, 10, 11, 12, or 13 sialic acid residues. It may be prepared by desialylating erythropoietin using a sialidase, such as is described in the manufacturer's packaging for Sialydase A from ProZyme Inc., San Leandro, Calif. Typically, PROZYME® GLYCOPRO® sequencing-grade SIALYDASE AT™ (N-acetylneuraminate glycohydrolase, EC 3.2.1.18) is used to cleave all non-reducing terminal sialic acid residues from complex carbohydrates and glycoproteins such as erythropoietin. It will also cleave branched sialic acids (linked to an internal residue). Sialydase A is isolated from a clone of *Arthrobacter ureafaciens*.

An erythropoietin may have at least a reduced number of N-linked carbohydrates. To remove N-linked carbohydrates, erythropoietin may be treated with hydrazine, in accordance, for example, with the methods described by Hermentin et al., 1996, Glycobiology 6(2):217-30. As noted above, erythropoietin has three N-linked carbohydrate moieties; the present invention embraces those erythropoietins with two, one, or no N-linked carbohydrate.

An erythropoietin of the invention may have at least a reduced carbohydrate content by virtue of treatment of native erythropoietin with at least one glycosidase. For example, the procedure of Chen and Evangelista, 1998, Electrophoresis 19(15):2639-44, may be followed. Furthermore, removal of the O-linked carbohydrate may be achieved following the methods described in Hokke et al., 1995, Eur. J. Biochem. 228(3):981-1008.

The carbohydrate portion of an erythropoietin molecule may have at least a non-mammalian glycosylation pattern by virtue of the expression of a recombinant erythropoietin in non-mammalian cells. Preferably, the erythropoietins are expressed in insect or plant cells. By way of non-limiting example, expression of erythropoietin in insect cells using a baculovirus expression system may be carried out in accordance with Quelle et al., 1989, Blood 74(2):652-657. Another method is described in U.S. Pat. No. 5,637,477. Expression in a plant system may be carried out in accordance with the method of Matsumoto et al., 1993, Biosci. Biotech. Biochem. 57(8):1249-1252. Alternatively, expression in bacteria will result in non-glycosylated forms of erythropoietin. These are merely exemplary of methods useful for the production of an erythropoietin of the invention are in no way limiting.

An erythropoietin of the invention may have at least one or more oxidized carbohydrates that also may be chemically reduced. For example, the erythropoietin may be periodate-oxidized erythropoietin; the periodate-oxidized erythropoietin also may be chemically reduced with a borohydride salt such as sodium borohydride or sodium cyanoborohydride. Periodate oxidation of erythropoietin may be carried out, for example, by the methods described by Linsley et al., 1994, Anal. Biochem.219(2):207-17. Chemical reduction following periodate oxidation may be carried out following the methods of Tonelli and Meints, 1978, J. Supramol. Struct. 8(1):67-78.

An erythropoietin for the aforementioned uses may have at least one or more modified arginine residues. For example, the modified erythropoietin may comprise a R-glyoxal moiety on the one or more arginine residues, where R may be an aryl, heteroaryl, lower alkyl, lower alkoxy, or cycloalkyl group, or an alpha-deoxyglycitolyl group. As used herein, the term lower "alkyl" means a straight- or branched-chain saturated aliphatic hydrocarbon group preferably containing 1-6 carbon atoms. Representative of such groups are methyl, ethyl, isopropyl, isobutyl, butyl, pentyl, hexyl and the like. The term "alkoxy" means a lower alkyl group as defined above attached to the remainder of the molecule by oxygen. Examples of alkoxy include methoxy, ethoxy, propoxy, isopropoxy and the like. The term "cycloalkyl" refers to cyclic alkyl groups with three up to about 8 carbons, including for example cyclopropyl, cyclobutyl, cyclohexyl and the like. The term aryl refers to phenyl and naphthyl groups. The term heteroaryl refers to heterocyclic groups containing 4-10 ring members and 1-3 heteroatoms selected from the group consisting of oxygen, nitrogen and sulfur. Examples include but are not limited to isoxazolyl, phenylisoxazolyl, furyl, pyrimidinyl, quinolyl, tetrahydroquinolyl, pyridyl, imidazolyl, pyrrolidinyl, 1,2,4-triazoylyl, thiazolyl, thienyl, and the like. The R group may be substituted, as for example the 2,3,4-trihydroxybutyl group of 3-deoxyglucosone. Typical examples of R-glyoxal compounds are glyoxal, methylglyoxal, 3-deoxyglucosone, and phenylglyoxal. Preferred R-glyoxal compounds are methylglyoxal or phenylglyoxal. An exemplary method for such modification may be found in Werber et al., 1975, Isr. J. Med. Sci. 11(11): 1169-70, using phenylglyoxal.

In a further example, at least one arginine residue may be modified by reaction with a vicinal diketone such as 2,3-butanedione or cyclohexanedione, preferably in ca. 50 millimolar borate buffer at pH 8-9. A procedure for the latter modification with 2,3-butanedione may be carried out in accordance with Riordan, 1973, Biochemistry 12(20): 3915-3923; and that with cyclohexanone according to Patthy et al., 1975, J. Biol. Chem 250(2): 565-9.

An erythropoietin of the invention may comprise at least one or more modified lysine residues or a modification of the N-terminal amino group of the erythropoietin molecule, such modifications as those resulting from reaction of the lysine residue with an amino-group-modifying agent. In another embodiment, lysine residues may be modified by reaction with glyoxal derivatives, such as reaction with glyoxal, methylglyoxal and 3-deoxyglucosone to form alpha-carboxyalkyl derivatives. Examples are reaction with glyoxal to form carboxymethyllysine as in Glomb and Monnier, 1995, J. Biol. Chem. 270(17):10017-26, or with methylglyoxal to form (1-carboxyethyl)lysine as in Degenhardt et al., 1998, Cell. Mol. Biol. (Noisy-le-grand) 44(7):1139-45. The modified lysine residue further may be chemically reduced. For example, the erythropoietin may be biotinylated via lysine groups, such as in accordance with the method described in Example 5, in which D-biotinoyl-ε-aminocaproic acid-N-hydroxysuccinimide ester was reacted with erythropoietin, followed by removal of unreacted biotin by gel filtration on a Centricon 10 column, as described by Wojchowski and Caslake, 1989, Blood 74(3):952-8. In this paper, the authors use three different methods of biotinylating erythropoietin, any of which may be used for the preparation of the erythropoietins for the uses herein. Biotin may be added to (1) the sialic acid moieties (2) carboxylate groups or (3) amino groups.

In another preferred embodiment, the lysine may be reacted with an aldehyde or reducing sugar to form an imine, which may be stabilized by reduction as with sodium cyanoborohydride to form an N-alkylated lysine such as glucitolyl lysine, or which in the case of reducing sugars may be stabilized by Amadori or Heyns rearrangement to form an alpha-deoxy alpha-amino sugar such as alpha-deoxy-alpha-fructosyllysine. As an example, preparation of a fructosyllysine-modified protein by incubation with 0.5 M glucose in sodium phosphate buffer at pH 7.4 for 60 days is described by Makita et al., 1992, J. Biol. Chem. 267:5133-5138. In another example, the lysine group may be carbamylated, such as by virtue of reaction with cyanate ion, or alkyl- or aryl-carbamylated or -thiocarbamylated with an alkyl- or aryl-isocyanate or -isothiocyanate, or it may be acylated by a reactive alkyl- or arylcarboxylic acid derivative, such as by reaction with acetic anhydride or succinic anhydride or phthalic anhydride. Exemplary are the modification of lysine groups with 4-sulfophenylisothiocyanate or with acetic anhydride, both as described in Gao et al., 1994, Proc Natl Acad Sci USA 91(25): 12027-30. Lysine groups may also be trinitrophenyl modified by reaction with trinitrobenzenesulfonic acid or preferably its salts. Such methods are described below in Example 5.

At least one tyrosine residue of an erythropoietin may be modified in an aromatic ring position by an electrophilic reagent, such as by nitration or iodination. By way of non-limiting example, erythropoietin may be reacted with tetranitromethane (Nestler et al., 1985, J. Biol. Chem. 260(12): 7316-21; or iodinated as described in Example 5.

At least an aspartic acid or a glutamic acid residue of an erythropoietin may be modified, such as by reaction with a carbodiimide followed by reaction with an amine such as but not limited to glycinamide. Examples of such modifications may be found in Example 5.

In another example, a tryptophan residue of an erythropoietin may be modified, such as by reaction with n-bromosuccinimide or n-chlorosuccinimide, following methods such as described in Josse et al., Chem Biol Interact May 14, 1999; 119-120.

In yet another example, an erythropoietin molecule may be prepared by removing at least one amino group, such may be achieved by reaction with ninhydrin followed by reduction of the subsequent carbonyl group by reaction with borohydride.

In still a further example, an erythropoietin is provided that has at least an opening of at least one of the cystine linkages in the erythropoietin molecule by reaction with a reducing agent such as dithiothreitol, followed by reaction of the subsequent sulhydryls with iodoacetamide, iodoacetic acid or another electrophile to prevent reformation of the disulfide linkages.

An erythropoietin is provided having at least one substitution of any one of a number of amino acids, such as a leucine, with at least one of lysine, arginine, tryptophan, tyrosine, or cysteine residues of erythropoietin, using molecular biological techniques.

A modified erythropoietin may be prepared by subjecting an erythropoietin to a limited chemical proteolysis that targets specific residues, for example, to cleave after tryptophan residues. Such resulting erythropoietin fragments are embraced herein.

As noted above, an erythropoietin useful for the purposes herein may have at least one of the aforementioned modifications, but may have more than one of the above modifications. By way of example of a modified erythropoietin with one modification to the carbohydrate portion of the molecule and one modification to the amino acid portion, a modified erythropoietin may be asialoerythropoietin and have its lysine residues biotinylated or carbamylated.

Thus, various erythropoietin molecules and pharmaceutical compositions containing them for the uses described herein are embraced. Such erythropoietin molecules include but are not limited to asialoerythropoietin, N-deglycosylated erythropoietin, O-deglycosylated erythropoietin, erythropoietin with reduced carbohydrate content, erythropoietin with altered glycosylation patterns, erythropoietin with carbohydrates oxidized then reduced, arylglyoxal-modified erythropoietin, alkylglyoxal-modified erythropoietin, 2,3-butanedione-modified erythropoietin, cyclohexanedione-modified erythropoietin, biotinylated erythropoietin, N-alkylated-lysyl-erythropoietin, glucitolyl lysine erythropoietin, alpha-deoxy-alpha-fructosyllysine-erythropoietin, carbamylated erythropoietin, acetylated erythropoietin, succinylated erythropoietin, alpha-carboxyalkyl erythropoietin, nitrated erythropoietin, iodinated erythropoietin, to name some representative yet non-limiting examples based on the teachings herein. Preferred are the aforementioned modified forms based on human erythropoietin.

Moreover, certain of the aforementioned erythropoietins are new, and the invention is directed to such compounds as well as pharmaceutical compositions comprising them. By way of non-limiting example, such new erythropoietins include periodate-oxidized erythropoietin, glucitolyl lysine erythropoietin, fructosyl lysine erythropoietin, 3-deoxyglucosone erythropoietin, and carbamylated asialoerythropoietin.

A variety of host-expression vector systems may be utilized to produce the erythropoietins and erythropoietin-related molecules of the invention. Such host-expression systems represent vehicles by which the erythropoietins of interest may be produced and subsequently purified, but also represent cells that may, when transformed or transfected with the appropriate nucleotide coding sequences, exhibit the modified erythropoietin gene product in situ. These include but are not limited to, bacteria, insect, plant, mammalian, including human host systems, such as, but not limited to, insect cell systems infected with recombinant virus expression vectors (e.g., baculovirus) containing the modified erythropoietin product coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing erythropoietin-related molecule coding sequences; or mammalian cell systems, including human cell systems, (e.g., HT1080, COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter).

In addition, a host cell strain may be chosen that modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells that possess the cellular machinery for proper processing of the primary transcript, glycosylation, and phosphorylation of the gene product may be used. Such mammalian host cells, including human host cells, include but are not limited to HT1080, CHO, VERO, BHK, HeLa, COS, MDCK, 293, 3T3, and WI38.

For long-term, high-yield production of recombinant proteins, stable expression is preferred. For example, cell lines that stably express the erythropoietin-related molecule gene product may be engineered. Rather than using expression vectors that contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci that in turn can be cloned and expanded into cell lines. This method may advantageously be used to engineer cell lines that express the erythropoietin-related molecule gene product. Such engineered cell lines may be particularly useful in screening and evaluation of compounds that affect the endogenous activity of the erythropoietin-related molecule gene product.

Alternatively, the expression characteristic of an endogenous erythropoietin gene within a cell line or microorganism may be modified by inserting a heterologous DNA regulatory element into the genome of a stable cell line or cloned microorganism such that the inserted regulatory element is operatively linked with the endogenous erythropoietin gene. For example, an endogenous erythropoietin gene which is normally "transcriptionally silent", i.e., an erythropoietin gene which is normally not expressed, or is expressed only a very low levels in a cell line, may be activated by inserting a regulatory element which is capable of promoting the expression of a normally expressed gene product in that cell line or microorganism. Alternatively, a transcriptionally silent, endogenous erythropoietin gene may be activated by insertion of a promiscuous regulatory element that works across cell types.

A heterologous regulatory element may be inserted into a stable cell line or cloned microorganism, such it is operatively linked with an endogenous erythropoietin gene, using techniques, such as targeted homologous recombination, which are well known to those of skill in the art, and described e.g., in French Patent No. 2646438 to Institut Pasteur, U.S. Pat. No. 4,215,051 to Chappel; U.S. Pat. No. 5,578,461 to Sherwin et al.; International Application No. PCT/US92/09627 (WO93/09222) by Selden et al.; and International Application No. PCT/US90/06436 (WO91/06667) by Skoultchi et al., each of which is incorporated by reference herein in its entirety.

In one embodiment of the invention, an erythropoietin-related molecule deficient in sialic residues, or completely lacking sialic residues, may be produced in mammalian cell, including a human cell. Such cells may be engineered to be deficient in, or lacking, the enzymes that add sialic acids, i.e., the β-galactoside α 2,3 sialyltransferase ("α 2,3 sialyltransferase") and the β-galactoside α 2,6 sialyltransferase ("α 2,6 sialyltransferase") activity. In one embodiment, a mammalian cell is used in which either or both the α 2,3 sialyltransferase gene and/or the α 2,6 sialyltransferase gene, is deleted. Such deletions may be constructed using gene knock-out techniques well known in the art. In another embodiment, dihydrofolate reductase (DHFR) deficient Chinese Hamster Ovary (CHO) cells are used as the host cell for the production of recombinant erythropoietin-related molecules. CHO cells do not express the enzyme α 2,6 sialyltransferase and therefore do not add sialic acid in the 2,6 linkage to N-linked oligosaccharides of glycoproteins produced in these cells. As a result, recombinant proteins produced in CHO cells lack sialic acid in the 2,6 linkage to galactose (Sasaki et al. (1987; Takeuchi et al. supra; Mutsaers et al Eur. J. Biochem. 156, 651 (1986); Takeuchi et al. J. Chromotgr. 400, 207 (1987). In one embodiment, to produce a host cell for the production of asialo-erythropoietin, the gene encoding α 2,3 sialyltransferase in CHO cells is deleted. Such α 2,3 sialyltransferase knock-out CHO cells completely lack sialyltransferase activity, and as a result, are useful for the recombinant expression and production of asialo-erythropoietin.

In another embodiment, asialo glycoproteins can be produced by interfering with sialic acid transport into the golgi apparatus e.g., Eckhardt et al., 1998, J. Biol. Chem. 273: 20189-95). Using methods well known to those skilled in the art (e.g., Oelmann et al., 2001, J. Biol. Chem. 276:26291-300), mutagenesis of the nucleotide sugar CMP-sialic acid transporter can be accomplished to produce mutants of Chinese hamster ovary cells. These cells cannot add sialic acid residues to glycoproteins such as erthropoietin and produce only asialoerythropoietin. Transfected mammalian cells producing erythropoietin also produce cytosolic sialidase which if it leaks into the culture medium degrades sialoerythropoietin with high efficiency (e.g., Gramer et al, 1995 Biotechnology 13:692-698). Using methods well known to those knowledgeable in the art (e.g., from information provided in Ferrari et al, 1994, Glycobiology 4:367-373), cell lines can be transfected, mutated or otherwise caused to constitutively produce sialidase. In this manner, asialoerythropoietin can be produced during the manufacture of asialoerythropoietin.

In the practice of one aspect of the present invention, a pharmaceutical composition as described above containing an erythropoietin may be administerable to a mammal by any route which provides a sufficient level of an erythropoietin in the vasculature to permit translocation across an endothelial cell barrier and beneficial effects on erythropoietin-responsive cells. When used for the purpose of perfusing a tissue or organ, similar results are desired. In the instance wherein the erythropoietin is used for ex-vivo perfusion, the erythropoietin may be any form of erythropoietin, such as the aforementioned erythropoietins but not limited thereto an may be inclusive of native erythropoietins including human erythropoietin. In the instance where the cells or tissue is non-vascularized and/or the administration is by bathing the cells or tissue with the composition of the invention, the pharmaceutical composition provides an effective erythropoietin-responsive-cell-beneficial amount of an erythropoietin. The endothelial cell barriers across which an erythropoietin may translocate include tight junctions, perforated junctions, fenestrated junctions, and any other types of endothelial barriers present in a mammal. A preferred barrier is an endothelial cell tight junction, but the invention is not so limiting.

The aforementioned erythropoietins are useful generally for the therapeutic or prophylactic treatment of human diseases of the central nervous system or peripheral nervous system which have primarily neurological or psychiatric symptoms, ophthalmic diseases, cardiovascular diseases, cardiopulmonary diseases, respiratory diseases, kidney, urinary and reproductive diseases, gastrointestinal diseases and endocrine and metabolic abnormalities. In particular, such conditions and diseases include hypoxic conditions, which adversely affect excitable tissues, such as excitable tissues in the central nervous system tissue, peripheral nervous system tissue, or cardiac tissue or retinal tissue such as, for example, brain, heart, or retina/eye. Therefore, the invention can be used to treat or prevent damage to excitable tissue resulting from hypoxic conditions in a variety of conditions and circumstances. Non-limiting examples of such conditions and circumstances are provided in the table hereinbelow.

In the example of the protection of neuronal tissue pathologies treatable in accordance with the present invention, such pathologies include those which result from reduced oxygenation of neuronal tissues. Any condition which reduces the availability of oxygen to neuronal tissue, resulting in stress, damage, and finally, neuronal cell death, can be treated by the methods of the present invention. Generally referred to as hypoxia and/or ischemia, these conditions arise from or include, but are not limited to stroke, vascular occlusion, prenatal or postnatal oxygen deprivation, suffocation, choking, near drowning, carbon monoxide poisoning, smoke inhalation, trauma, including surgery and radiotherapy, asphyxia, epilepsy, hypoglycemia, chronic obstructive pulmonary disease, emphysema, adult respiratory distress syndrome, hypotensive shock, septic shock, anaphylactic shock, insulin shock, sickle cell crisis, cardiac arrest, dysrhythmia, nitrogen narcosis, and neurological deficits caused by heart-lung bypass procedures.

In one embodiment, for example, the specific EPO compositions can be administered to prevent injury or tissue damage resulting from risk of injury or tissue damage during surgical procedures, such as, for example, tumor resection or aneurysm repair. Other pathologies caused by or resulting from hypoglycemia which are treatable by the methods described herein include insulin overdose, also referred to as iatrogenic hyperinsulinemia, insulinoma, growth hormone deficiency, hypocortisolism, drug overdose, and certain tumors.

Other pathologies resulting from excitable neuronal tissue damage include seizure disorders, such as epilepsy, convulsions, or chronic seizure disorders. Other treatable conditions and diseases include diseases such as stroke, multiple sclerosis, hypotension, cardiac arrest, Alzheimer's disease, Parkinson's disease, cerebral palsy, brain or spinal cord trauma, AIDS dementia, age-related loss of cognitive function, memory loss, amyotrophic lateral sclerosis, seizure disorders, alcoholism, retinal ischemia, optic nerve damage resulting from glaucoma, and neuronal loss.

The specific compositions and methods of the invention may be used to treat conditions of, and damage to, retinal tissue. Such disorders include, but are not limited to retinal ischemia, macular degeneration, retinal detachment, retinitis pigmentosa, arteriosclerotic retinopathy, hypertensive retinopathy, retinal artery blockage, retinal vein blockage, hypotension, and diabetic retinopathy.

In another embodiment, the methods principles of the invention may be used to protect or treat injury resulting from radiation damage to excitable tissue. A further utility of the methods of the present invention is in the treatment of neurotoxin poisoning, such as domoic acid shellfish poisoning, neurolathyrism, and Guam disease, amyotrophic lateral sclerosis, and Parkinson's disease.

As mentioned above, the present invention is also directed to a method for enhancing excitable tissue function in a mammal by peripheral administration of an erythropoietin as described above. Various diseases and conditions are amenable to treatment using this method, and further, this method is useful for enhancing cognitive function in the absence of any condition or disease. These uses of the present invention are describe in further detail below and include enhancement of learning and training in both human and non-human mammals.

Conditions and diseases treatable by the methods of this aspect of the present invention directed to the central nervous system include but are not limited to mood disorders, anxiety disorders, depression, autism, attention deficit hyperactivity disorder, and cognitive dysfunction. These conditions benefit from enhancement of neuronal function. Other disorders treatable in accordance with the teachings of the present invention include sleep disruption, for example, sleep apnea and travel-related disorders; subarachnoid and aneurismal bleeds, hypotensive shock, concussive injury, septic shock, anaphylactic shock, and sequelae of various encephalitides and meningitides, for example, connective tissue disease-related cerebritides such as lupus. Other uses include prevention of or protection from poisoning by neurotoxins, such as domoic acid shellfish poisoning, neurolathyrism, and Guam disease, amyotrophic lateral sclerosis, Parkinson's disease; postoperative treatment for embolic or ischemic injury; whole brain irradiation; sickle cell crisis; and eclampsia.

A further group of conditions treatable by the methods of the present invention include mitochondrial dysfunction, of either an hereditary or acquired nature, which are the cause of a variety of neurological diseases typified by neuronal injury and death. For example, Leigh disease (subacute necrotizing encephalopathy) is characterized by progressive visual loss and encephalopathy, due to neuronal drop out, and myopathy. In these cases, defective mitochondrial metabolism fails to supply enough high energy substrates to fuel the metabolism of excitable cells. An erythropoietin receptor activity modulator optimizes failing function in a variety of mitochondrial diseases. As mentioned above, hypoxic conditions adversely affect excitable tissues. The excitable tissues include, but are not limited to, central nervous system tissue, peripheral nervous system tissue, and heart tissue. In addition to the conditions described above, the methods of the present invention are useful in the treatment of inhalation poisoning such as carbon monoxide and smoke inhalation, severe asthma, adult respiratory distress syndrome, and choking and near drowning. Further conditions which create hypoxic conditions or by other means induce excitable tissue damage include hypoglycemia that may occur in inappropriate dosing of insulin, or with insulin-producing neoplasms (insulinoma).

Various neuropsychologic disorders which are believed to originate from excitable tissue damage are treatable by the instant methods. Chronic disorders in which neuronal damage is involved and for which treatment by the present invention is provided include disorders relating to the central nervous system and/or peripheral nervous system including age-related loss of cognitive function and senile dementia, chronic seizure disorders, Alzheimer's disease, Parkinson's disease, dementia, memory loss, amyotrophic lateral sclerosis, multiple sclerosis, tuberous sclerosis, Wilson's Disease cerebral and progressive supranuclear palsy, Guam disease, Lewy body dementia, prion diseases, such as spongiform encephalopathies, e.g., Creutzfeldt-Jakob disease, Huntington's disease, myotonic dystrophy, Freidrich's ataxia and other ataxias, as well as Gilles de la Tourette's syndrome, seizure disorders such as epilepsy and chronic seizure disorder, stroke, brain or spinal cord trauma, AIDS dementia, alcoholism, autism, retinal ischemia, glaucoma, autonomic function disorders such as hypertension and sleep disorders, and neuropsychiatric disorders that include, but are not limited to schizophrenia, schizoaffective disorder, attention deficit disorder, dysthymic disorder, major depressive disorder, mania, obsessive-compulsive disorder, psychoactive substance use disorders, anxiety, panic disorder, as well as unipolar and bipolar affective disorders. Additional neuropsychiatric and neurodegenerative disorders include, for example, those listed in the American Psychiatric Association's Diagnostic and Statistical manual of Mental Disorders (DSM), the most current version of which in incorporated herein by reference in its entirety.

In another embodiment, recombinant chimeric toxin molecules comprising erythropoietin can be used for therapeutic delivery of toxins to treat a proliferative disorder, such as cancer, or viral disorder, such as subacute sclerosing panencephalitis.

The following table lists additional exemplary, non-limiting indications as to the various conditions and diseases amenable to treatment by the aforementioned erythropoietins.

| Cell, tissue or organ | Dysfunction or pathology | Condition or disease | Type |
|---|---|---|---|
| Heart | Ischemia | Coronary artery disease | Acute, chronic |
| | | | Stable, unstable |
| | | Myocardial infarction | Dressler's syndrome |
| | | Angina | |
| | | Congenital heart disease | Valvular |
| | | | Cardiomyopathy |
| | | Prinzmetal angina | |
| | | Cardiac rupture | Aneurysmatic |
| | | | Septal perforation |
| | | Angiitis | |
| | Arrhythmia | Tachy-, bradyarrhythmia | Stable, unstable |
| | | | Hypersensitive carotid sinus node |
| | | Supraventricular, ventricular | |
| | | Conduction abnormalities | |
| | Congestive heart failure | Left, right, bi-ventricular | Cardiomyopathies, such as idiopathic familial, infective, metabolic, storage disease, deficiencies, connective tissue disorder, infiltration and granulomas, neurovascular |
| | | Myocarditis | Autoimmune, infective, idiopathic |
| | | Cor pulmonale | |
| | Blunt and penetrating trauma | | |
| | Toxins | Cocaine | |
| Vascular | Hypertension | Primary, secondary | |
| | Decompression sickness | | |
| | Fibromuscular hyperplasia | | |
| | Aneurysm | Dissecting, ruptured, enlarging | |
| Lungs | Obstructive | Asthma | |
| | | Chronic bronchitis, Emphysema and airway obstruction | |
| | Ischemic lung disease | Pulmonary embolism, Pulmonary thrombosis, Fat embolism | |
| | Environmental lung diseases | | |
| | Ischemic lung disease | Pulmonary embolism | |
| | | Pulmonary thrombosis | |
| | Interstitial lung disease | Idiopathic pulmonary fibrosis | |
| | Congenital | Cystic fibrosis | |
| | Cor pulmonale | | |
| | Trauma | | |
| | Pneumonia and pneumonitides | Infectious, parasitic, toxic, traumatic, burn, aspiration | |
| | Sarcoidosis | | |
| Pancreas | Endocrine | Diabetes mellitus, type I and II | Beta cell failure, dysfunction Diabetic neuropathy |
| | | Other endocrine cell failure of the pancreas | |
| | Exocrine | Exocrine pancreas failure | pancreatitis |
| Bone | Osteopenia | Primary secondary | Hypogonadism immobilisation Postmenopausal |

-continued

| Cell, tissue or organ | Dysfunction or pathology | Condition or disease | Type |
|---|---|---|---|
| | | | Age-related Hyperparathyroidism Hyperthyroidism Calcium, magnesium, phosphorus and/or vitamin D deficiency |
| | Osteomyelitis Avascular necrosis Trauma Paget's disease | | |
| Skin | Alopecia | Areata Totalis | Primary Secondary Male pattern baldness |
| | Vitiligo | Localized generalized | Primary secondary |
| | Diabetic ulceration Peripheral vascular disease Burn injuries | | |
| Autoimmune disorders | Lupus erythematodes, Sjiogren, Rheumatoid arthritis, Glomerulonephritis, Angiitis Langerhan's histiocytosis | | |
| Eye | Optic neuritis Blunt and penetrating injuries, Infections, Sarcoid, Sickle C disease, Retinal detachment, Temporal arteritis | | |
| Embryonic and fetal disorders | Asphyxia Ischemia | | |
| CNS | Chronic fatigue syndrome, acute and chronic hypoosmolar and hyperosmolar syndromes, AIDS Dementia, Electrocution | | |
| | Encephalitis Meningitis Subdural hematoma Nicotine addiction | Rabies, Herpes | |
| | Drug abuse and withdrawal | Cocaine, heroin, crack, marijuana, LSD, PCP, poly-drug abuse, ecstasy, opioids, sedative hypnotics, amphetamines, caffeine | |
| | Obsessive-compulsive disorders Spinal stenosis, Transverse myelitis, Guillian Barre, Trauma, Nerve root compression, Tumoral compression, Heat stroke | | |
| ENT | Tinnitus Meuniere's syndrome Hearing loss | | |

-continued

| Cell, tissue or organ | Dysfunction or pathology | Condition or disease | Type |
|---|---|---|---|
| Kidney | Traumatic injury, barotrauma Renal failure | Acute, chronic | Vascular/ischemic, interstitial disease, diabetic kidney disease, nephrotic syndromes, infections |
| Striated muscle | Henoch S. Purpura Autoimmune disorders | Myasthenia gravis Dermatomyositis Polymyositis | |
| | Myopathies | Inherited metabolic, endocrine and toxic | |
| | Heat stroke Crush injury Rhabdomylosis Mitochondrial disease | | |
| | Infection | Necrotizing fasciitis | |
| Sexual dysfunction | Central and peripheral | Impotence secondary to medication | |
| Liver | hepatitis | Viral, bacterial, parasitic | |
| | Ischemic disease Cirrhosis, fatty liver Infiltrative/ metabolic diseases | | |
| Gastrointestinal | Ischemic bowel disease Inflammatory bowel disease Necrotizing enterocolitis | | |
| Organ transplantation | Treatment of donor and recipient | | |
| Reproductive tract | infertility | Vascular Autoimmune Uterine abnormalities Implantation disorders | |
| Endocrine | Glandular hyper- and hypofunction | | |

As mentioned above, these diseases, disorders or conditions are merely illustrative of the range of benefits provided by the erythropoietins of the invention. Accordingly, this invention generally provides therapeutic or prophylactic treatment of the consequences of mechanical trauma or of human diseases. Therapeutic or prophylactic treatment for diseases, disorders or conditions of the CNS and/or peripheral nervous system are preferred. Therapeutic or prophylactic treatment for diseases, disorders or conditions which have a psychiatric component is provided. Therapeutic or prophylactic treatment for diseases, disorders or conditions including but not limited to those having an ophthalmic, cardiovascular, cardiopulmonary, respiratory, kidney, urinary, reproductive, gastrointestinal, endocrine, or metabolic component is provided.

In one embodiment, such a pharmaceutical composition of an erythropoietin may be administered systemically to protect or enhance the target cells, tissue or organ. Such administration may be parenterally, via inhalation, or transmucosally, e.g., orally, nasally, rectally, intravaginally, sublingually, submucosally or transdermally. Preferably, administration is parenteral, e.g., via intravenous or intraperitoneal injection, and also including, but is not limited to, intra-arterial, intramuscular, intradermal and subcutaneous administration.

For other routes of administration, such as by use of a perfusate, injection into an organ, or other local administration, a pharmaceutical composition will be provided which results in similar levels of an erythropoietin as described above. A level of about 15 pM-30 nM is preferred.

The pharmaceutical compositions of the invention may comprise a therapeutically effective amount of a compound, and a pharmaceutically acceptable carrier. In a specific embodiment, the term "pharmaceutically acceptable" means approved by a regulatory agency of the Federal or a state government or listed in the U.S. Pharmacopeia or other generally recognized foreign pharmacopeia for use in animals, and more particularly in humans. The term "carrier" refers to a diluent, adjuvant, excipient, or vehicle with which the therapeutic is administered. Such pharmaceutical carriers can be sterile liquids, such as saline solutions in water and oils, including those of petroleum, animal, vegetable or synthetic origin, such as peanut oil, soybean oil, mineral oil, sesame oil and the like. A saline solution is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. The compounds of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

Pharmaceutical compositions adapted for oral administration may be provided as capsules or tablets; as powders or granules; as solutions, syrups or suspensions (in aqueous or non-aqueous liquids); as edible foams or whips; or as emulsions. Tablets or hard gelatine capsules may comprise lactose, starch or derivatives thereof, magnesium stearate, sodium saccharine, cellulose, magnesium carbonate, stearic acid or salts thereof. Soft gelatine capsules may comprise vegetable oils, waxes, fats, semi-solid, or liquid polyols etc. Solutions and syrups may comprise water, polyols and sugars.

An active agent intended for oral administration may be coated with or admixed with a material that delays disintegration and/or absorption of the active agent in the gastrointestinal tract (e.g., glyceryl monostearate or glyceryl distearate may be used). Thus, the sustained release of an active agent may be achieved over many hours and, if necessary, the active agent can be protected from being degraded within the stomach. Pharmaceutical compositions for oral administration may be formulated to facilitate release of an active agent at a particular gastrointestinal location due to specific pH or enzymatic conditions.

Pharmaceutical compositions adapted for transdermal administration may be provided as discrete patches intended to remain in intimate contact with the epidermis of the recipient for a prolonged period of time. Pharmaceutical compositions adapted for topical administration may be provided as ointments, creams, suspensions, lotions, powders, solutions, pastes, gels, sprays, aerosols or oils. For topical administration to the skin, mouth, eye or other external tissues a topical ointment or cream is preferably used. When formulated in an ointment, the active ingredient may be employed with either a paraffinic or a water-miscible ointment base. Alternatively, the active ingredient may be formulated in a cream with an oil-in-water base or a water-in-oil base. Pharmaceutical compositions adapted for topical administration to the eye include eye drops. In these compositions, the active ingredient can be dissolved or suspended in a suitable carrier, e.g., in an aqueous solvent. Pharmaceutical compositions adapted for topical administration in the mouth include lozenges, pastilles and mouthwashes.

Pharmaceutical compositions adapted for nasal and pulmonary administration may comprise solid carriers such as powders (preferably having a particle size in the range of 20 to 500 microns). Powders can be administered in the manner in which snuff is taken, i.e., by rapid inhalation through the nose from a container of powder held close to the nose. Alternatively, compositions adopted for nasal administration may comprise liquid carriers, e.g., nasal sprays or nasal drops. Alternatively, inhalation directly into the lungs may be accomplished by inhalation deeply or installation through a mouthpiece into the oropharynx. These compositions may comprise aqueous or oil solutions of the active ingredient. Compositions for administration by inhalation may be supplied in specially adapted devices including, but not limited to, pressurized aerosols, nebulizers or insufflators, which can be constructed so as to provide predetermined dosages of the active ingredient. In a preferred embodiment, pharmaceutical compositions of the invention are administered into the nasal cavity directly or into the lungs via the nasal cavity or oropharynx.

Pharmaceutical compositions adapted for rectal administration may be provided as suppositories or enemas. Pharmaceutical compositions adapted for vaginal administration may be provided as pessaries, tampons, creams, gels, pastes, foams or spray formulations.

Pharmaceutical compositions adapted for parenteral administration include aqueous and non-aqueous sterile injectable solutions or suspensions, which may contain anti-oxidants, buffers, bacteriostats and solutes that render the compositions substantially isotonic with the blood of an intended recipient. Other components that may be present in such compositions include water, alcohols, polyols, glycerine and vegetable oils, for example. Compositions adapted for parenteral administration may be presented in unit-dose or multi-dose containers, for example sealed ampules and vials, and may be stored in a freeze-dried (lyophilized) condition requiring only the addition of a sterile liquid carrier, e.g., sterile saline solution for injections, immediately prior to use. Extemporaneous injection solutions and suspensions may be prepared from sterile powders, granules and tablets. In one embodiment, an autoinjector comprising an injectable solution of an erythropoietin may be provided for emergency use by ambulances, emergency rooms, and battlefield situations, and even for self-administration in a domestic setting, particularly where the possibility of traumatic amputation may occur, such as by imprudent use of a lawn mower. The likelihood that cells and tissues in a severed foot or toe will survive after reattachment may be increased by administering an erythropoietin to multiple sites in the severed part as soon as practicable, even before the arrival of medical personnel on site, or arrival of the afflicted individual with severed toe in tow at the emergency room.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilized powder or water-free concentrate in a hermetically-sealed container such as an ampule or sachette indicating the quantity of active agent. Where the composition is to be administered by infusion, it can be dispensed with an infusion bottle containing sterile pharmaceutical grade water or saline. Where the composition is administered by injection, an ampule of sterile saline can be provided so that the ingredients may be mixed prior to administration.

Suppositories generally contain active ingredient in the range of 0.5% to 10% by weight; oral formulations preferably contain 10% to 95% active ingredient.

A perfusate composition may be provided for use in transplanted organ baths, for in situ perfusion, or for administration to the vasculature of an organ donor prior to organ harvesting. Such pharmaceutical compositions may comprise levels of an erythropoietin or a form of an erythropoietin not suitable for acute or chronic, local or systemic administration to an individual, but will serve the functions intended herein in a cadaver, organ bath, organ perfusate, or in situ perfusate prior to removing or reducing the levels of the erythropoietin contained therein before exposing or returning the treated organ or tissue to regular circulation. The erythropoietin for this aspect of the invention may be any erythropoietin, such as naturally-occurring forms such as human erythropoietin, or any of the erythropoietins hereinabove described, such as asialoerythropoietin and phenylglyoxal-erythropoietins, as non-limiting examples.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

In another embodiment, for example, erythropoietin can be delivered in a controlled-release system. For example, the polypeptide may be administered using intravenous infusion, an implantable osmotic pump, a transdermal patch, liposomes, or other modes of administration. In one embodiment, a pump may be used (see Langer, supra; Sefton, 1987, CRC Crit. Ref. Biomed. Eng. 14:201; Buchwald et at., 1980, Surgery 88:507; Saudek et al., 1989, N. Engl. J. Med. 321:574). In another embodiment, the compound can be delivered in a vesicle, in particular a liposome (see Langer, *Science* 249: 1527-1533 (1990); Treat et al., in Liposomes in the Therapy of Infectious Disease and Cancer, Lopez-Berestein and Fidler (eds.), Liss, New York, pp. 353-365 (1989); WO 91/04014; U.S. Pat. No. 4,704,355; Lopez-Berestein, ibid., pp. 317-327; see generally ibid.). In another embodiment, polymeric materials can be used [see Medical Applications of Controlled Release, Langer and Wise (eds.), CRC Press: Boca Raton, Fla., 1974; Controlled Drug Bioavailability, Drug Product Design and Performance, Smolen and Ball (eds.), Wiley: New York (1984); Ranger and Peppas, J. Macromol. Sci. Rev. Macromol. Chem. 23:61, 1953; see also Levy et al., 1985, Science 228:190; During et al., 1989, Ann. Neurol. 25:351; Howard et al., 1989, J. Neurosurg. 71:105).

In yet another embodiment, a controlled release system can be placed in proximity of the therapeutic target, i.e., the target cells, tissue or organ, thus requiring only a fraction of the systemic dose (see, e.g., Goodson, pp. 115-138 in Medical Applications of Controlled Release, vol. 2, supra, 1984). Other controlled release systems are discussed in the review by Langer (1990, Science 249:1527-1533).

In another embodiment, erythropoietin, as properly formulated, can be administered by nasal, oral, rectal, vaginal, or sublingual administration.

In a specific embodiment, it may be desirable to administer the erythropoietin compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as silastic membranes, or fibers.

Selection of the preferred effective dose will be determined by a skilled artisan based upon considering several factors which will be known to one of ordinary skill in the art. Such factors include the particular form of erythropoietin, and its pharmacokinetic parameters such as bioavailability, metabolism, half-life, etc., which will have been established during the usual development procedures typically employed in obtaining regulatory approval for a pharmaceutical compound. Further factors in considering the dose include the condition or disease to be treated or the benefit to be achieved in a normal individual, the body mass of the patient, the route of administration, whether administration is acute or chronic, concomitant medications, and other factors well known to affect the efficacy of administered pharmaceutical agents. Thus the precise dosage should be decided according to the judgment of the practitioner and each patient's circumstances, e.g., depending upon the condition and the immune status of the individual patient, according to standard clinical techniques.

In another aspect of the invention, a perfusate or perfusion solution is provided for perfusion and storage of organs for transplant, the perfusion solution including an amount of an erythropoietin effective to protect erythropoietin-responsive cells and associated cells, tissues or organs. Transplant includes but is not limited to xenotransplantation, where a organ (including cells, tissue or other bodily part) is harvested from one donor and transplanted into a different recipient; and autotransplant, where the organ is taken from one part of a body and replaced at another, including bench surgical procedures, in which an organ may be removed, and while ex vivo, resected, repaired, or otherwise manipulated, such as for tumor removal, and then returned to the original location. In one embodiment, the perfusion solution is the University of Wisconsin (UW) solution (U.S. Pat. No. 4,798,824) which contains from about 1 to about 25 U/ml erythropoietin, 5% hydroxyethyl starch (having a molecular weight of from about 200,000 to about 300,000 and substantially free of ethylene glycol, ethylene chlorohydrin, sodium chloride and acetone); 25 mM $KH_2PO_4$, 3 mM glutathione; 5 mM adenosine; 10 mM glucose; 10 mM HEPES buffer; 5 mM magnesium gluconate; 1.5 mM $CaCl_2$; 105 mM sodium gluconate; 200,000 units penicillin; 40 units insulin; 16 mg Dexamethasone; 12 mg Phenol Red; and has a pH of 7.4-7.5 and an osmolality of about 320 mOSm/l. The solution is used to maintain cadaveric kidneys and pancreases prior to transplant. Using the solution, preservation can be extended beyond the 30-hour limit recommended for cadaveric kidney preservation. This particular perfusate is merely illustrative of a number of such solutions that can be adapted for the present use by inclusion of an effective amount of an erythropoietin. In a further embodiment, the perfusate solution contains from about 5 to about 35 U/ml erythropoietin, or from about 10 to about 30 U/ml erythropoietin. As mentioned above, any form of erythropoietin can be used in this aspect of the invention.

While the preferred recipient of an erythropoietin for the purposes herein throughout is a human, the methods herein apply equally to other mammals, particularly domesticated animals, livestock, companion and zoo animals. However, the invention is not so limiting and the benefits can be applied to any mammal.

In further aspects of the ex-vivo invention, any erythropoietin such as but not limited to the erythropoietins described above, as well as native erythropoietins as well as an analog thereof, an erythropoietin mimetic, and erythropoietin fragment, a hybrid erythropoietin molecule, an erythropoietinreceptor-binding molecule, an erythropoietin agonist, a renal erythropoietin, a brain erythropoietin, an oligomer thereof, a multimer thereof, a mutein thereof, a congener thereof, a naturally-occurring form thereof, a synthetic form thereof, a recombinant form thereof, a glycosylation variant thereof, a deglycosylated variant thereof, or a combination thereof.

In another aspect of the invention, methods and compositions for enhancing the viability of cells, tissues or organs which are not isolated from the vasculature by an endothelial cell barrier are provided by exposing the cells, tissue or organs directly to a pharmaceutical composition comprising an erythropoietin, or administering or contacting an erythropoietin-containing pharmaceutical composition to the vasculature of the tissue or organ. Enhanced activity of erythropoietin-responsive cells in the treated tissue or organ are responsible for the positive effects exerted.

As described above, the invention is based, in part, on the discovery that erythropoietin molecules can be transported from the luminal surface to the basement membrane surface of endothelial cells of the capillaries of organs with endothelial cell tight junctions, including, for example, the brain, retina, and testis. Thus, erytnropoietin-responsive cells across the barrier are susceptible targets for the beneficial effects of erythropoietin, and others cell types or tissues or organs that contain and depend in whole or in part on erythropoietin-responsive cells therein are targets for the methods of the invention. While not wishing to be bound by any particular theory, after transcytosis of erythropoietin, erythropoietin can interact with an erythropoietin receptor on an erythropoietin-responsive cell, for example, neuronal, retinal, muscle, heart, lung, liver, kidney, small intestine, adrenal cortex, adrenal medulla, capillary endothelial, testes, ovary, or endometrial cell, and receptor binding can initiate a signal transduction cascade resulting in the activation of a gene expression program within the erythropoietin-responsive cell or tissue, resulting in the protection of the cell or tissue, or organ, from damage, such as by toxins, chemotherapeutic agents, radiation therapy, hypoxia, etc. Thus, methods for protecting erythropoietin-responsive cell-containing tissue from injury or hypoxic stress, and enhancing the function of such tissue are described in detail hereinbelow.

In the practice of one embodiment of the invention, a mammalian patient is undergoing systemic chemotherapy for cancer treatment, including radiation therapy, which commonly has adverse effects such as nerve, lung, heart, ovarian or testicular damage. Administration of a pharmaceutical composition comprising an erythropoietin as described above is performed prior to and during chemotherapy and/or radiation therapy, to protect various tissues and organs from damage by the chemotherapeutic agent, such as to protect the testes. Treatment may be continued until circulating levels of the chemotherapeutic agent have fallen below a level of potential danger to the mammalian body.

In the practice of another embodiment of the invention, various organs were planned to be harvested from a victim of an automobile accident for transplant into a number of recipients, some of which required transport for an extended distance and period of time. Prior to organ harvesting, the victim was infused with a pharmaceutical composition comprising an erythropoietin as described herein. Harvested organs for shipment were perfused with a perfusate containing erythropoietin as described herein, and stored in a bath comprising erythropoietin. Certain organs were continuously perfused with a pulsatile perfusion device, utilizing a perfusate containing an erythropoietin in accordance with the present invention. Minimal deterioration of organ function occurred during the transport and upon implant and reperfusion of the organs in situ.

In another embodiment of the invention, a surgical procedure to repair a heart valve required temporary cardioplegia and arterial occlusion. Prior to surgery, the patient was infused with 500 U erythropoietin per kg body weight. Such treatment prevented hypoxic ischemic cellular damage, particularly after reperfusion.

In another embodiment of the invention, in any surgical procedure, such as in cardiopulmonary bypass surgery, a naturally-occurring erythropoietin or any erythropoietin of the invention can be used. In one embodiment, administration of a pharmaceutical composition comprising an erythropoietin as described above is performed prior to, during, and/or following the bypass procedure, to protect the function of brain, heart, and other other organs.

In the foregoing examples in which an erythropoietin of the invention, including naturally-occurring erythropoietin, is used for ex-vivo applications, or to treat erythropoietin-responsive cells such as neuronal tissue, retinal tissue, heart, lung, liver, kidney, small intestine, adrenal cortex, adrenal medulla, capillary endothelial, testes, ovary, or endometrial cells or tissue, the invention provides a pharmaceutical composition in dosage unit form adapted for protection or enhancement of erythropoietin-responsive cells, tissues or organs distal to the vasculature which comprises, per dosage unit, an effective non-toxic amount within the range from about 50,000 to 500,000 Units, 60,000 to 500,000 Units, 70,000 to 500,000 Units, 80,000 to 500,000 Units, 90,000 to 500,000 Units, 100,000 to 500,000 Units, 150,000 to 500,000 Units, 200,000 to 500,000 Units, 250,000 to 500,000 Units, 300,000 to 500,000 Units, 350,000 to 500,000 Units, 400,000 to 500,000 Units, or 450,000 to 500,000 Units of erythropoietin, an erythropoietin receptor activity modulator, or an erythropoietin-activated receptor modulator and a pharmaceutically acceptable carrier. In a preferred embodiment, the effective non-toxic amount of erythropoietin is within the range from about 50,000 to 500,000 Units. In a preferred embodiment, the erythropoietin in the aforementioned composition is non-erythropoietic.

In a further aspect of the invention, erythropoietin administration was found to restore cognitive function in animals having undergone brain trauma. After a delay of either 5 days or 30 days, administration of erythropoietin was still able to restore function as compared to sham-treated animals, indicating the ability of an erythropoietin to regenerate or restore brain activity. Thus, the invention is also directed to the use of an erythropoietin for the preparation of a pharmaceutical composition for the treatment of brain trauma and other cognitive dysfunctions, including treatment well after the injury (e.g. three days, five days, a week, a month, or longer). The invention is also directed to a method for the treatment of cognitive dysfunction following injury by administering an effective amount of an erythropoietin. Any erythropoietin as described herein may be used for this aspect of the invention.

Furthermore, this restorative aspect of the invention is directed to the use of any of the erythropoietins herein for the preparation of a pharmaceutical composition for the restoration of cellular, tissue or organ dysfunction, wherein treatment is initiated after, and well after, the initial insult responsible for the dysfunction. Moreover, treatment using erythropoietins of the invention can span the course of the disease or condition during the acute phase as well as a chronic phase.

In the instance wherein an erythropoietin of the invention has erythropoietic activity, in a preferred embodiment, erythropoietin may be administered systemically at a dosage between about 300 and about 10,000 Units/kg body weight, preferably about 500-5,000 Units/kg-body weight, most preferably about 1,000 Units/kg-body weight, per administration. This effective dose should be sufficient to achieve serum levels of erythropoietin greater than about 10,000, 15,000, or 20,000 mU/ml of serum after erythropoietin administration. Such serum levels may be achieved at about 1, 2, 3, 4, 5, 6, 7, 8, 9, or 10 hours post-administration. Such dosages may be repeated as necessary. For example, administration may be repeated daily, as long as clinically necessary, or after an appropriate interval, e.g., every 1 to 12 weeks, preferably, every 1 to 3 weeks. In one embodiment, the effective amount of erythropoietin and a pharmaceutically acceptable carrier may be packaged in a single dose vial or other container. In another embodiment, an erythropoietin useful for the purposes herein is nonerythropoietic, i.e., it is capable of exerting the activities described herein but not causing an increase in hemoglobin concentration or hematocrit. Such a non-erythropoietic form of erythropoietin is preferred in instances wherein the methods of the present invention are intended to be provided chronically. In another embodiment, an erythropoietin is given at a dose greater than that necessary to maximally stimulate erythropoiesis. As noted above, an erythropoietin of the invention does not necessarily have erythropoietic activity, and therefore the above dosages expressed in hematopoietic units is merely exemplary for erythropoietins that are erythropoietic; hereinabove molar equivalents for dosages are provided which are applicable to any erythropoietin.

The present invention is further directed to a method for facilitating the transport of a molecule across an endothelial cell barrier in a mammal by administering a composition which comprises the particular molecule in association with an erythropoietin as described hereinabove. As described above, tight junctions between endothelial cells in certain organs in the body create a barrier to the entry of certain molecules. For treatment of various conditions within the barriered organ, means for facilitating passage of pharmaceutical agents is desired. An erythropoietin of the invention is useful as a carrier for delivering other molecules across the blood-brain and other similar barriers. A composition comprising a molecule desirous of crossing the barrier with erythropoietin is prepared, and peripheral administration of the composition results in the transcytosis of the composition across the barrier. The association between the molecule to be transported across the barrier and the erythropoietin may be a labile covalent bond, in which case the molecule is released from association with the erythropoietin after crossing the barrier. If the desired pharmacological activity of the molecule is maintained or unaffected by association with erythropoietin, such a complex can be administered.

The skilled artisan will be aware of various means for associating molecules with an erythropoietin of the invention and the other agents described above, by covalent, non-covalent, and other means; furthermore, evaluation of the efficacy of the composition can be readily determined in an experimental system. Association of molecules with an erythropoietin may be achieved by any number of means, including labile, covalent binding, cross-linking, etc. Biotin/avidin interactions may be employed. As mentioned above, a hybrid molecule may be prepared by recombinant or synthetic means, for example, which includes both the domain of the molecule with desired pharmacological activity and the domain responsible for erythropoietin receptor activity modulation.

A molecule may be conjugated to an erythropoietin through a polyfunctional molecule, i.e., a polyfunctional crosslinker. As used herein, the term "polyfunctional molecule" encompasses molecules having one functional group that can react more than one time in succession, such as formaldehyde, as well as molecules with more than one reactive group. As used herein, the term "reactive group" refers to a functional group on the crosslinker that reacts with a functional group on a molecule (e.g., peptide, protein, carbohydrate, nucleic acid, particularly a hormone, antibiotic, or anti-cancer agent to be delivered across an endothelial cell barrier) so as to form a covalent bond between the cross-linker and that molecule. The term "functional group" retains its standard meaning in organic chemistry. The polyfunctional molecules which can be used are preferably biocompatible linkers, i.e., they are noncarcinogenic, nontoxic, and substantially non-immunogenic in vivo. Polyfunctional cross-linkers such as those known in the art and described herein can be readily tested in animal models to determine their biocompatibility. The polyfunctional molecule is preferably bifunctional. As used herein, the term "bifunctional molecule" refers to a molecule with two reactive groups. The bifunctional molecule may be heterobifunctional or homobifunctional. A heterobifunctional cross-linker allows for vectorial conjugation. It is particularly preferred for the polyfunctional molecule to be sufficiently soluble in water for the cross-linking reactions to occur in aqueous solutions such as in aqueous solutions buffered at pH 6 to 8, and for the resulting conjugate to remain water soluble for more effective bio-distribution. Typically, the polyfunctional molecule covalently bonds with an amino or a sulfhydryl functional group. However, polyfunctional molecules reactive with other functional groups, such as carboxylic acids or hydroxyl groups, are contemplated in the present invention.

The homobifunctional molecules have at least two reactive functional groups, which are the same. The reactive functional groups on a homobifunctional molecule include, for example, aldehyde groups and active ester groups. Homobifunctional molecules having aldehyde groups include, for example, glutaraldehyde and subaraldehyde. The use of glutaraldehyde as a cross-linking agent was disclosed by Poznansky et al., Science 223, 1304-1306 (1984). Homobifunctional molecules having at least two active ester units include esters of dicarboxylic acids and N-hydroxysuccinimide. Some examples of such N-succinimidyl esters include disuccinimidyl suberate and dithio-bis-(succinimidyl propionate), and their soluble bis-sulfonic acid and bis-sulfonate salts such as their sodium and potassium salts. These homobifunctional reagents are available from Pierce, Rockford, Ill.

The heterobifunctional molecules have at least two different reactive groups. The reactive groups react with different functional groups, e.g., present on the erythropoietin and the molecule. These two different functional groups that react with the reactive group on the heterobifunctional cross-linker are usually an amino group, e.g., the epsilon amino group of lysine; a sulfhydryl group, e.g., the thiol group of cysteine; a carboxylic acid, e.g., the carboxylate on aspartic acid; or a hydroxyl group, e.g., the hydroxyl group on serine.

Of course, the various erythropoietin molecules of the invention may not have suitable reactive groups available for use with certain cross-linking agent; however, one of skill in the art will be amply aware of the choice of cross-linking agents based on the available groups for cross-linking in an erythropoietin of the invention.

When a reactive group of a heterobifunctional molecule forms a covalent bond with an amino group, the covalent bond will usually be an amido or imido bond. The reactive group that forms a covalent bond with an amino group may, for example, be an activated carboxylate group, a halocarbonyl group, or an ester group. The preferred halocarbonyl group is a chlorocarbonyl group. The ester groups are preferably reactive ester groups such as, for example, an N-hydroxy-succinimide ester group.

The other functional group typically is either a thiol group, a group capable of being converted into a thiol group, or a group that forms a covalent bond with a thiol group. The covalent bond will usually be a thioether bond or a disulfide. The reactive group that forms a covalent bond with a thiol group may, for example, be a double bond that reacts with thiol groups or an activated disulfide. A reactive group containing a double bond capable of reacting with a thiol group is the maleimido group, although others, such as acrylonitrile, are also possible. A reactive disulfide group may, for example, be a 2-pyridyldithio group or a 5,5'-dithio-bis-(2-nitrobenzoic acid) group. Some examples of heterobifunctional reagents containing reactive disulfide bonds include N-succinimidyl 3-(2-pyridyl-dithio)propionate (Carlsson, et al., 1978, Biochem J., 173:723-737), sodium S-4-succinimidyloxycarbonyl-alpha-methylbenzylthiosulfate, and 4-succinimidyloxycarbonyl-alpha-methyl-(2-pyridyldithio)toluene. N-succinimidyl 3-(2-pyridyldithio)propionate is preferred. Some examples of heterobifunctional reagents comprising reactive groups having a double bond that reacts with a thiol group include succinimidyl 4-(N-maleimidomethyl)cyclohexane-1-carboxylate and succinimidyl m-maleimidobenzoate.

Other heterobifunctional molecules include succinimidyl 3-(maleimido)propionate, sulfosuccinimidyl 4-(p-maleimido-phenyl)butyrate, sulfosuccinimidyl 4-(N-maleimidomethyl-cyclohexane)-1-carboxylate, maleimidobenzoyl-N-hydroxy-succinimide ester. The sodium sulfonate salt of succinimidyl m-maleimidobenzoate is preferred. Many of the above-mentioned heterobifunctional reagents and their sulfonate salts are available from Pierce Chemical Co., Rockford, Ill. USA.

The need for the above-described conjugated to be reversible or labile may be readily determined by the skilled artisan. A conjugate may be tested in vitro for both the erythropoietin, and for the desirable pharmacological activity. If the conjugate retains both properties, its suitability may then be tested in vivo. If the conjugated molecule requires separation from the erythropoietin for activity, a labile bond or reversible association with erythropoietin will be preferable. The lability characteristics may also be tested using standard in vitro procedures before in vivo testing.

Additional information regarding how to make and use these as well as other polyfunctional reagents may be obtained from the following publications or others available in the art:

Carlsson, J. et al., 1978, Biochem. J. 173:723-737.
Cumber, J. A. et al., 1985, Methods in Enzymology 112: 207-224.
Jue, R. et al., 1978, Biochem 17:5399-5405.
Sun, T. T. et al., 1974, Biochem. 13:2334-2340.
Blattler, W. A. et al., 1985, Biochem. 24:1517-152.
Liu, F. T. et al., 1979, Biochem. 18:690-697.
Youle, R. J. and Neville, D. M. Jr., 1980, Proc. Natl. Acad. Sci. U.S.A. 77:5483-5486.
Lerner, R. A. et al., 1981, Proc. Natl. Acad. Sci. U.S.A. 78:3403-3407.
Jung, S. M. and Moroi, M., 1983, Biochem. Biophys. Acta 761:162.
Caulfield, M. P. et al., 1984, Biochem. 81:7772-7776.
Staros, J. V., 1982, Biochem. 21:3950-3955.
Yoshitake, S. et al., 1979, Eur. J. Biochem. 101:395-399.
Yoshitake, S. et al., 1982, J. Biochem. 92:1413-1424.
Pilch, P. F. and Czech, M. P., 1979, J. Biol. Chem. 254: 3375-3381.
Novick, D. et al., 1987, J. Biol. Chem. 262:8483-8487.
Lomant, A. J. and Fairbanks, G., 1976, J. Mol. Biol. 104: 243-261.
Hamada, H. and Tsuruo, T., 1987, Anal. Biochem. 160: 483-488.
Hashida, S. et al., 1984, J. Applied Biochem. 6:56-63.

Additionally, methods of cross-linking are reviewed by Means and Feeney, 1990, Bioconjugate Chem. 1:2-12.

Barriers which are crossed by the above-described methods and compositions of the present invention include but are not limited to the blood-brain barrier, the blood-eye barrier, the blood-testes barrier, the blood-ovary barrier, and the blood-uterus barrier.

Candidate molecules for transport across an endothelial cell barrier include, for example, hormones such as growth hormone, neurotrophic factors, antibiotics or antifungals such as those normally excluded from the brain and other barriered organs, peptide radiopharmaceuticals, antisense drugs, antibodies against biologically-active agents, pharmaceuticals, and anti-cancer agents. Non-limiting examples of such molecules include growth hormone, nerve growth factor (NGF), brain-derived neurotrophic factor (BDNF), ciliary neurotrophic factor (CNTF), basic fibroblast growth factor (bFGF), transforming growth factor β1 (TGFβ1), transforming growth factor β2 (TGFβ2), transforming growth factor β3 (TGFβ3), interleukin 1, interleukin 2, interleukin 3, and interleukin 6, AZT, antibodies against tumor necrosis factor, and immunosuppressive agents such as cyclosporin.

The present invention is also directed to a composition comprising a molecule to be transported via transcytosis across a endothelial cell tight junction barrier and an erythropoietin as described above. The invention is further directed to the use of a conjugate between a molecule and an erythropoietin as described above for the preparation of a pharmaceutical composition for the delivery of the molecule across a barrier as described above.

The present invention may be better understood by reference to the following non-limiting Examples, which are provided as exemplary of the invention. The following examples are presented in order to more fully illustrate the preferred embodiments of the invention. They should in no way be construed, however, as limiting the broad scope of the invention.

EXAMPLE 1

Erythropoietin Crosses the Blood-Cerebrospinal Fluid Tight Barrier

Adult male Sprague-Dawley rats were anesthetized and administered recombinant human erythropoietin intraperitoneally. Cerebrospinal fluid was sampled from the cisterna magna at 30 minute intervals up to 4 hrs and the erythropoietin concentration determined using a sensitive and specific enzyme-linked immunoassay. As illustrated in FIG. 1, the baseline erythropoietin concentration in CSF is 8 mU/ml. After a delay of several hours, the levels of erythropoietin measured in the CSF begin to rise and by 2.5 hours and later are significantly different from the baseline concentration at the p<0.01 level. The peak level of about 100 mU/ml is within the range known to exert protective effects in vitro (0.1 to 100 mU/ml). The time to peak occurs at about 3.5 hrs, which is delayed significantly from the peak serum levels (less than 1 hr). The results of this experiment illustrate that significant levels of erythropoietin can be accomplished across a tight cellular junction by bolus parenteral administration of erythropoietin at appropriate concentrations.

EXAMPLE 2

Maintenance of Function in Heart Prepared for Transplantation

Wistar male rats weighing 300 to 330 g are given erythropoietin (5000 U/kg body weight) or vehicle 24 h prior to removal of the heart for ex vivo studies, done in accordance with the protocol of Delcayre et al., 1992, *Amer. J. Physiol.* 263:H1537-45. Animals are sacrificed with pentobarbital (0.3 mL), and intravenously heparinized (0.2 mL). The hearts are initially allowed to equilibrate for 15 min The left ventricular balloon is then inflated to a volume that gives an end-diastolic pressure of 8 mm Hg. A left ventricular pressure-volume curve is constructed by incremental inflation of the balloon volume by 0.02 ml aliquots. Zero volume is defined as the point at which the left ventricular end-diastolic pressure is zero. On completion of the pressure-volume curve, the left ventricular balloon is deflated to set end-diastolic pressure back to 8 mmHg and the control period is pursued for 15 min, after check of coronary flow. Then the heart is arrested with 50 mL Celsior+molecule to rest at 4° C. under a pressure of 60 cm $H_2O$. The heart is then removed and stored 5 hours at 4° C. in plastic container filled with the same solution and surrounded with crushed ice.

Figure 2:
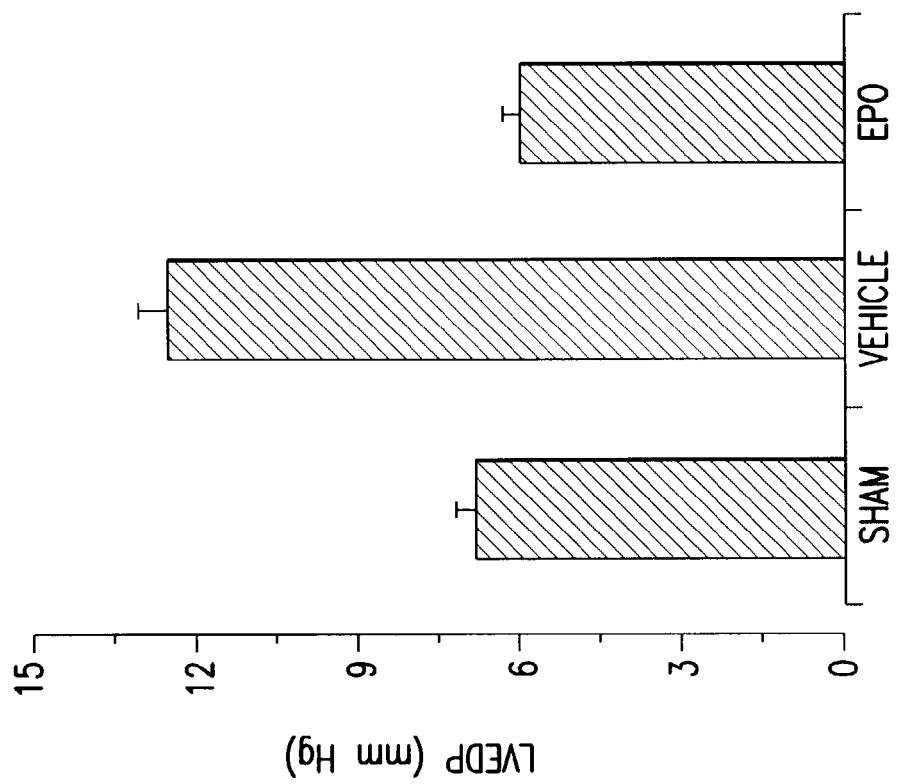
FIG. 2 shows the protection of the myocardium from ischemic damage by erythropoietin after temporary vascular occlusion.

On completion of storage, the heart is transferred to a Langendorff apparatus. The balloon catheter is re-inserted into the left ventricle and re-inflated to the same volume as during preischemic period. The heart is re-perfused for at least 2 hours at 37° C. The re-perfusion pressure is set at 50 cm $H_2O$ for 15 min of re-flow and then back to 100 cm $H_2O$ for the 2 next hours. Pacing (320 beats per minute) is re-instituted. Isovolumetric measurements of contractile indexes and diastolic pressure are taken in triplicate at 25, 45, 60, 120 min of reperfusion. At this time point pressure volume curves are performed and coronary effluent during the 45 mn reperfusion collected to measure creatine kinase leakage. The two treatment groups are compared using an unpaired t-test, and a linear regression using the end-diastolic pressure data is used to design compliance curves. As shown in FIG. 2, significant improvement of left ventricular pressure developed occurs after treatment with erythropoietin, as well as improved volume-pressure curve, decrease of left diastolic ventricular pressure and decrease of creatine kinase leakage.

EXAMPLE 3

Erythropoietin Protects Myocardium from Ischemic Injury

Figure 3:
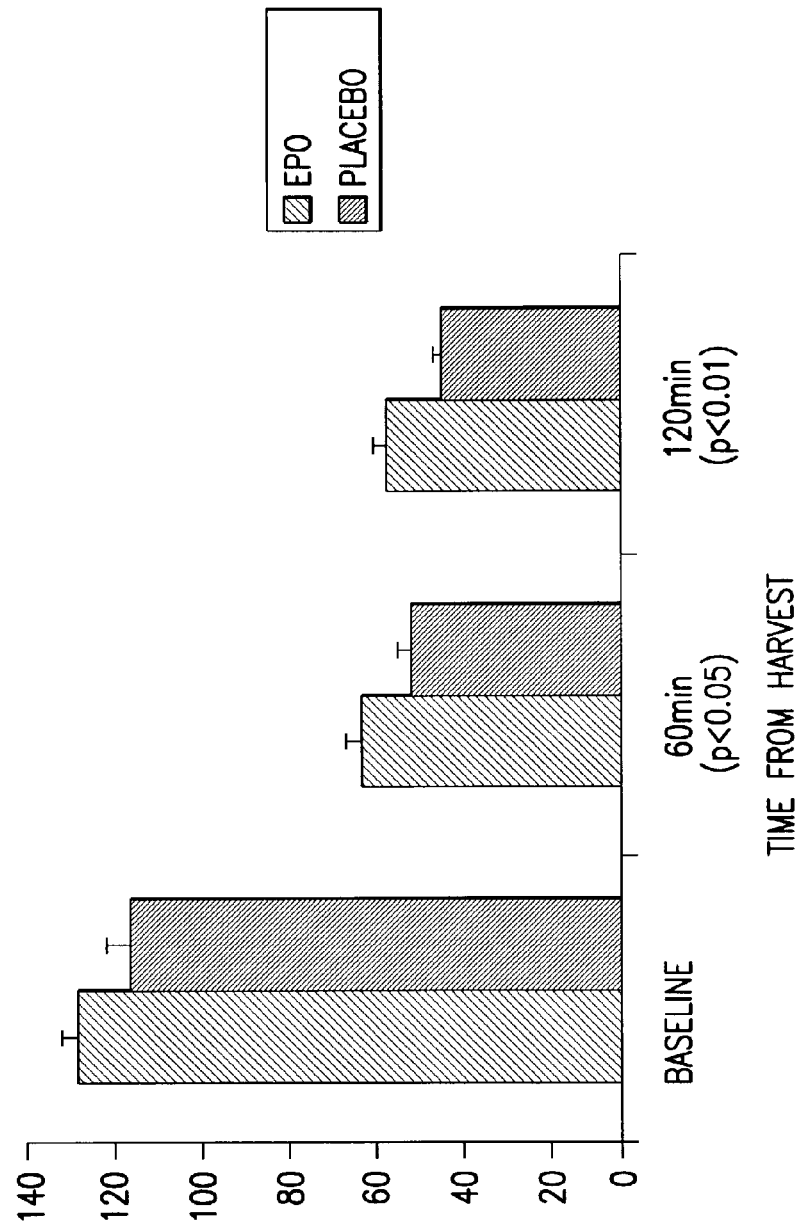
FIG. 3 shows the maintenance of the function of a heart prepared for transplantation by erythropoietin.

Adult male rats given recombinant human erythropoietin (5000 U/kg body weight) 24 hrs previously are anesthetized and prepared for coronary artery occlusion. An additional dose of erythropoietin is given at the start of the procedure and the left main coronary artery occluded for 30 minutes and then released. The same dose of erythropoietin is given daily for one week after treatment. The animals are then studied for cardiac function. As FIG. 3 illustrates, animals receiving a sham injection (saline) demonstrated a large increase in the left end diastolic pressure, indicative of a dilated, stiff heart secondary to myocardial infarction. In contradistinction, animals receiving erythropoietin suffered no decrement in cardiac function, compared to sham operated controls (difference significant at the $p<0.01$ level).

EXAMPLE 4

Erythropoietin Molecules

Native erythropoietin may be modified to tailor its activities for a specific tissue or tissues. Several non-limiting strategies that may be carried out to achieve this desired tissue specificity include modifications that remove or modify the glycosylation moieties, of which erythropoietin has three N-linked and one O-linked. Such variants of glycosylated erythropoietin can be produced in a number of ways. For example, the sialic acids which terminate the end of the sugar chains can be removed by specific sialidases depending on the chemical linkage connecting the sialic acid to the sugar chain. Alternatively, the glycosylated structure can be dismantled in different ways by using other enzymes that cleave at specific linkages. To validate these principles, recombinant human erythropoietin was desialized using Sialidase A (Prozyme Inc.) according to the manufacturer's protocol. Successful chemical modification was confirmed by running the reaction product on an SDS polyacrylamide gel and staining the resultant bands which showed that the chemically-modified erythropoietin possessed an apparent molecular weight of ~31 kD as expected, compared to unmodified erythropoietin which was ~34 kD and by measuring the sialic acid residues remaining by chemical means to be <0.1 mole/mole of erythropoietin.

In another modification wherein the amino acid residues of erythropoietin are modified, arginine residues were modified by using phenylglyoxal according to the protocol of Takahashi (1977, *J. Biochem.* 81:395-402) carried out for variable lengths of time ranging from 0.5 to 3 hrs at room temperature. The reaction was terminated by dialyzing the reaction mixture against water. Use of such modified forms of erythropoietin is fully embraced herein.

Figure 4:
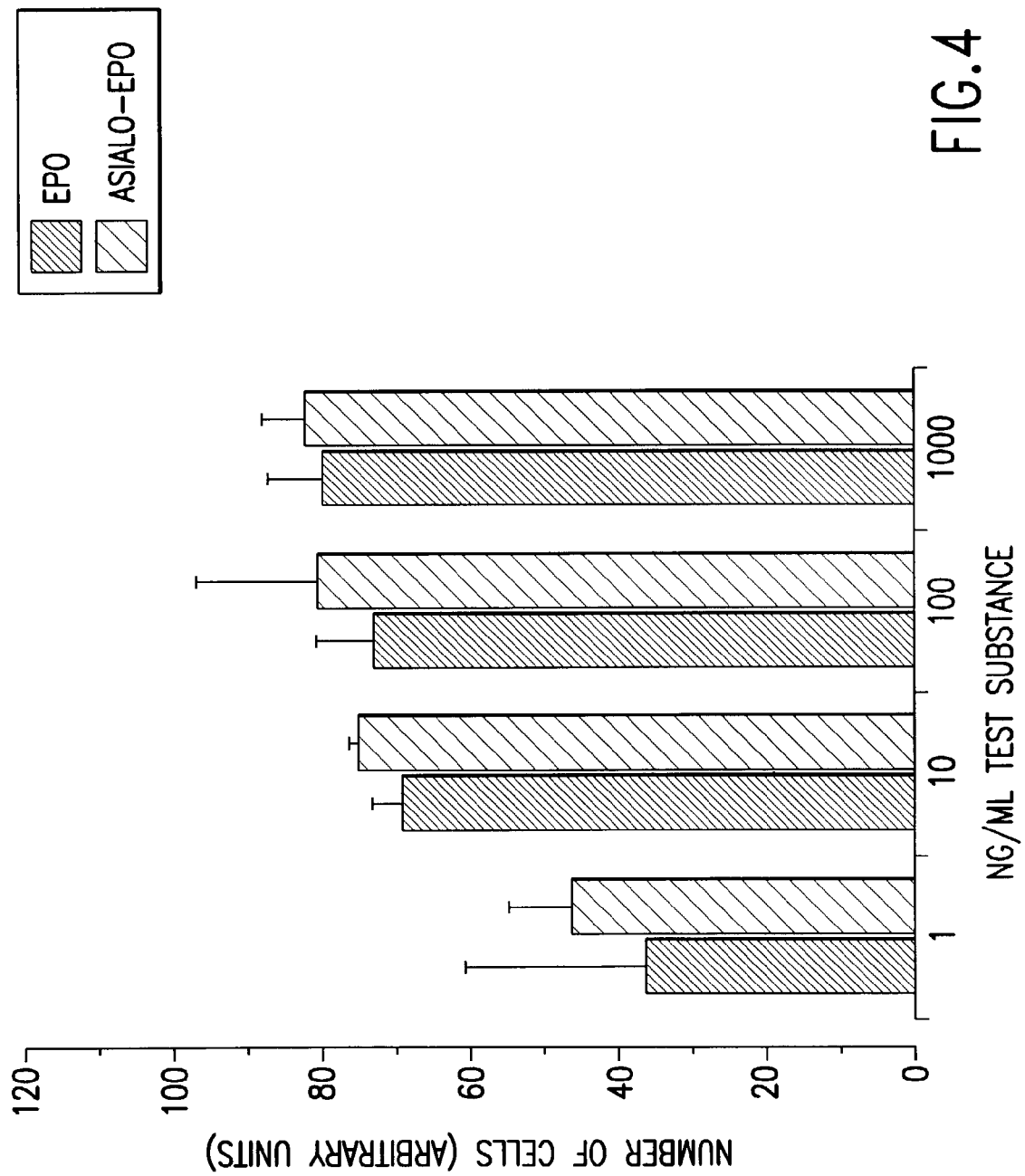
FIG. 4 compares the in-vitro efficacy of erythropoietin and asialoerythropoietin on the viability of serum-starved P19 cells.
Figure 5:
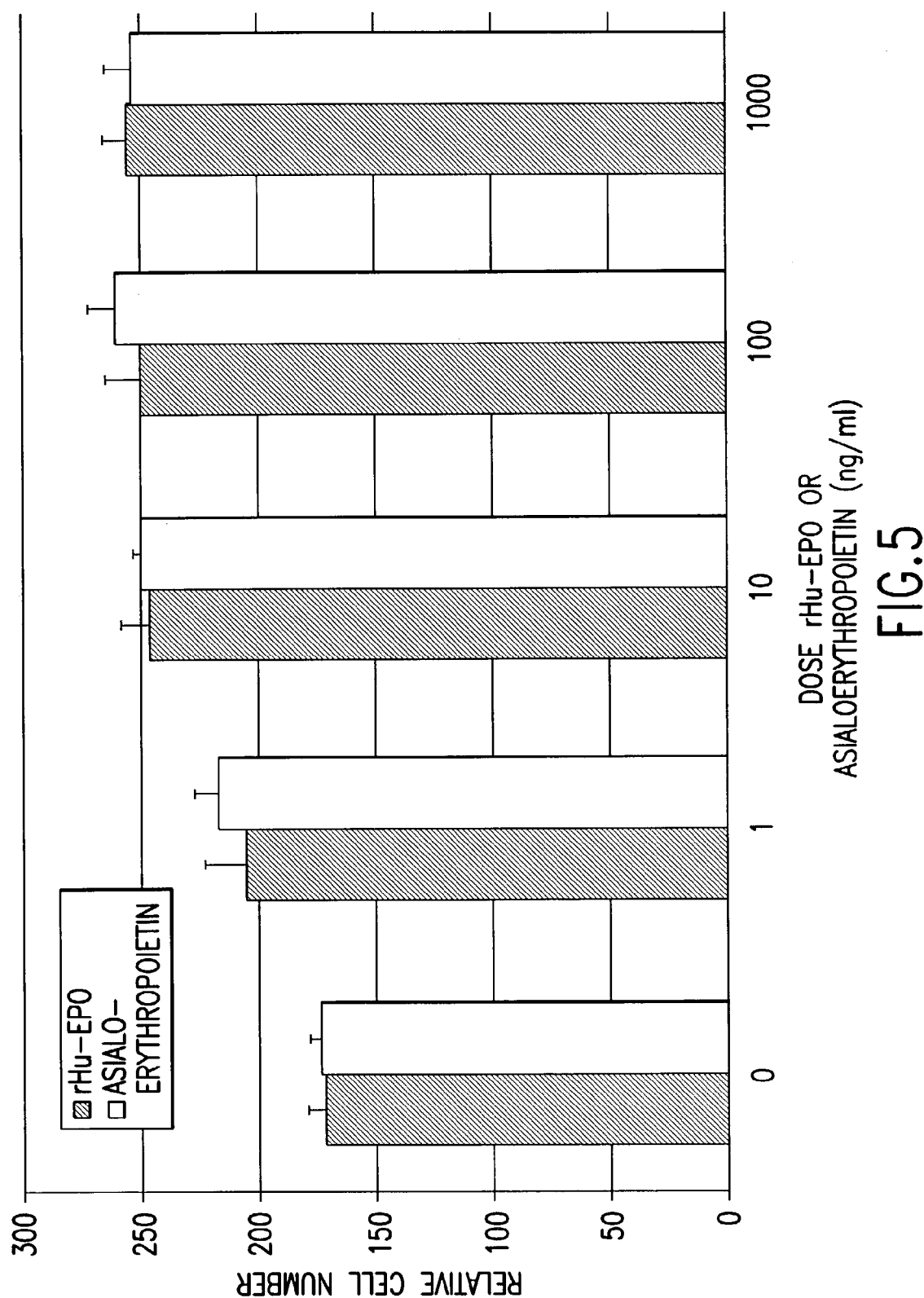
FIG. 5 is another experiment which compares the in-vitro efficacy of erythropoietin and asialoerythropoietin on the viability of serum-starved P19 cells.
Figure 6:
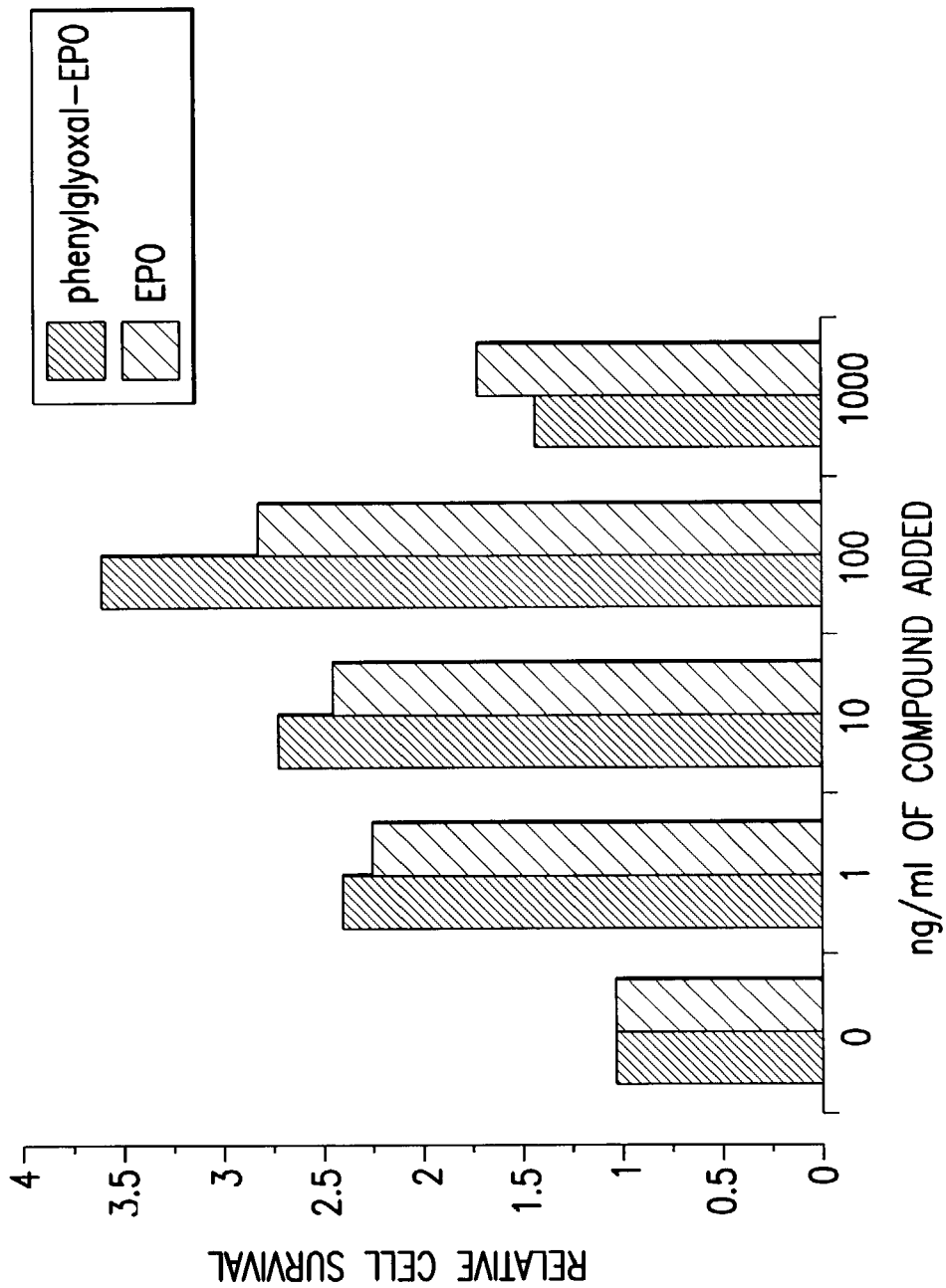
FIG. 6 compares the in-vitro efficacy of erythropoietin and phenylglyoxal-modified erythropoietin on the viability of serum-starved P19 cells.

Asialoerythropoietin and phenylglyoxalerythropoietin were as effective as native erythropoietin for neural cells in vitro as shown in FIGS. 4-6. In-vitro testing was carried out using neural-like embryonal carcinoma cells (P19) that undergo apoptosis upon the withdrawal of serum. Twenty-four hours before the removal of serum, 1-1000 ng/ml of erythropoietin or a modified erythropoietin was added to the cultures. The following day the medium was removed, the cells washed with fresh, non-serum containing medium, and medium containing the test substance (no serum) added back to the cultures for and additional 48 hours. To determine the number of viable cells, a tetrazolium reduction assay was performed (CellTiter 96; Promega, Inc.). As FIGS. 4-5 illustrate, asialoerythropoietin appears to be of equal potency to erythropoietin itself in preventing cell death. The phenylglyoxal-modified erythropoietin was tested using the neural-like P19 cell assay described above. As FIG. 6 illustrates, this chemically-modified erythropoietin fully retains its neuroprotective effects.

Figure 7:
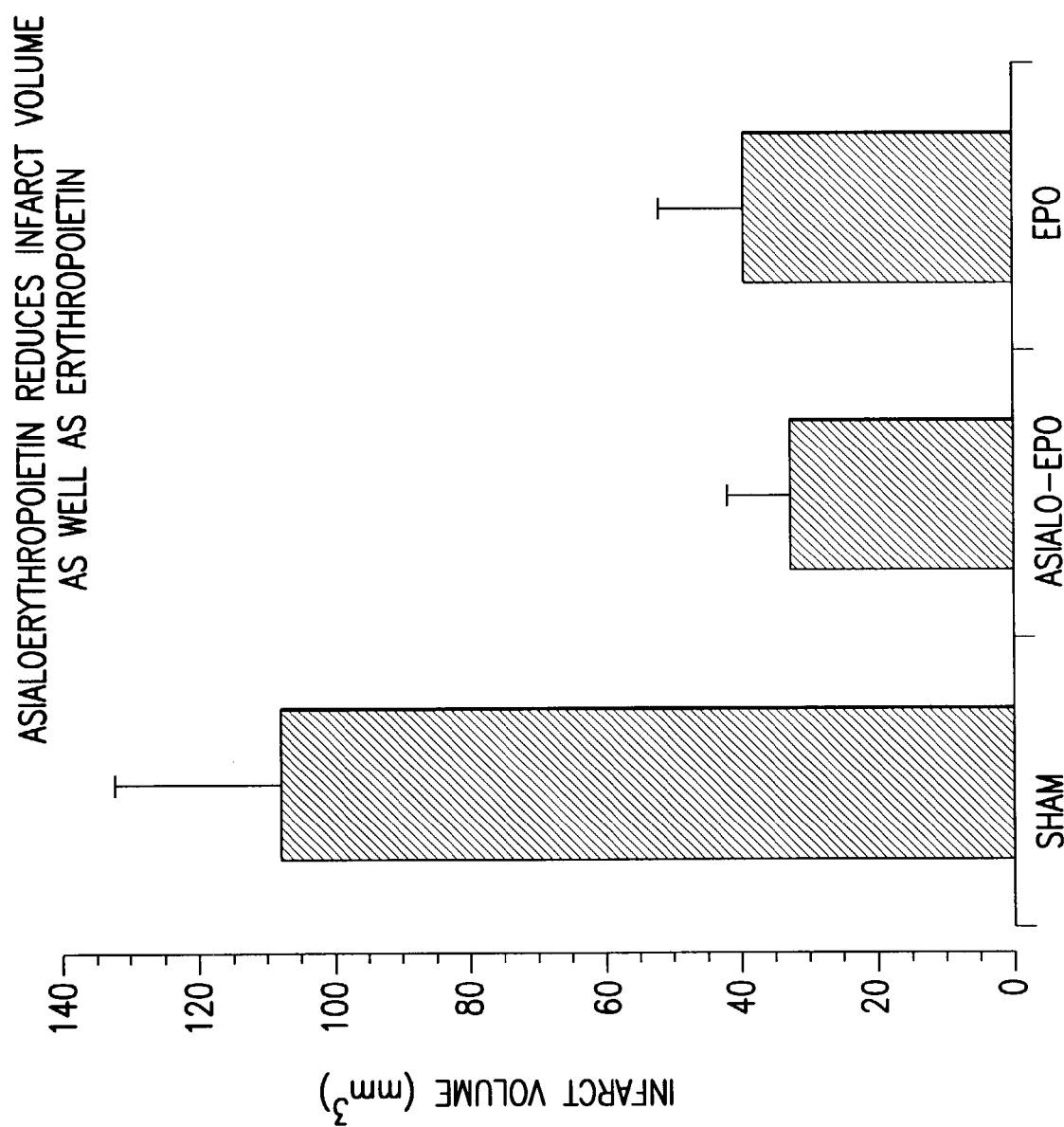
FIG. 7 shows protection of erythropoietin and asialoerythropoietin in a rat focal cerebral ischemia model.
Figure 8:
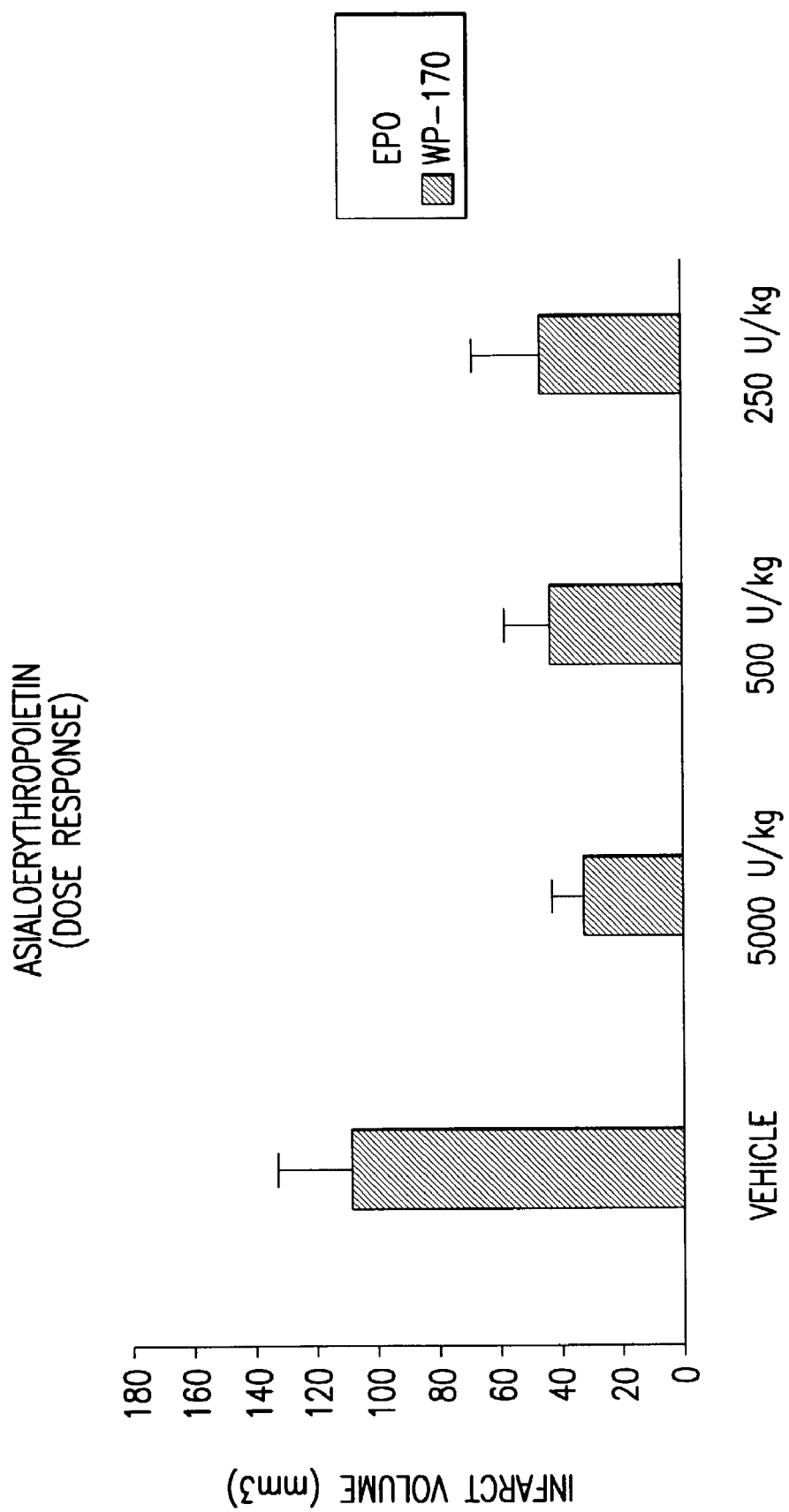
FIG. 8 shows a dose response comparing the efficacy of human erythropoietin and human asialoerythropoietin in middle cerebral artery occlusion in a model of ischemic stroke

Retention of neuroprotective activity in vivo was confirmed using a rat focal ischemia model in which a reversible lesion in the territory of the middle cerebral artery is performed as described previously (Brines et al., 2000, *Proc. Nat. Acad. Sci. U.S.A.* 97:10526-31). Adult male Sprague-Dawley rats were administered asialoerythropoietin or erythropoietin (5000 U/kgBW intraperitoneally) or vehicle at the onset of the arterial occlusion. Twenty-four hours later, the animals were sacrificed and their brains removed for study. Serial sections were cut and stained with tetrazolium salts to identify living regions of the brain. As shown in FIG. 7, asialoerythropoietin was as effective as native erythropoietin in providing neuroprotection from 1 hour of ischemia. FIG. 8 shows the results of another focal ischemia model in which a comparative dose response was performed with erythropoietin and asialoerythropoietin. At the lowest dose of 250 U/kg, asialoerythropoietin afforded protection whereas unmodified erythropoietin did not.

EXAMPLE 5

Modification of Primary Structure of Erythropoietin and Effectiveness at Neuronal Protection A number of mutant erythropoietin molecules have been described which do not bind to the erythrocyte erythropoietin receptor and thus do not support erythropoiesis in vivo or in vitro. Some of these molecules will nevertheless mimic the actions of erythropoietin itself in other tissues or organs. For example, a 17-mer containing the amino-acid sequence of 31-47 of native eryhropoietin is inactive for erythropoiesis but fully active for neural cells in vitro (Campana & O'Brien, 1998: Int. J. Mol. Med. 1:235-41).

Derivative erythropoietins desirable for the uses described herein may be generated by guanidination, amidination, trinitrophenylation, acetylation, succinylation, nitration, or modification of arginine residues or carboxyl groups, among other procedures as mentioned herein above, to produce erythropoietins which maintain their activities for specific organs and tissues but not for others, such as erythrocytes. When erythropoietin is subjected to the above reactions, it has been found that in general the resultant molecule lacks both in-vivo and in-vitro erythropoietic activity (e.g., Satake et al; 1990, *Biochim. Biophys. Acta* 1038:125-9). Some examples of the preparation of modified erythropoietins are described below.

Figure 10:
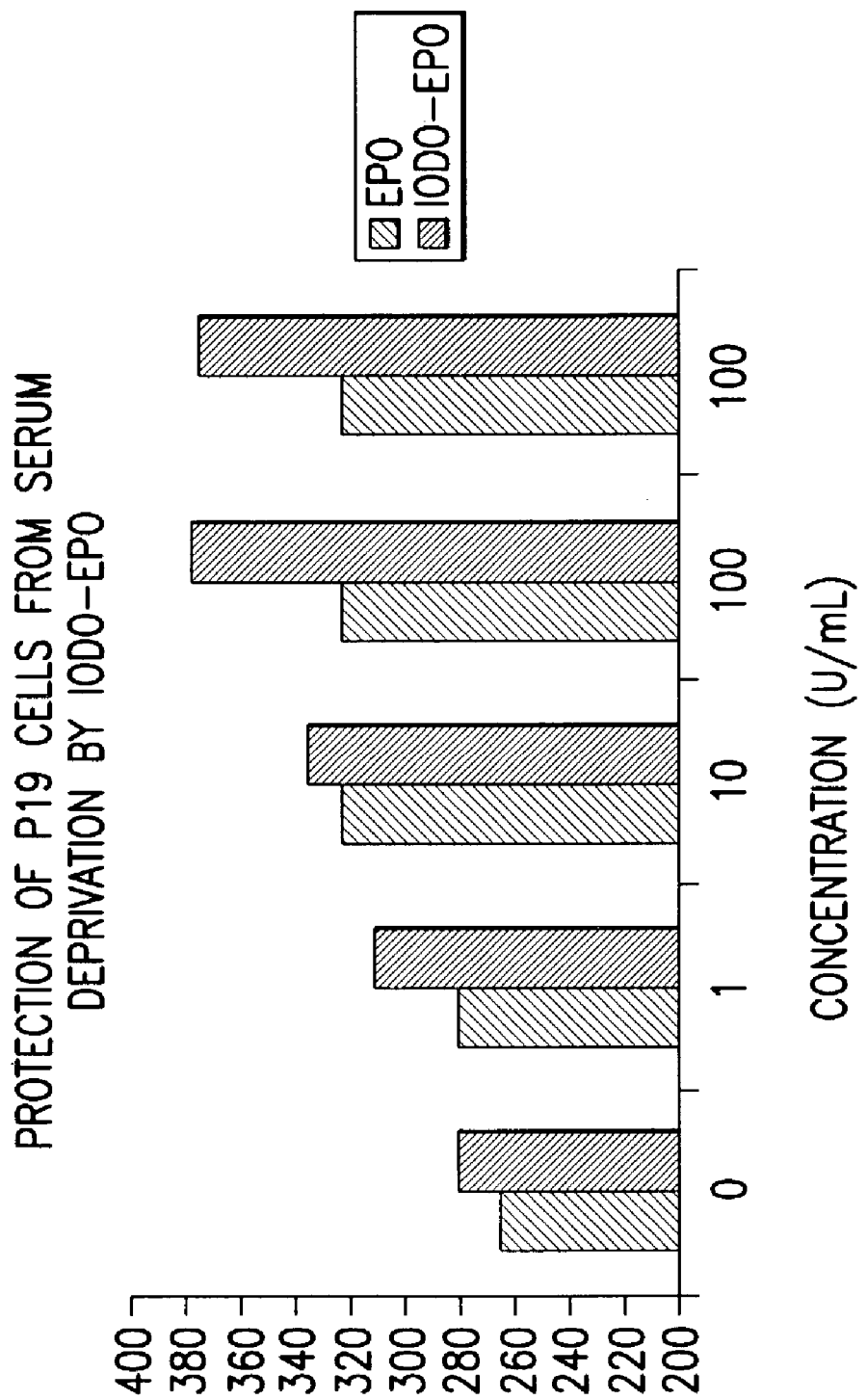
FIG. 10 shows the activity of iodinated erythropoietin in the P19 assay.
Figure 11A:
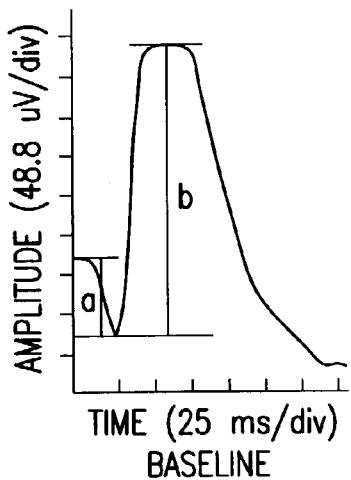
FIG. 11 depicts the effects of erythropoietin treatment in a rat glaucoma model.
Figure 11B:
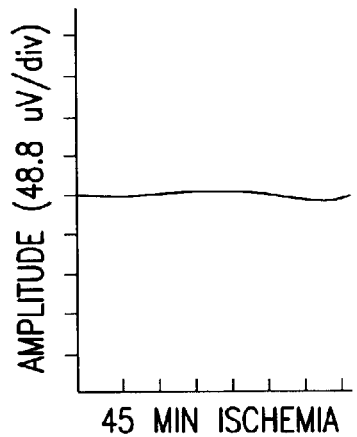
Figure 11C:
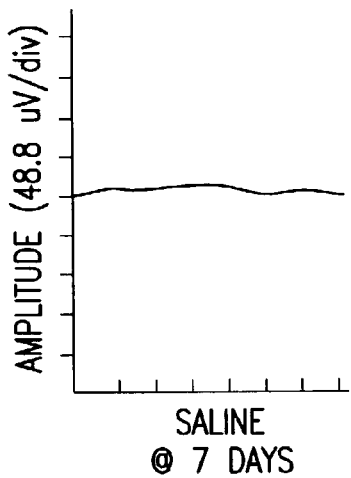
Figure 11D:
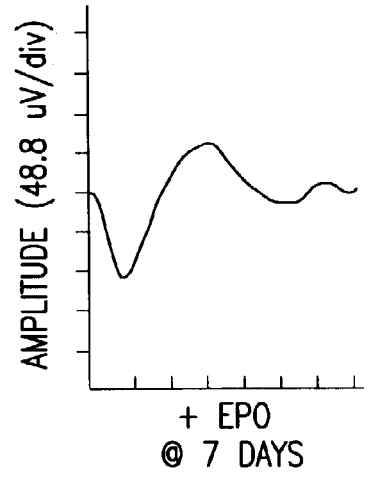

Biotinylation at free amino groups of erythropoietin. 0.2 mg D-biotinoyl-e-aminocaproic acid-N-hydroxysuccinimide ester (Boehringer Manheim #1418165) was dissolved in 100 ul DMSO. This solution was combined with 400 ul PBS containing approximately 0.2 mg erythropoietin in a foil covered tube. After incubation for 4 hours at room temperature, the unreacted biotin was Separated by gel filtration on a Centricon 10 column. As shown by FIG. 10, this biotinylated erythropoietin protects p19 cells from serum withdrawal.

Figure 9:
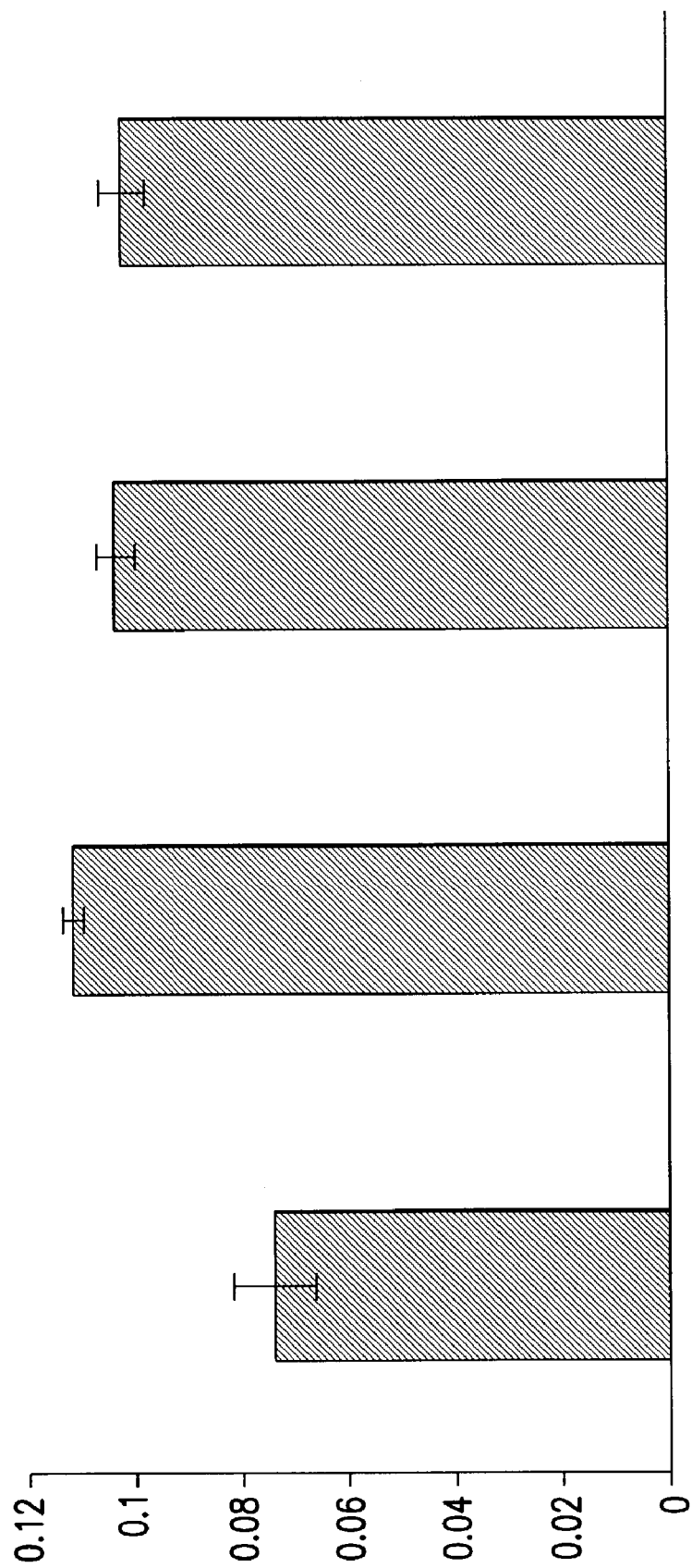
FIG. 9 shows the effect of biotinylated erythropoietin and asialoerythropoietin in the P19 assay.

In "Biotinylated recombinant human erythropoietins: Bioactivity and Utility as a receptor ligand" by Wojchowski et al. Blood, 1989, 74(3):952-8, the authors use three different methods of biotinylating erythropoietin. Biotin is added to (1) the sialic acid moieties (2) carboxylate groups (3) amino groups. The authors use a mouse spleen cell proliferation assay to demonstrate that (1) the addition of biotin to the sialic acid moieties does not inactivate the biological activity of erythropoietin (2) the addition of biotin to carboxylate groups led to substantial biological inactivation of erythropoietin (3) the addition of biotin to amino groups resulted in complete biological inactivation of erythropoietin. These methods and modifications are fully embraced herein. FIG. 9 shows the activity of biotinylated erythropoietin and asialoerythropoietin in the serum-starved P19 assay.

Iodination of erythropoietin. Method 1—Iodo Beads. One Iodo Bead (Pierce, Rockford, Ill.) was incubated in 100 ul PBS (20 mM sodium phosphate, 0.15M NaCl, pH 7.5) containing 1 mCi free Na$^{125}$I for 5 minutes. 100 ug erythropoietin in 100 ul PBS was then added to the mixture. After a ten minute incubation period at room temperature, the reaction was stopped by removing the 200 ul solution from the reaction vessel (leaving the iodo bead behind). The excess iodine was removed by gel filtration on a Centricon 10 column. As shown in FIG. 11, iodo-erythropoietin produced in this manner is efficacious in protecting P19 cells from serum withdrawal.

Method 2—Chloramine T. 100 ug erythropoietin in 100 ul PBS was added to 500 uCi Na$^{125}$I were mixed together in an eppendorf tube. 25 ul chloramines T (2 mg/ml) was then added and the mixture was incubated for 1 minute at room temperature. 50 ul of Chloramine T stop buffer (2.4 mg/ml sodium metabisulfite, 10 mg/ml tyrosine, 10% glycerol, 0.1% xylene in PBS was then added. The iodotyrosine and iodinated erythropoietin were then separated by gel filtration on a Centricon 10 column.

Lysine modifications: Carbamylation: erythropoietin (100 ug) was modified with potassium cyanate as described in Plapp et al ("Activity of bovine pancreatic deoxyribonuclease A with modified amino groups" 1971, J. Biol. Chem. 246, 939-845).

Trinitrophenylation: erythropoietin (100 ug) was modified with 2,4,6-trinitrobenzenesulfonate as described in Plapp et al ("Activity of bovine pancreatic deoxyribonuclease A with modified amino groups" 1971, J. Biol. Chem. 246, 939-845)

Acetylation: erythropoietin (100 ug) was incubated in 0.3M phosphate buffer (pH 7.2) containing an equal amount of acetic anhydride at 0° C. for 1 hour. The reaction was stopped by dialysis against distilled water.

Succinylation: erythropoietin (100 ug) in 0.5 M NaHCO3 (pH 8.0) was incubated with a 15 molar excess of succinic anhydride at 15° C for 1 hour. The reaction was stopped by dialysis against distilled water.

Arginine modifications: erythropoietin was modified with 2,3 butanedione as described in Riordan ("Functional arginyl residues in carboxypeptidase A. Modification with butanedione" Riordan J F, Biochemistry 1973, 12(20): 3915-3923).

Erythropoietin was modified with cylcohexanone as in Patthy et al ("Identification of functional arginine residues in ribonuclease A and lysozyme" Patthy, L, Smith E L, J. Biol. Chem 1975 250(2): 565-9).

Erythropoietin was modified with phenylglyoxal as described in Werber et al. ("Proceedings: Carboxypeptidase B: modification of functional arginyl residues" Werber, MM, Sokolovsky M Isr J Med Sci 1975 11(11): 1169-70).

Tyrosine modifications: erythropoietin (100 ug) was incubated with tetranitromethane as previously described in Nestler et al "Stimulation of rat ovarian cell steroidogenesis by high density lipoproteins modified with tetranitromethane" Nestler J E, Chacko G K, Strauss J F 3rd. J Biol Chem Jun. 25, 1985; 260(12):7316-21).

Glutamic acid (and aspartic acid) modifications: In order to modify carboxyl groups, erythropoietin (100 ug) was incubated with 0.02 M EDC in 1M glycinamide at pH 4.5 at room temperature for 60 minutes as described in Carraway et al "Carboxyl group modification in chymotrypsin and chymotrypsinogen." Carraway K L, Spoerl P, Koshland D E Jr. J Mol Biol May 28, 1969; 42(1):133-7.

Tryptophan residue modifications: erythropoietin (100 ug) was incubated with 20 uM n-bromosuccinimide in 20 mM potassium phosphate buffer (pH 6.5) at room temperature as described in Ali et al., J Biol Chem. Mar. 3, 1995; 270(9): 4570-4. The number of oxidized tryptophan residues was determined by the method described in Korotchkina (Korotchkina, LG et al Protein Expr Purif. February 1995; 6(1): 79-90).

Removal of amino groups: In order to remove amino groups of erythropoietin (100 ug) was incubated with in PBS (pH 7.4) containing 20 mM ninhydrin (Pierce Chemical, Rockford, Ill.), at 37 C for two hours as in Kokkini et al (Kokldini, G., et al "Modification of hemoglobin by ninhydrin" Blood, Vol. 556, No 4 1980: 701-705). Reduction of the resulting aldehyde was accomplished by reacting the product with Sodium borohydride or lithium aluminum hydride. Specifically, erythropoietin (100 ug) was incubated with 0.1M sodium borohydride in PBS for 30 minutes at room temperature. The reduction was terminated by cooling the samples on ice for 10 minutes and dialyzing it against PBS, three times, overnight. (Kolkini, G., Blood, Vol. 556, No 4 1980: 701-705). Reduction using lithium aluminum hydride was accomplished by incubating erythropoietin (100 ug) with 0.1M lithium aluminum hydride in PBS for 30 minutes at room temperature. The reduction was terminated by cooling the samples on ice for 10 minutes and dialyzing it against PBS, three times, overnight.

Disulfide reduction and stabilization: erythropoietin (100 ug) was incubated with 500 mM DTT for 15 minutes at 60° C. 20 mM iodoacetamide in water was then added to the mixture and incubated for 25 minutes, at room temperature in the dark.

Limited proteolysis: Erythropoietin can be subjected to a limited chemical proteolysis that targets specific residues. Erythropoietin was reacted with 2-(2-nitrophenylsulfenyl)-3-methyl-3'-bromoindolenine which cleaves specifically after tryptophan residues in a 50 times excess in 50% acetic acid for 48 hours in the dark at room temperature in tubes capped under nitrogen pressure. The reaction was terminated by quenching with tryptophan and desalting.

EXAMPLE 6

Protection of Retinal Ischemia by Peripherally-Administered Erythropoietin

Figure 12:
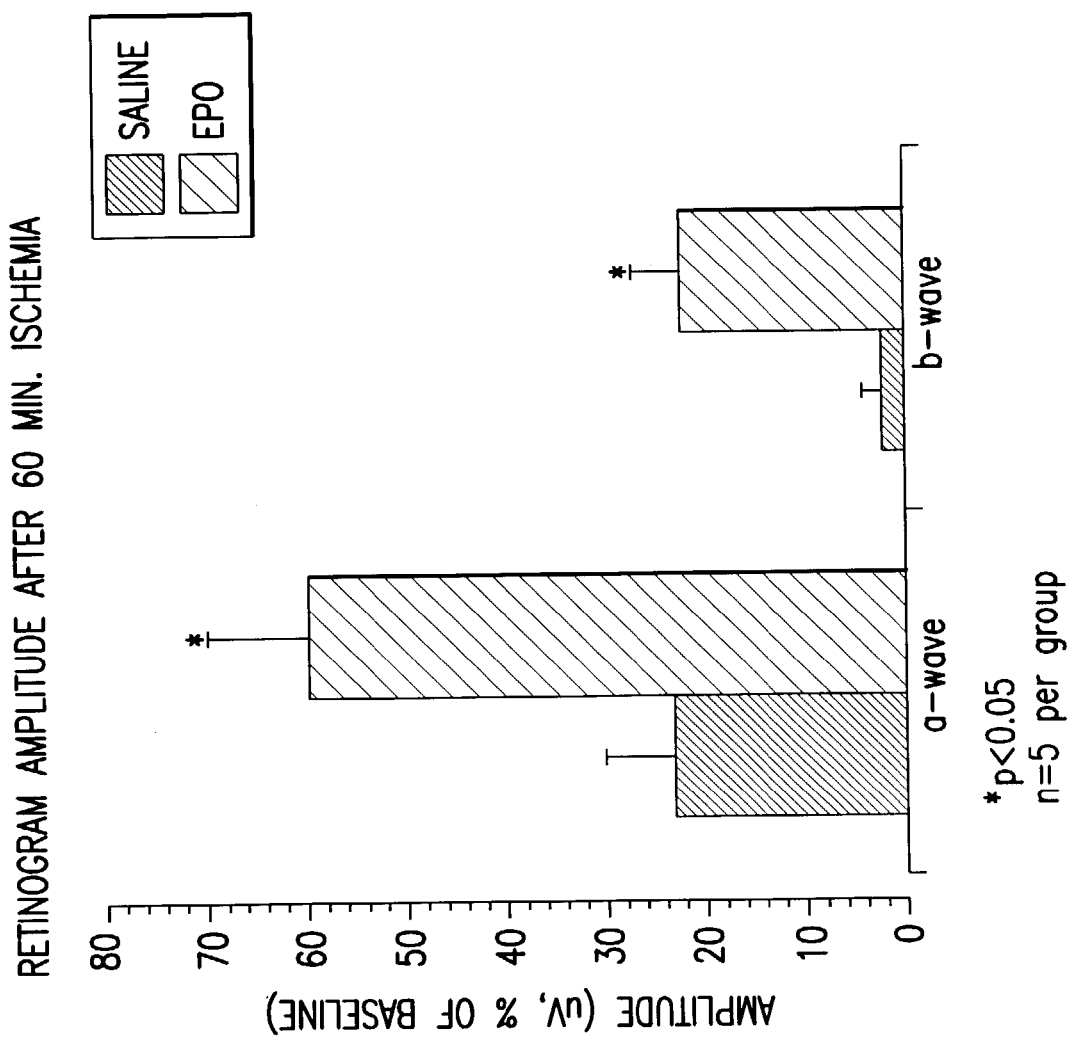
FIG. 12 shows the extent of preservation of retinal function by erythropoietin in the rat glaucoma model.

Retinal cells are very sensitive to ischemia such that many will die after 30 minutes of ischemic stress. Further, subacute or chronic ischemia underlies the deterioration of vision which accompanies a number of common human diseases, such as diabetes mellitus, glaucoma, and macular degeneration. At the present time there are no effective therapies to protect cells from ischemia. A tight endothelial barrier exists between the blood and the retina that excludes most large molecules. To test whether peripherally-administered erythropoietin will protect cells sensitive to ischemia, an acute, reversible glaucoma rat model was utilized as described by Rosenbaum et al. (1997; *Vis. Res.* 37:3443-51). Specifically, saline was injected into the anterior chamber of the eye of adult male rats to a pressure above systemic arterial pressure and maintained for 60 minutes. Animals were administered saline or 5000 U erythropoietin/kg body weight intraperitoneally 24 hours before the induction of ischemia, and continued as a daily dose for 3 additional days. Electroretinography was performed on dark-adapted rats 1 week after treatment. FIGS. 11-12 illustrate that the administration of erythropoietin is associated with good preservation of the electroretinogram (ERG) (Panel D), in contrast to animals treated with saline alone (Panel C), for which very little function remained. FIG. 11 compares the electroretinogram a- and b-wave amplitudes for the erythropoietin-treated and saline-treated groups, and shows significant protection afforded by erythropoietin.

EXAMPLE 7

Figure 13:
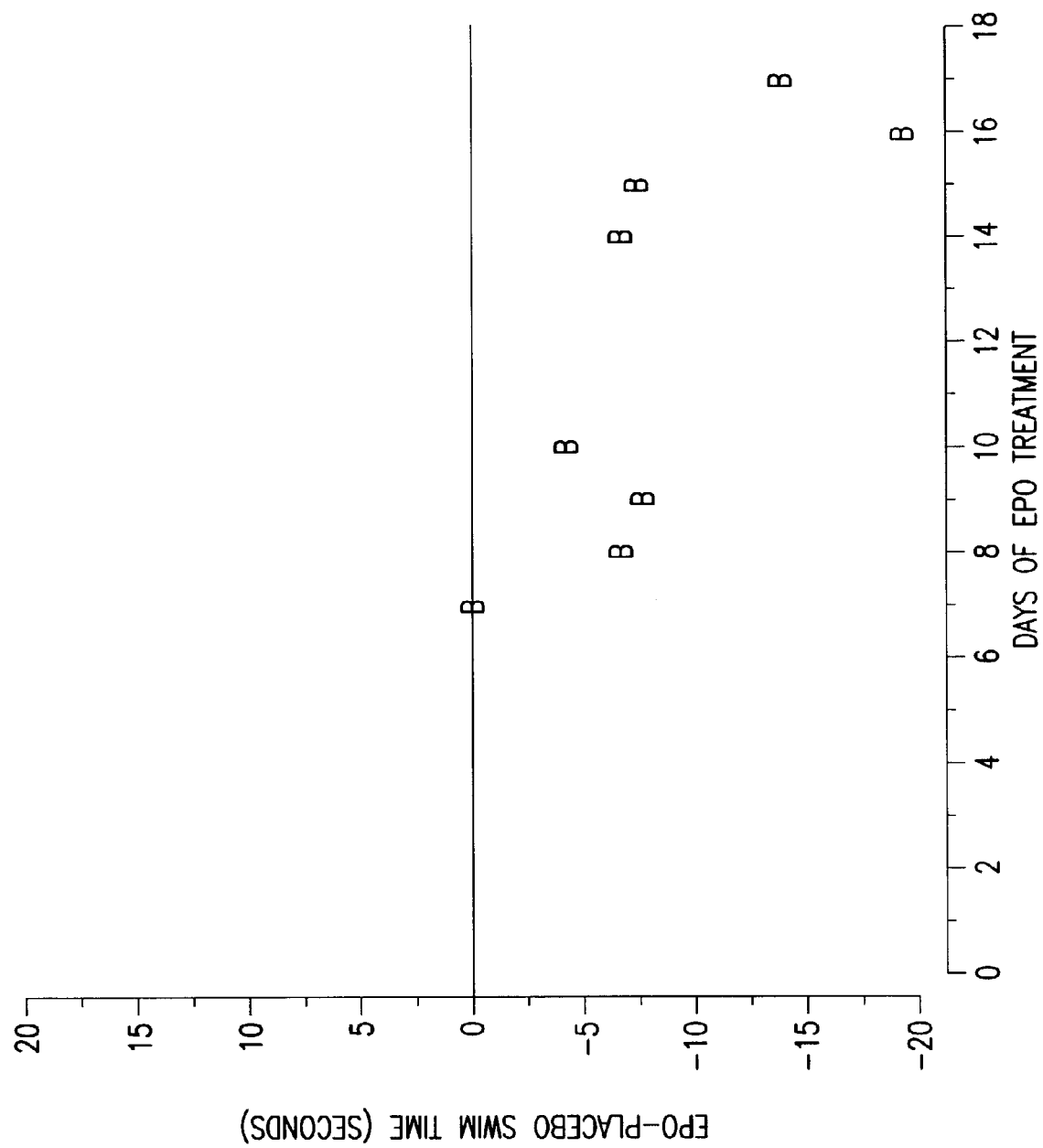
FIG. 13 depicts the restoration of cognitive function following brain trauma by administration of erythropoietin starting five days after trauma.
Figure 14:
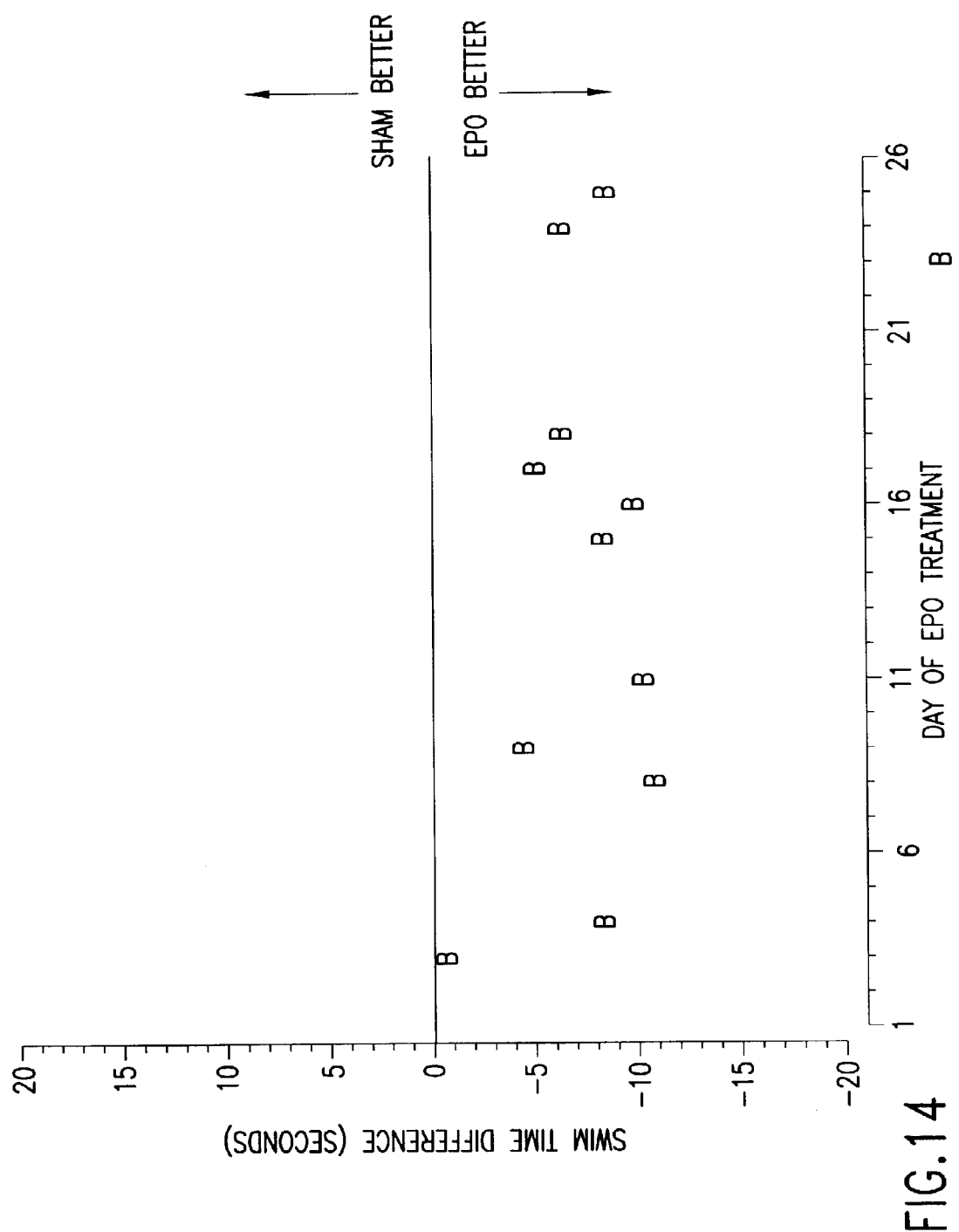
FIG. 14 depicts the restoration of cognitive function following brain trauma by administration of erythropoietin starting 30 days after trauma.

Restorative Effects of Erythropoietin on Diminished Cognitive Function Arising from Brain Injury In a study to demonstrate the ability of erythropoietin to restore diminished cognitive function in mice after receiving brain trauma, female Balb/c mice were subject to blunt brain trauma as described in Brines et al. PNAS 2000, 97; 10295-10672 and five days later, daily erythropoietin administration of 5000 U/kg-bw intraperitoneally was begun. Twelve days after injury, animals were tested for cognitive function in the Morris water maze, with four trials per day. While both treated and untreated animals performed poorly in the test (with swim times of about 80 seconds out of a possible 90 seconds), FIG. 13 shows that the erythropoietin-treated animals performed better (in this presentation, a negative value is better). Even if the initiation of erythropoietin treatment is delayed until 30 days after trauma (FIG. 14), restoration of cognitive function is also seen.

EXAMPLE 8

Kainate Model

Figure 15:
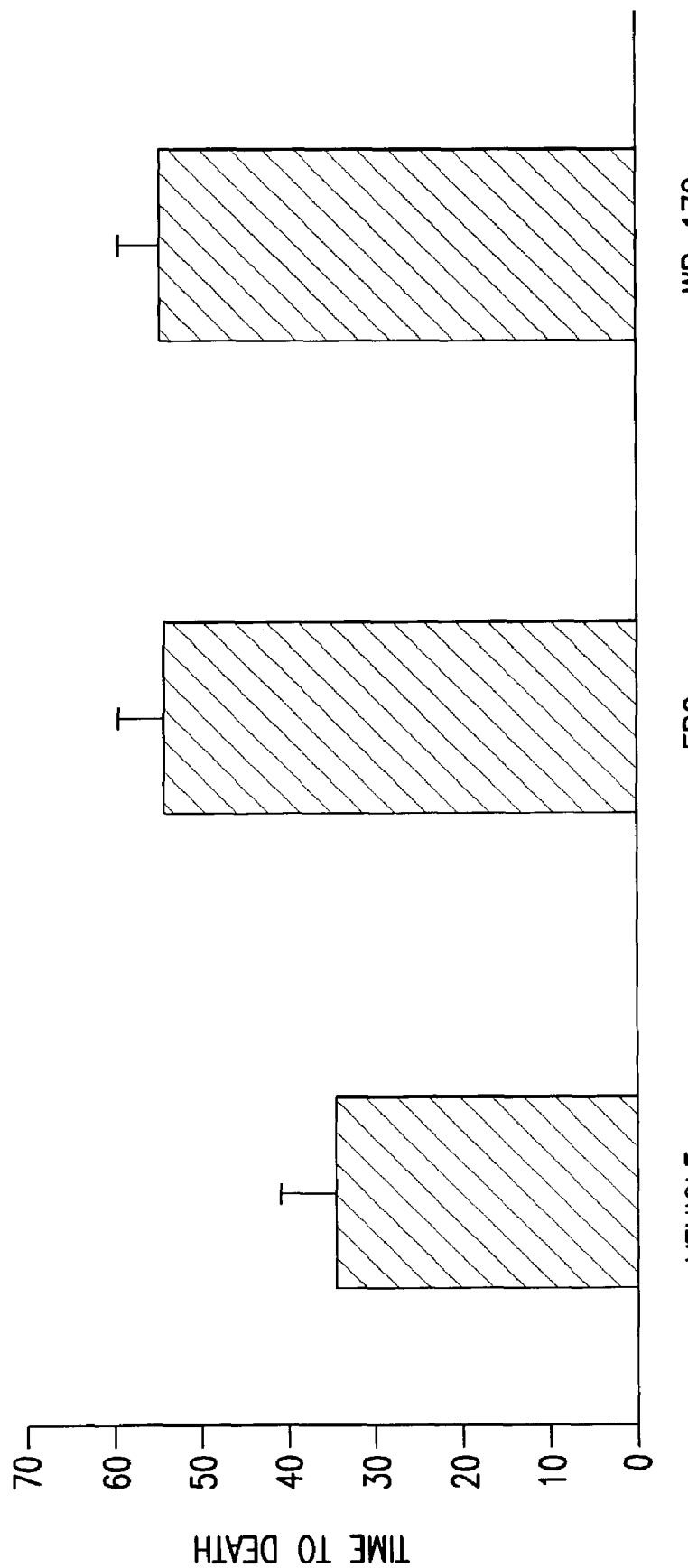
FIG. 15 depicts the efficacy of human asialoerythropoietin in a kainate model of cerebral toxicity.

In the kainate neurotoxicity model, asialoerythropoietin was administered according to the protocol of Brines et al. Proc. Nat. Acad. Sci. U.S.A. 2000, 97; 10295-10672 at a dose of 5000 U/kg-bw given intraperitoneally 24 hours before the administration of 25 mg/kg kainate is shown to be as effective as erythropoietin, as shown by time to death (FIG. 15).

The invention is not to be limited in scope by the specific embodiments described which are intended as single illustrations of individual aspects of the invention, and functionally equivalent methods and components are within the scope of the invention. Indeed various modifications of the invention, in addition to those shown and described herein will become apparent to those skilled in the art from the foregoing description and accompanying drawings. Such modifications are intended to fall within the scope of the appended claims.

All references cited herein are incorporated by reference herein in their entireties for all purposes.

What is claimed is:

1. A method for protecting, maintaining, enhancing or restoring the function or viability of erythropoietin-responsive mammalian cells, tissues and organs comprising administering to a mammal a pharmaceutical composition comprising a therapeutically effective amount of an erythropoietin having at least one of the following modifications:
   (i) at least one or more chemically modified lysine residues; or
   (ii) a chemical modification of the N-terminal amino group of the erythropoietin molecule,
   such that the function or viability of erythropoietin-responsive mammalian cells, tissues and organs is protected, maintained, enhanced or restored without causing an increase in hemoglobin concentration or hematocrit in said mammal.

2. The method of claim 1 wherein said erythropoietin is expressed in an insect or plant cell.

3. The method of claim 1 wherein said erythropoietin molecule has at least one biotinylated lysine or biotinylated N-terminal amino group.

4. The method of claim 1 wherein said erythropoietin is glucitolyl lysine erythropoietin or fructosyl lysine erythropoietin.

5. The method of claim 1 wherein a lysine residue of said erythropoietin is carbamylated.

6. The method of claim 1 or 5 wherein said mammalian cell or its associated cells, tissues, or organs is selected from the group consisting of bone, liver, kidney, small intestine, testes, ovary, pancreas and endometrial cells, tissues and organs.

7. The method of claim 1 wherein a lysine residue of said erythropoietin is acylated.

8. The method of claim 7 wherein a lysine residue of said erythropoietin is acetylated.

9. The method of claim 7 wherein a lysine residue of said erythropoietin is succinylated.

10. The method of claim 1 wherein a lysine residue of said erythropoietin is modified by 2,4,6-trinitrobenzenesulfonate sodium or another salt thereof.

11. The method of claim 1 wherein erythropoietin-responsive cell or tissue is neuronal, retinal, muscle, heart, lung, liver, kidney, small intestine, adrenal cortex, adrenal medulla, capillary endothelial, testes, ovary, or endometrial cell or tissue.

12. The method of claim 1 wherein the N-terminal amino group of said erythropoietin is carbamylated.

13. A method for protecting, maintaining, enhancing or restoring the function or viability of erythropoietin-responsive mammalian cell or its associated cells, tissues, or organs, comprising administering to a mammal a pharmaceutical composition comprising a therapeutically effective amount of an erythropoietin,
    wherein said mammalian cell or its associated cells, tissues, or organs is selected from the group consisting of bone, liver, kidney, small intestine, testes, ovary, pancreas and endometrial cells, tissues and organs, and wherein the erythropoietin is carbamylated.

* * * * *